(12) United States Patent
Bassaganya-Riera et al.

(10) Patent No.: US 12,150,961 B2
(45) Date of Patent: *Nov. 26, 2024

(54) THERAPIES WITH LANTHIONINE C-LIKE PROTEIN 2 LIGANDS AND CELLS PREPARED THEREWITH

(71) Applicant: NImmune Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US)

(73) Assignee: NImmune Biopharma, Inc., Blacksburg, VA (US)

( * ) Notice: Subject to any disclaimer, the term of this patent is extended or adjusted under 35 U.S.C. 154(b) by 442 days.

This patent is subject to a terminal disclaimer.

(21) Appl. No.: 17/524,883

(22) Filed: Nov. 12, 2021

(65) Prior Publication Data

US 2022/0072044 A1  Mar. 10, 2022

Related U.S. Application Data

(63) Continuation of application No. 16/193,640, filed on Nov. 16, 2018, now Pat. No. 11,197,891.

(60) Provisional application No. 62/592,692, filed on Nov. 30, 2017.

(51) Int. Cl.
| | | |
|---|---|---|
| *A61K 35/17* | (2015.01) |
| *A01K 67/0276* | (2024.01) |
| *A61P 1/00* | (2006.01) |
| *C12N 5/0783* | (2010.01) |
| *A61K 35/12* | (2015.01) |

(52) U.S. Cl.
CPC ........... *A61K 35/17* (2013.01); *A01K 67/0276* (2013.01); *A61P 1/00* (2018.01); *C12N 5/0636* (2013.01); *C12N 5/0637* (2013.01); *A01K 2217/075* (2013.01); *A01K 2217/15* (2013.01); *A01K 2217/206* (2013.01); *A01K 2227/105* (2013.01); *A01K 2267/035* (2013.01); *A61K 2035/122* (2013.01); *C12N 2501/15* (2013.01); *C12N 2501/2302* (2013.01); *C12N 2501/2312* (2013.01); *C12N 2501/385* (2013.01); *C12N 2501/999* (2013.01)

(58) Field of Classification Search
None
See application file for complete search history.

(56) References Cited

PUBLICATIONS

Carbo et al., An N,N-Bis(benzimidazolylpicolinoyl)piperazine (BT-11): A Novel Lanthionine Synthetase C-Like 2-Based Therapeutic for Inflammatory Bowel Disease. J. Med. Chem. Nov. 23, 2016;59(22):10113-10126. Epub Nov. 15, 2016.*

Leber et al., Oral Treatment with BT-11 Ameliorates Inflammatory Bowel Disease by Enhancing Regulatory T Cell Responses in the Gut. J. Immunol. 202(7):2095-2104, 2019.*

* cited by examiner

*Primary Examiner* — Ruixiang Li
(74) *Attorney, Agent, or Firm* — Daniel A. Blasiole; De Witt LLP

(57) ABSTRACT

Provided are compounds that target the lanthionine synthetase C-like protein 2 pathway and cells, such as immune cells, prepared in vitro with the compounds. The compounds and cells can be used to treat a number of conditions, including infectious diseases, hyperproliferative disorders, inborn errors of metabolism, chronic immunometabolic diseases, autoimmune diseases, organ transplant rejection, inflammatory disorders, and chronic pain, among others.

15 Claims, 35 Drawing Sheets ively active compounds and cells prepared therewith that can be used to treat and prevent conditions such as infectious diseases, hyperproliferative disorders, inborn errors of metabolism, chronic immunometabolic diseases, autoimmune diseases, organ transplant rejection, inflammatory disorders, and chronic pain, among others.

THERAPIES WITH LANTHIONINE C-LIKE PROTEIN 2 LIGANDS AND CELLS PREPARED THEREWITH

FIELD OF THE INVENTION

The present invention relates to the field of medical treatments for diseases and disorders. More specifically, the present invention relates to classes of biologically active compounds and cells prepared therewith that can be used to treat and prevent conditions such as infectious diseases, hyperproliferative disorders, inborn errors of metabolism, chronic immunometabolic diseases, autoimmune diseases, organ transplant rejection, inflammatory disorders, and chronic pain, among others.

BACKGROUND

Lanthionine synthetase C-like protein 2 (LANCL2) (also called "lanthionine C-like protein 2" or "lanthionine synthetase component C-like protein 2") is a signaling protein expressed throughout the body and particularly within cells of the GI tract and immune, nervous, and endocrine systems. The activation of LANCL2 serves to alter the metabolic processes of the cell and decrease the production of inflammatory mediators such as cytokines and chemokines while increasing anti-inflammatory cytokines. Previously, these effects have been examined in in vitro and in vivo systems exploring effects ranging from glucose tolerance in models of diabetes to reduction of gut inflammation in models of inflammatory bowel disease.

Cellular metabolism exerts control over the ability of immune cells to differentiate into inflammatory subsets, proliferate, and produce inflammatory cytokines and mediators (O'Neill, L. A., R. J. Kishton, and J. Rathmell, A guide to immunometabolism for immunologists. Nat Rev Immunol, 2016. 16(9): p. 553-65). Treatments targeting both immunity and metabolism are succeeding in clinical trials for diseases such as cancer (Mullard, A., Cancer metabolism pipeline breaks new ground. Nat Rev Drug Discov, 2016. 15(11): p. 735-737). The activation of LANCL2, the mechanism of action behind BT-11, was first shown to exert metabolic effects in non-immune cells, as a receptor for the natural and dietary compound, ABA (Sturla, L., et al., LANCL2 is necessary for abscisic acid binding and signaling in human granulocytes and in rat insulinoma cells. J Biol Chem, 2009. 284(41): p. 28045-57), and a signal transducer for the production of metabolic hormones, prior to the discovery of its role in inflammation (Lu, P., et al., Computational modeling-based discovery of novel classes of anti-inflammatory drugs that target lanthionine synthetase C-like protein 2. PLoS One, 2012. 7(4): p. e34643). The union between the metabolic and immunological actions of LANCL2 is a critical mechanism of action of BT-11 and other novel compounds targeting LANCL2.

The present invention provides the use of a series of classes of compounds, identified to target, bind and activate LANCL2, to elicit beneficial immunometabolic responses in various cells for the treatment of disease conditions, including but not limited to infectious diseases, hyperproliferative disorders, inborn errors of metabolism, chronic immunometabolic diseases, autoimmune diseases, organ transplant rejection, inflammatory disorders, and chronic pain, among others.

SUMMARY OF THE INVENTION

The present invention relates to the field of medical treatments for diseases and disorders. More, specifically, the present invention relates to the use of a class of compounds for the activation of beneficial immunometabolic effects in cells for the treatment of infectious diseases, hyperproliferative disorders, inborn errors of metabolism, chronic immunometabolic diseases, autoimmune diseases, organ transplant rejection, inflammatory disorders, and chronic pain, among others.

The compounds used for the treatments described herein include those of formula Z-Y-Q-Y'-Z', or a pharmaceutically acceptable salt or ester thereof, wherein:

Z is:

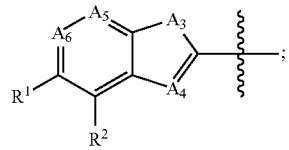

Y is:

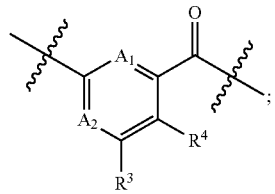

Q is piperazine-1,4-diyl; 2,5-diazabicyclo[2.2.1]heptane-2,5-diyl; 2,5-diazabicyclo[2.2.2]octane-2,5-diyl; 1,4-diazepane-1,4-diyl; benzene-1,4-diamine-$N^1,N^4$-diyl; ethane-1,2-diamine-$N^1,N^2$-diyl; $N^1,N^2$-dialkylethane-1,2-diamine-$N^1,N^2$-diyl; propane-1,3-diamine-$N^1,N^3$-diyl; $N^1,N^3$-dialkylpropane-1,3-diamine-$N^1,N^3$-diyl; 1,4-diaminoanthracene-9,10-dione-1,4-diyl; $C_6$ arene-1,4-diamine-$N^1,N^4$-diyl wherein the arene is substituted with one to four substituents in the 2, 3, 5, or 6 positions and wherein the substituents are independently selected from the group consisting of —C(O)O ($C_1$ to $C_6$)alkyl, OH, O($C_1$ to $C_6$)alkyl, ($C_1$ to $C_6$)alkyl, $CF_3$, F, Cl, and Br; or substituted piperazine-1,4-diyl wherein the piperazine is substituted with one to eight substituents in the 2, 3, 5, or 6 positions and wherein the substituents are independently selected from the group consisting of ($C_1$ to $C_6$)alkyl, aryl, aryl($C_1$ to $C_6$)alkyl, C(O)OH, and C(O)O($C_1$ to $C_6$)alkyl;

Y' is:

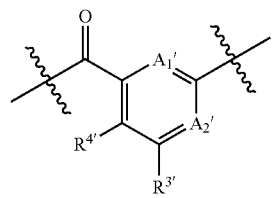

or a single bond; and

Z' is:

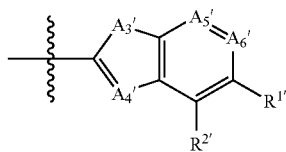

or $R^5$;

wherein:

Y' is a single bond only when Z' is $R^5$;

$A_1$ and $A_1'$, if present, are each independently N, N($C_1$ to $C_6$)alkyl, O, S, or $CR^6$;

$A_2$ and $A_2'$, if present, are each independently N or $CR^7$;

$A_3$ and $A_3'$, if present, are each independently $NR^8$, O, or S;

$A_4$ and $A_4'$, if present, are each independently N or $CR^9$;

$A_5$ and $A_5'$, if present, are each independently N or $CR^{10}$;

$A_6$ and $A_6'$, if present, are each independently N or $CR^{11}$;

$R^1$, $R^{1'}$, $R^2$, $R^{2'}$, $R^3$, $R^{3'}$, $R^4$, $R^{4'}$, $R^5$, $R^6$, $R^7$, $R^8$, $R^9$, $R^{10}$, and $R^{11}$, if present, are in each instance independently selected from the group consisting of hydrogen; alkyl; halo; trifluoromethyl; dialkylamino wherein each alkyl is independently selected; —$NH_2$; alkylamino; arylalkyl; heteroarylalkyl; heterocycloalkyl; substituted heterocycloalkyl substituted with 1 to 2 substituents independently selected from the group consisting of —C(O)OH, —C(O)O($C_1$ to $C_6$)alkyl, ($C_1$ to $C_6$)alkyl, —$CF_3$, F, Cl, and Br; and substituted heteroarylalkyl;

wherein the substituted heteroarylalkyl is substituted with 1 to 3 substituents independently selected from the group consisting of —$NH_2$; —NH($C_1$ to $C_6$)alkyl; —N(($C_1$ to $C_6$)alkyl)$_2$ wherein each alkyl is independently selected; alkyl; halo; aryl; substituted aryl substituted with 1 to 3 substituents independently selected from the group consisting of —$SO_2R^{12}$, —$OR^{13}$, -halo, —CN, —$CF_3$, aminoalkyl-, —S(O)$R^{14}$, and alkyl; heterocycloalkyl; heteroaryl; substituted aryl substituted with 1 to 3 substituents independently selected from the group consisting of alkyl, —$CF_3$, F, Cl, and Br; alkylamino-; heterocycloalkyl-alkyl-amino-; alkylaminoalkylamino-; —NHC(O)$OR^{15}$; —NHC(O)$NR^{16}R^{17}$; —C(O)$NR^{16}R^{17}$; and substituted heteroaryl substituted with 1 to 3 substituents selected from the group consisting of alkyl, halo, CN, $NH_2$, —NH($C_1$-$C_6$ alkyl), —N($C_1$-$C_6$ alkyl)$_2$ wherein each alkyl is independently selected, —$CF_3$, and substituted aryl substituted with 1 to 3 substituents independently selected from the group consisting of —S(O)$_2R^{15}$ and —CN;

wherein $R^{12}$, $R^{13}$, $R^{14}$, $R^{15}$, $R^{16}$, and $R^{17}$ are each independently selected from the group consisting of $C_1$-$C_6$alkyl, dialkylamino comprising independently selected $C_1$-$C_6$ alkyl, —$NH_2$, alkylamino, heterocycloalkyl, and substituted heterocycloalkyl substituted with one to two substituents independently selected from the group consisting of —C(O)O($C_1$-$C_6$ alkyl) and —$C_1$-$C_6$ alkyl.

In some compounds, $A_4$ is N. In some compounds, $A_3$ is $NR^8$ and $A_4$ is N. In some compounds, at least one of $A_3$ and $A_3'$ is O or S. In some compounds, one or both of $A_1$ and $A_1'$ is N. In some compounds, $A_5$ and $A_5'$, if present, are each independently $CR^{10}$, and $A_6$ and $A_6'$, if present, are each independently $CR^{11}$. In some compounds, at least one of $A_1$, $A_2$, $A_1'$, and $A_2'$ is N. In some compounds, one or both of $A_2$ and $A_2'$ is CH, $A_3$ is NH, $A_4$ is N, $A_5$ is CH, and $A_6$ is CH.

In some compounds, one or both of $A_2$ and $A_2'$ is CH, one or both of $A_3$ and $A_3'$ is NH, one or both of $A_4$ and $A_4'$ is N, one or both of $A_5$ and $A_5'$ is CH, and one or both of $A_6$ and $A_6'$ is CH. In some compounds, Q is piperazine-1,4-diyl; 2,5-diazabicyclo[2.2.1.]heptane-2,5-diyl; 2,5-diazabicyclo[2.2.2]octane-2,5-diyl; 1,4-diazepane-1,4-diyl; $N^1,N^2$-dialkylethane-1,2-diamine-$N^1,N^2$-diyl; $N^1,N^3$-dialkylpropane-1,3-diamine-$N^1,N^3$-diyl; 1,4-diaminoanthracene-9,10-dione-1,4-diyl; $C_6$ arene-1,4-diamine-$N^1,N^4$-diyl wherein the arene is substituted with one to four substituents in the 2, 3, 5, or 6 positions and each substituent is independently selected from the group consisting of —C(O)O($C_1$ to $C_6$)alkyl, OH, O($C_1$ to $C_6$)alkyl, ($C_1$ to $C_6$)alkyl, $CF_3$, F, Cl, and Br; or substituted piperazine-1,4-diyl wherein the piperazine is substituted with one to eight substituents in the 2, 3, 5, or 6 positions and each substituents is independently selected from the group consisting of ($C_1$ to $C_6$)alkyl, aryl, aryl($C_1$ to $C_6$)alkyl, C(O)OH, and C(O)O($C_1$ to $C_6$)alkyl. In some compounds, $R^1$, $R^{1'}$, $R^2$, $R^{2'}$, $R^3$, $R^{3'}$, $R^4$, $R^{4'}$, $R^5$, $R^6$, $R^7$, $R^8$, $R^9$, $R^{10}$ and $R^{11}$ if present, are in each instance independently selected from the group consisting of hydrogen, alkyl, halo, trifluoromethyl, dialkylamino wherein each alkyl is the same or different, —$NH_2$, alkylamino, aryl, and arylalkyl.

Other compounds suitable for use in the treatments described herein include compounds comprising formula A-B-C, or a pharmaceutically acceptable salt or ester thereof, wherein:

A is:

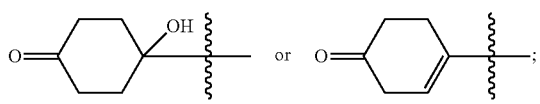

B is:

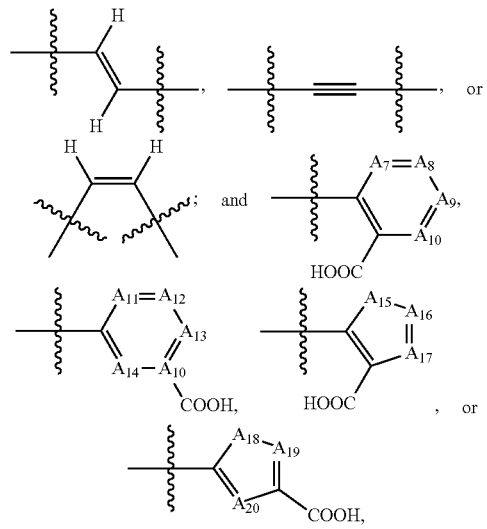

wherein:

$A_7$, $A_8$, $A_9$, $A_{10}$, $A_{11}$, $A_{12}$, $A_{13}$, and $A_{1a}$ are each independently selected from CH, $CR^{18}$, and N;

$A_{15}$, $A_{16}$, $A_{17}$, $A_{18}$, $A_{19}$, and $A_{20}$ are each independently selected from CH, $CR^{19}$, N, $NR^{20}$, O, and S, with the proviso that only one of $A_{15}$, $A_{16}$, and $A_{17}$ can be N, $NR^{20}$, O, or S and only one of $A_{18}$, $A_{19}$, and $A_{20}$ can be N, $NR^{20}$, O, or S;

$R^{18}$ and $R^{19}$ are each independently selected from $C_1$-$C_6$ alkyl; $C_1$-$C_6$ dialkylamino, wherein each $C_1$-$C_6$ alkyl is independently selected; —$NH_2$; alkylamino; heterocycloalkyl; and substituted heterocycloalkyl, wherein the substituted heterocycloalkyl is substituted with one to two substituents independently selected from the group consisting of: —C(O)O($C_1$-$C_6$ alkyl) and $C_1$-$C_6$ alkyl; wherein in compounds with more than one $CR^{18}$ each $R^{18}$ is independently selected, and in compounds with more than one $CR^{19}$ each $R^{19}$ is independently selected; and $R^{20}$ is $C_1$-$C_6$ alkyl.

Other compounds suitable for use in the treatments described herein include any FA compound disclosed in or encompassed by any formulas disclosed in U.S. Pat. No. 9,556,146. U.S. Pat. No. 9,556,146 is incorporated herein by reference in its entirety.

The invention provides methods of treating a condition in an animal with any one or more of the compounds described herein. The methods may comprise administering an effective amount of one or more of the compounds described herein to the animal.

The invention also provides methods of generating a prepared cell from a precursor cell with the compounds described herein. The methods may comprise contacting the precursor cell, in vitro, with one or more of the compounds described herein to generate the prepared cell.

The invention also provides isolated cells generated by contacting a precursor cell, in vitro, with one or more of the compounds described herein to generate a prepared cell.

The invention also provides methods of treating a condition in an animal with a prepared cell as described herein. The methods comprise administering the prepared cell to the animal in an amount sufficient to treat the condition.

The conditions treatable with the compounds or cells described herein may include an infectious disease, a hyperproliferative disorder, an inborn error of metabolism, a chronic immunometabolic disease, an autoimmune disease, organ transplant rejection, an inflammatory disorder, and chronic pain. In some versions, the infectious disease comprises a bacterial disease. In some versions, the bacterial disease comprises *C. difficile* infection. In some versions, the hyperproliferative disorder comprises cancer. In some versions, the cancer comprises a cancer of the gastrointestinal tract. In some versions, the cancer of the gastrointestinal tract comprises colorectal cancer. In some versions, the hyperproliferative disorder comprises familial adenomatous polyposis. In some versions, the inborn error of metabolism comprises a glycogen storage disease. In some versions, the glycogen storage disease comprises Andersen disease. In some versions, the chronic immunometabolic disease comprises cardiovascular disease. In some versions, the cardiovascular disease comprises atherosclerosis. In some versions, the chronic immunometabolic disease comprises hypertension. In some versions, the autoimmune comprises at least one of lupus and multiple sclerosis. In some versions, the autoimmune disease comprises a cancer-immunotherapy-induced autoimmune disease. In some versions, the cancer-immunotherapy-induced autoimmune disease comprises a cancer immunotherapy-induced rheumatic disease. In some versions, the inflammatory disorder comprises acute colonic diverticulitis. In some versions, the inflammatory disorder comprises radiation-induced inflammation of the gastrointestinal tract. In some versions, the radiation-induced inflammation of the gastrointestinal tract comprises at least one of radiation proctitis, radiation enteritis, and radiation proctosigmoiditis. In some versions, the chronic comprises fibromyalgia. In some versions, the condition comprises inflammatory bowel disease, such as Crohn's disease or ulcerative colitis.

The objects and advantages of the invention will appear more fully from the following detailed description of the preferred embodiment of the invention made in conjunction with the accompanying drawings.

BRIEF DESCRIPTION OF THE DRAWINGS

FIG. 3C, panels F-H). Statistical significance by treatment group (n=10) marked by * (P<0.05) and ** (P<0.01).

FIGS. 1A-C. Effects of BT-11 in reducing inflammation, mortality, and severity of *C. difficile* infection.

DETAILED DESCRIPTION OF THE INVENTION

Figure 1A:
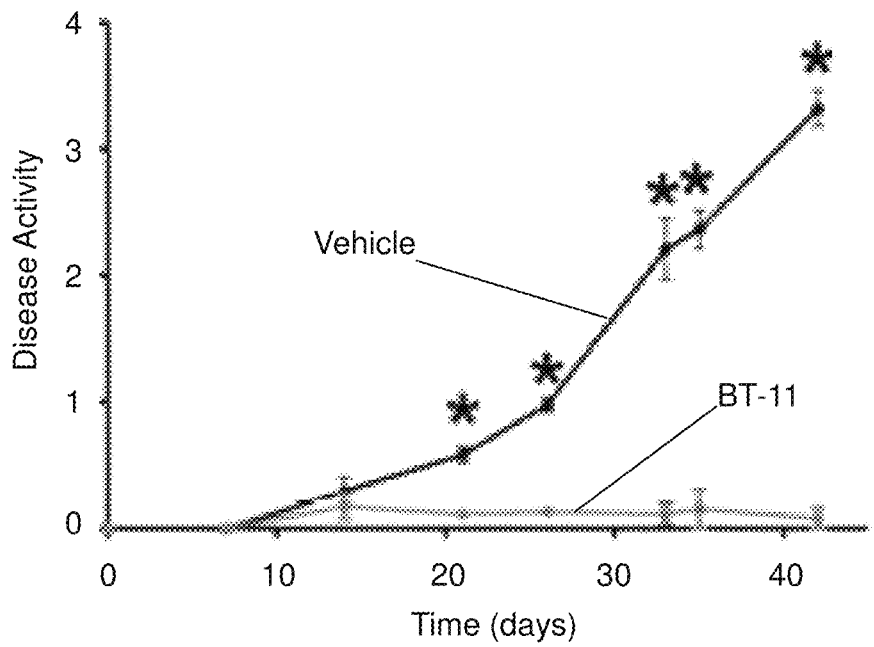
FIGS. 1A-1F. BT-11 suppresses disease development in Mdr1a-/- model of colitis. BT-11 decreases disease activity index (FIG. 1A, panel A). Representative photomicrographs of H&E stained colonic sections at ten weeks of age in vehicle (FIG. 1A, panel B) and BT-11 treated (FIG. 1A, panel C) animals. Immunophenotyping of Th1 (CD3+CD4+CD8-NK1.1- Tbet+ IFNγ+), Th17 (CD3+CD4+CD8-NK1.1- RORγT+IL17+), and Treg (CD3+CD4+CD25+FOXP3+IL10+) cells, respectively in the colonic lamina propria (FIG. 1B, panels D-F) and mesenteric lymph nodes (FIG. 1C, panels G-I) at ten weeks of age. qRT-PCR of whole colon of Ifnγ (FIG. 1D, panel J), Il17a (FIG. 1D, panel K), Mcp1 (FIG. 1E, panel L), Tnfa (FIG. 1E, panel M), Lancl2 (FIG. 1F, panel N), and Il6 (FIG. 1F, panel 0) normalized to β-actin. Statistical significance by treatment group (n=10) marked by * (P<0.05) and ** (P<0.01).
Figure 1A:
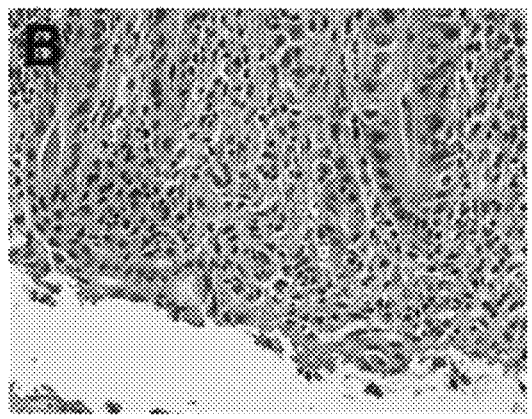
Figure 1A:
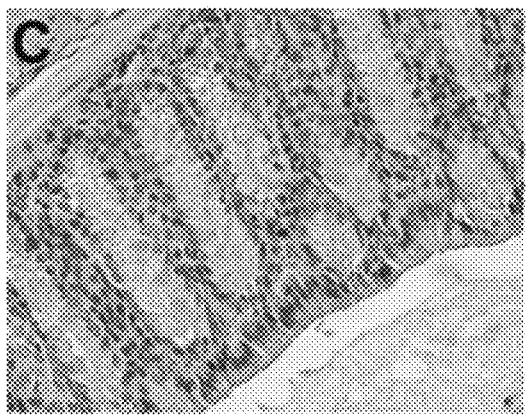

The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above except that it contains one or more double bonds. Examples of alkenyl groups include vinyl, 2-propenyl, crotyl, 2-isopentenyl, 2-(butadienyl), 2,4-pentadienyl, 3-(1, 4-pentadienyl), etc., and higher homologs and isomers.

The term "alkynyl" means an alkyl or alkenyl group as defined above except that it contains one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

Typically, alkyl, alkenyl, alkynyl, alkylene, alkenylene, and alkynylene groups will have from 1 to 24 carbon atoms. Those groups having 10 or fewer carbon atoms are preferred in the present invention. The term "lower" when applied to any of these groups, as in "lower alkyl" or "lower alkylene," designates a group having 10 or fewer carbon atoms.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, and alkynylene moieties. Additionally, these groups may be pendent from, or integral to, the carbon chain itself.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., $CF_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "halogen" or "halo" is used herein to refer to fluorine, bromine, chlorine, and iodine atoms.

The term "hydroxy" is used herein to refer to the group —OH.

The term "amino" is used to designate NRR', wherein R and R' are independently H, alkyl, alkenyl, alkynyl, aryl, or substituted analogs thereof. "Amino" encompasses "alkylamino," denoting secondary and tertiary amines, and "acylamino" describing the group RC(O)NR'.

In the course of the methods of the present invention, a therapeutically effective amount of compounds of the invention can be administered to an animal, including mammals and humans, in many ways. While in the preferred embodiment, the compounds of the invention are administered orally or parenterally, other forms of administration such as through medical compounds or aerosols are also contemplated.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

The compounds of the present invention may also be administered rectally. For rectal administration, a suppository may be used. The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For parenteral administration, the compounds of the present invention may be administered by injection. For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may be used. Included among these is the non-limiting example of water.

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of for example, dichlorofluoromethane, propane or nitrogen may be used as the spraying agent.

The compounds of the invention may be administered to an animal, including mammals and humans, in need thereof as a pharmaceutical composition, such as tablets, capsules, solutions, or emulsions. Administration of other forms of the compounds described in this invention, including but not limited to esters thereof, pharmaceutically-suitable salts thereof, metabolites thereof, structurally related compounds thereof, analogs thereof, and combinations thereof, in a single dose or a multiple dose, are also contemplated by the present invention.

The terms "preventing," "treating," "protecting," or "ameliorating" and similar terms used herein, include prophylaxis and full or partial treatment. The terms may also include reducing symptoms, ameliorating symptoms, reducing the severity of symptoms, reducing the incidence of the disease, induction of remission, maintenance of remission, or any other change in the condition of the patient, which improves the therapeutic outcome.

The new compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. It is preferably from about 0.00001 g to about 20 g (more preferably 0.01 g to 1 g, such as 0.05 g to 0.5 g) of compound per day. Suitable compositions can be formulated accordingly. Those of skill in the art of dosing of biologically active agents will be able to develop particular dosing regimens for various subjects based on known and well-understood parameters.

A preferred composition according to the invention is a pharmaceutical composition, such as in the form of tablets, pills, capsules, caplets, multiparticulates (including granules, heads, pellets and micro-encapsulated particles), powders, elixirs, syrups, suspensions, hydrogels such as inflammation-targeting hydrogels, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Preferably the unit dosage of compounds described in the present invention is from 1 mg to 1000 mg (more preferably from 50 mg to 500 mg). The excipients used in the preparation of these compositions are the excipients known in the art. Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. Preferably, the unit dosage of compounds in the food supplements is from 1 mg to 1000 mg (more preferably from 50 mg to 500 mg).

In general, the term carrier may be used throughout this application to represent a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention. Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans.

For instance, an amount of a compound effective to treat or prevent the conditions described herein in an animal can range from 0.1-10,000 mg/kg/day. A preferred effective amount of compound is 1 to 5,000 mg/kg/day, with a more preferred dose being 2 to 100 mg/kg/day. The upper limit of the effective amount to be administered is not critical, as the compounds are non-toxic as our toxicology data demonstrates. The effective amount of compound is most effective in treating or preventing the conditions described herein in an animal when administered to the animal for periods ranging from about 7 to 100 days, with a preferred period of 15 to 50 days, and a most preferred period of 30 to 42 days.

An amount of compound most effective in preventing over-activation or dysregulation of the immune system leading to autoimmune, inflammatory or metabolic diseases can range from 0.1 to 500 mg/kg/day, with a preferred dose of 1 to 150 mg/kg/day.

When the effective amount of the compound of the present invention is administered in a therapeutic, medical, or veterinary composition, the preferred dose ranges from about 0.01 to 2.0% wt/wt to drug product.

In certain other embodiments, the present invention provides for use of LANCL2-binding compounds and also structurally related compounds, such as a compound selected from the group consisting the compound, esters thereof, pharmaceutically suitable salts thereof, metabolites thereof, structurally related compounds thereof, or combinations thereof in the treatment and prevention of immunometabolic disease.

In addition, in general, the present invention relates to the prevention of defects or restoration of homeostasis in regard to pathways of immunometabolism that help intercept autoimmune, inflammatory, metabolic or infectious diseases, wherein the relevant pathways include glucose metabolism and storage, fatty acid metabolism and storage, amino acid metabolism and storage, calcium flux, cyclic AMP metabolism, inflammatory pathways such as TLR and NLR signaling or NF-κ3 signaling that control production of pro-inflammatory cytokines (tumor necrosis factor alpha, interferon gamma, interleukin-6 and monocyte chemoattractant protein 1), and regulatory pathways such as FOXP3 activity or IL-10 signaling. The effect results from the exposure of compound to various cells types in the body that induces a biological effect. The cells may include but are not limited to those from GI tract tissues, immune cells (i.e. macrophages, monocytes, lymphocytes), muscle cells, endothelial cells or epithelial cells. In certain embodiments, the invention provides for treating subjects with a compound of the invention, for example administered orally, to reduce or prevent inflammation related to infectious disease, such as *C. difficile* infection.

When practiced, the methods of the invention can be by way of administering the compounds to a subject via any acceptable administration route using any acceptable form, as is described above, and allowing the body of the subject to distribute the compounds to the target cell through natural processes. As is described above, administering can likewise be by direct injection to a site (e.g., organ, tissue) containing a target cell (i.e., a cell to be treated) or culturing cells that will be used for cell therapy with the compounds before injecting the cells back in the body.

Furthermore, administering can follow any number of regimens. It thus can comprise a single dose or dosing of experimental compound, or multiple doses or dosings over a period of time. Accordingly, treatment can comprise repeating the administering step one or more times until a desired result is achieved. In certain embodiments, treating can continue for extended periods of time, such as weeks, months, or years. Those of skill in the art are fully capable of easily developing suitable dosing regimens for individuals based on known parameters in the art. The dosage amounts for compounds of the invention may be used in the methods of these embodiments of the invention. For the treatment of immunometabolic disease, it is preferred that the compounds be administered at amounts of about 0.001 mg/day to 9,000 mg/day.

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation in the afflicted site or concentration of affected metabolite or signal transducer. With patients not experiencing active symptoms, the change one might look for may involve immune cell parameters such as TNFα expression in immune-cells or the percent of regulatory T-cells in the blood or metabolic parameters such as glucose uptake by cells or amount of glycogen within cells. Suitable amounts are disclosed herein, and additional suitable amounts can be identified by those of skill in the art without undue or excessive experimentation, based on the amounts disclosed herein.

In view of the above methods, it should be evident that the present invention provides immunometabolic treatment through LANCL2-binding compound for use in contacting cells, such as in treating cells of a subject. The above discussion focuses on the use of the compounds of the present invention as part of a composition for use in what could generally be considered a pharmaceutical or medical setting.

The compounds described in this invention for the treatment of immunometabolic disease and other conditions described may be formulated as a pharmaceutical, nutritional composition, functional food composition, dietary aid or in cell therapy, as are described in greater detail above.

As an alternative or in addition to the methods of treating conditions by administering the compounds directly, the conditions can be treated with prepared cells generated from precursor cells with the compounds. The conditions that can be treated include any condition described herein or in U.S. Pat. No. 9,556,146. The compounds used in the treatment can include any compound disclosed herein or encompassed by any formulas disclosed herein, or any compound disclosed in or encompassed by any formulas disclosed in U.S. Pat. No. 9,556,146.

The term "precursor cell" is used herein to refer generally to any cell that serves as a starting cell that is treated to generate a prepared cell. The cell may be a cell upstream in a differentiation lineage leading to the prepared cell, such as a stem cell, a progenitor cell, or a "precursor cell" (as the term is used in the art to refer to an intermediate between a stem cell and a differentiated cell) with, e.g., totipotent, multipotent or unipotent properties, but does not necessarily have to be so. Accordingly, in some versions, generating the prepared cell from the precursor cell involves differentiating the precursor cell into the prepared cell. In other versions, generating the prepared cell from the precursor cell merely involves inducing changes such as gene expression changes.

The prepared cells can be generated from precursor cells by contacting the precursor cells in vitro with one or more of the compounds of the invention to thereby generate the prepared cells. The terms "in vitro" and "ex vivo" are used interchangeably herein in contrast to "in vivo" and refer to a state of being outside of a living organism.

The precursor and/or prepared cells of the invention may comprise immune cells. Exemplary immune cells include granulocytes, mast cells, monocytes, macrophages, neutrophils, dendritic cells, natural killer cells, T cells, and B cells, among others. Exemplary granulocytes include basophils, eosinophils, and neutrophils.

The precursor and/or prepared cells of the invention may comprise white blood cells (leukocytes). Exemplary white blood cells include neutrophils, eosinophils (acidophiles), basophils, lymphocytes, and monocytes.

The precursor and/or prepared cells of the invention may comprise peripheral blood mononuclear cells (PBMCs) or lamina propria mononuclear cells (LPMCs). Exemplary PBMCs and LPMCs include lymphocytes (T cells, B cells, NK cells) and monocytes. The precursor and/or prepared cells of the invention may comprise T cells. T cells are divided into two broad categories: CD8+ T cells or CD4+ T cells, based on which protein is present on the cell's surface. T cells carry out multiple functions, including killing infected cells and activating or recruiting other immune cells. CD8+ T cells also are called cytotoxic T cells or cytotoxic lymphocytes (CTLs). They are crucial for recognizing and removing virus-infected cells and cancer cells. The major CD4+ T-cell subsets are naïve CD4+ T cells, TH1 cells, TH2 cells, TH17 cells, and Treg cells, with "TH" referring to "T helper cell." Naïve CD4+ T cells are T cells that are not differentiated into any of TH 1 cells, TH2 cells, TH17 cells, and Treg cells. Regulatory T cells (Tregs) monitor and inhibit the activity of other T cells. They prevent adverse immune activation and maintain tolerance, or the prevention of immune responses against the body's own cells and antigens. In some versions, the precursor cells comprise naïve CD4+ T cells, and the prepared cells comprise Treg cells.

Generating the prepared cells from the precursor cells may comprise contacting an amount of one or more compounds of the invention for a time effective to induce a compound-dependent difference in the prepared cells with respect to the precursor cells. As used herein, "compound-dependent difference" refers to a difference in the prepared cell with respect to the precursor cell arising from contacting the precursor cell with one or more compounds of the invention. Compound-dependent differences can be determined by contacting cells with media in the presence or absence the one or more compounds of the invention, wherein the compound-dependent differences are characteristics that appear only with the cells contacted with media in the presence of the one or more compounds of the invention. The compound-dependent differences may be differences not only in kind but also of degree.

The compound-dependent difference in the prepared cells may include a difference in gene expression. Unless explicitly stated otherwise, "gene expression" is used broadly herein to refer to any or all of transcription or translation. Thus, a difference in gene expression can be a difference in mRNA production, a difference in protein production, or both. Unless explicitly stated otherwise, the gene having differential expression may be identified herein by referring to the protein produced from the gene (e.g., FOXP3) or by referring to the gene itself (e.g., Lag3). In various versions of the invention, the compound-dependent differences in gene expression may comprise one or more of an increase in expression of IL-10 or an ortholog thereof, an increase in expression of FOXP3 or an ortholog thereof, a decrease in expression of TNFα or an ortholog thereof, a decrease in expression of IFNγ or an ortholog thereof, a decrease in expression of Tbet or an ortholog thereof, an increase in expression of Lag3 or an ortholog thereof, an increase in expression of Socs2 or an ortholog thereof, an increase in expression of Irf7 or an ortholog thereof, an increase in expression of P2rx7 or an ortholog thereof, an increase in expression of Capn3 or an ortholog thereof, an increase in expression of Ikzf2 or an ortholog thereof, an increase in expression of Stat5a or an ortholog thereof, an increase in expression of Pten or an ortholog thereof, an increase in expression of Foxo1 or an ortholog thereof, and/or an increase in expression of Phlpp1 or an ortholog thereof. The orthologs may include orthologs in animal species. The orthologs may include orthologs in mammalian species. The orthologs (such as for the mouse genes named above) may include orthologs in primates. The orthologs (such as for the mouse genes named above) may include orthologs in humans.

The compound-dependent difference in the prepared cells may include other detectable differences, such as an increase in phosphorylation of STAT5a or an ortholog thereof, an increase in FOXO1 phosphorylation or an ortholog thereof, and/or an increase in pyruvate kinase activity.

In generating the prepared cells, the precursor cells may be contacted with amounts of the compound from about 100 nM, about 10 nM, about 1 nM or less to about 1 μM, about 10 μM, about 100 μM, about 1 mM or more. The precursor cells may be contacted with the compound for a time from about 12 hours, 6 hours, 1 hour, about 30 minutes, or less to about 24 hours, about 48 hours, about 72 hours or more.

In some versions, the PBMCs or LPMCs at large are contacted with the compound of the invention. The PBMCs or LPMCs can be isolated from an animal. In some versions, subtypes of PBMCs or LPMCs, such as T cells, can be isolated from the PBMCs or LPMCs and then contacted with the compound of the invention. In some versions, the PBMCs or LPMCs are contacted with the compound of the invention, and then subtypes of cells, such as T cells or a particular type of T cells are isolated therefrom. Methods for isolating PBMCs, LPMCs, and subtypes thereof are known in the art. See, e.g., Majowicz et al. 2012 (Majowicz A, van der Marel S, to Velde A A, Meijer S L, Petry H, van Deventer S J, Ferreira V. Murine CD4+CD25− cells activated in vitro with PMA/ionomycin and anti-CD3 acquire regulatory function and ameliorate experimental colitis in vivo. *BMC Gastroenterol.* 2012 Dec. 3; 12:172) and Canavan et al. 20016 (Canavan J B, Scottà C, Vossenkämper A, Goldberg R, Elder M J, Shoval I, Marks E, Stolarczyk E, Lo J W, Powell N, Fazekasova H, Irving P M, Sanderson J D, Howard J K, Yagel S, Afzali B, MacDonald T T, Hernandez-Fuentes M P, Shpigel N Y, Lombardi G, Lord G M. Developing in vitro expanded CD45RA+ regulatory T cells as an adoptive cell therapy for Crohn's disease. *Gut.* 2016 April; 65(4):584-94). Subsets of PMBCs, for example, can be isolated with anti-CD3 antibodies and anti-CD28 antibodies. Anti-CD3 antibodies and anti-CD28 antibodies can be provided in the form of anti-CD3/anti-CD28 beads, such as Human T-Activator CD3/CD28 DYNABEADS® from ThermoFisher Scientific (Waltham, MA).

Generating the prepared cells can comprise differentiating the prepared cells from the precursor cells. For example, prepared cells such as Treg cells can be differentiated from precursor cells such as naïve CD4+ T cells. Such differentiating can comprise contacting the precursor cells with differentiating factors in addition to one or more of the compounds of the invention. Various differentiating factors may include all-trans-retinoic acid, TGF-β, phorbol myristate acetate, ionomycin, rapamycin, and/or IL-2. In some versions, the differentiating can comprise expanding the proportion of Treg cells in the prepared cells with respect to the portion in the precursor cells.

The precursor and prepared cells of the invention can be isolated cells. The term "isolated" or "purified" means a material that is removed from its original environment, for example, the natural environment. A material is said to be "purified" when it is present in a particular composition in a higher or lower concentration than the concentration that exists prior to the purification step(s).

Treating the condition with the prepared cells of the invention can comprise administering the cells to the animal in an amount sufficient to treat the condition. The prepared cells can be administered using any route or method described above for the compounds, including parenterally or enterally. Non-limiting forms of parenteral administration include injection or infusion. The prepared cells can be injected or infused directly into the bloodstream or other parts of the body. Non-limiting forms of enteral administration include oral and rectal administration, such that the prepared cells enter the gastrointestinal tract. The prepared cells may be autologous to the treated animal (i.e., generated from a cell taken from the same animal that the prepared cell is used to treat) or heterologous to the treated animal (i.e., generated from a different animal that the prepared cell is used to treat). A cell prepared as described above can be used in a method of treating any of the conditions described herein. Exemplary conditions include intestinal inflammation. Exemplary types of intestinal inflammation include inflammatory bowel disease. Exemplary types of inflammatory bowel disease include Crohn's disease and ulcerative colitis.

In one embodiment of the invention, the method of treating immunometabolic disease comprises treatment without causing discernable side-effects, such as significant weight gain, systemic immune suppression, cushingoid appearance, osteopenia/osteoporosis, cellular toxicity or pancreatitis that is common of currently available treatments (i.e. statins, antibiotics, corticosteroids, doxorubicin, methotrexate). That is, it has been found that the method of treating according to the present invention, which provides the treatment effect, at least in part, by affecting the expression and/or activation of LANCL2 and/or other immunometabolic pathways in some cells, provides the beneficial effect without causing a significant gain in weight, for example by fluid retention, in the subject being treated, as compared to other similar subjects not receiving the treatment.

As such, the immunometabolic methods of the present invention can provide treatments for reducing inflammation by affecting the metabolism of immune cells. The methods can reduce inflammation systemically (i.e., throughout the subject's body) or locally (e.g., at the site of administration or the site of inflammatory cells, including but not limited to T cells and macrophages). In treating or preventing inflammation through immunometabolism, one effect that may be observed is a shift in the metabolism of glucose. In particular, the shift may be from the production of lactate from pyruvate towards the entrance into the tricarboxylic acid cycle that is tied with immunoinflammatory actions. More specifically, this shift in metabolism can be associated with an increase in the proportion of CD4+CD25+ FOXP3+ or other regulatory CD4+ T-cells relative to effector CD4+ T-cells such as IL17+Th17 cells or IFNγ+Th1 cells. Another observed effect may be decreased cellular proliferation resulting from the combination of decreased anaerobic metabolism and increased immune checkpoint pathways. Another effect of shifts in metabolism triggered therapeutically may be decreased expression of inflammatory chemokines such as MCP-1, IL-8, or CXCL9 resulting from altered processing and storage of fatty acids. The methods can thus also be considered methods of affecting or altering the immune response of a subject to whom the therapy is administered, thereby intercepting inflammation, disease and pathology.

The invention provides methods of inhibiting inflammation in the GI tract, wherein the relevant components include the stomach, small intestine, large intestine, and rectum.

The invention provides methods of treating or preventing a subject suffering from IBD, or otherwise healthy individuals, perhaps with a genetic predisposition for Crohn's Disease or ulcerative colitis, from developing IBD. The methods may also involve treating those with a remissive form of IBD. According to the invention, the term "a subject suffering from IBD" is used to mean a subject (e.g., animal, human) having a disease or disorder showing one or more clinical signs that are typical of IBD. In general, the method of treating or preventing according to this aspect of the invention comprises administering to the subject an amount of compound or cell therapy that is effective in treating or preventing one or more symptoms or clinical manifestations of IBD, or in preventing development of such symptom(s) or manifestation(s).

Thus, according to the methods of the invention, the invention can provide methods of treatment of IBD, inflammation associated with enteric infection and inflammation associated with autoimmune diseases. The methods of treatment can be prophylactic methods. In certain embodiments, the method is a method of treating IBD, inflammation associated with enteric infection and inflammation associated with autoimmune diseases. In other embodiments, the method is a method of preventing IBD. In embodiments, the method is a method of preventing a remissive form of IBD from becoming active. In still other embodiments, the method is a method of improving the health status of a subject suffering from IBD, inflammation associated with enteric infection and inflammation associated with autoimmune diseases. Organisms causing gastroenteric infections include but are not limited to: *Escherichia coli, Shigella, Salmonella*, pathogenic *Vibrios, Campylobacter jejuni, Yersina enterocolitica, Toxoplasma gondii, Entamoeba histolytica* and *Giardia lamblia*. Accordingly, in certain embodiments, the invention provides a method of protecting the health, organs, and/or tissues of a subject suffering from IBD, inflammation associated with enteric infection and inflammation associated with autoimmune diseases or at risk from developing IBD, inflammation associated with enteric infection and inflammation associated with autoimmune diseases.

In one embodiment of the invention, the method of treating IBD comprises treating IBD without causing discernable side-effects, such as significant weight gain, systemic immune suppression, cushingoid appearance, osteopenia/osteoporosis, or pancreatitis that is common of currently available IBD treatments (i.e. corticosteroids, tumor necrosis factor alpha inhibitors). That is, it has been found that the method of treating according to the present invention, which provides the treatment effect, at least in part, by affecting the expression and/or activation of LANCL2 in some cells, provides the beneficial effect without causing a significant gain in weight, for example by fluid retention, in the subject being treated, as compared to other similar subjects not receiving the treatment.

As such, the methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating the intestine. Another may be the increase in regulatory immune cell populations, such as $CD4^+CD25^+$ $FoxP3^+$ regulatory T-cells, or an increase in regulatory properties of lymphocytes or macrophages (e.g. increased interleukin 4 (IL-4) or IL-10 or decreased TNF-α and IL-6). Another may be the decreased presence of inflammatory genes and/or adhesion molecules. The methods can thus also be considered methods of affecting or altering the immune response of a subject to whom the therapy is administered. The subject may have inflammatory bowel disease or another condition in which the immunomodulation of T cells or downregulation of cellular adhesion molecules is a desired outcome.

The invention also provides methods of treating an infectious disease with the compounds or cells described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the familyhepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracis, Bacillus cereus, Bordetella pertussis, Borrelia burgdorferi, Brucella abortus, Brucella canis, Brucella melitensis, Brucella suis Campylobacter jejuni Chlamydia pneumoniae, Chlamydia trachomatis, Chlamydophila psittaci, Clostridium botulinum, Clostridium diffacile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus* pyo genes, *Treponema pallidum, Vibrio cholerae, Yersinia pestis, Yersinia enterocolitica, Yersinia pseudotuberculosis,* and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause *pneumocystis* pneumonia; and fungi of the genus *Sporothrix*, such as *Sporothrix schenckii*, which cause sporotrichosis.

The invention also provides methods of treating hyperproliferative disorders with the compounds or cells described herein. Hyperproliferative disorders include conditions involving uncontrolled growth of cells, such as cancers or conditions involving the growth of tumors, adenomas, or polyps. Non-limiting examples of hyperproliferative disorders include colorectal cancer, familial adenomatous polyposis (PAP), throat cancer, thyroid cancer, gastric cancer, cancers of the gastrointestinal tract, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, hypereosinophilic syndrome, mastocytosis, among others.

The invention also provides methods of treating an inborn error of metabolism with the compounds or cells described herein. Non-limiting examples of inborn errors of metabolism include Wilson disease, Andersen disease or other glycogen storage diseases, Cystinuria, Fabry disease, adult-onset citrullinemia type II, Zellweger syndrome, branched-chain ketoaciduria, Lesch-Nyhan syndrome, Niemann-Pick disease, Fanconi-Bickel disease, von Gierke's disease, hereditary fructose intolerance, phenylketonuria, medium chain acyl-CoA dehydrogenase deficiency, among others.

The invention also provides methods of treating a chronic immunometabolic disease with the compounds or cells described herein. Non-limiting examples of chronic immunometabolic diseases include cardiovascular disease, such as atherosclerosis, coronary artery disease, peripheral artery disease, pulmonary heart disease, endocarditis, myocarditis, and hypertension.

The invention also provides methods of treating an autoimmune disease, such as an inflammatory autoimmune disease, with the compounds or cells described herein. Non-limiting examples of autoimmune diseases include inflammatory bowel disease (IBD) (e.g., Crohn's disease and ulcerative colitis), lupus, systemic lupus, rheumatoid arthritis, type 1 diabetes, psoriasis, multiple sclerosis, and cancer-immunotherapy-induced autoimmune diseases among others. Non-limiting examples of cancer-immunotherapy-induced autoimmune diseases include cancer immunotherapy-induced rheumatic diseases.

The invention also provides methods of treating chronic inflammatory diseases with the compounds or cells described herein. Non-limiting examples of chronic inflammatory diseases includes metabolic syndrome, obesity, pre-diabetes, cardiovascular disease, and type 2 diabetes, among others.

The invention also provides methods of treating inflammatory disorders such as acute colonic diverticulitis and radiation-induced inflammation of the gastrointestinal tract with the compounds or cells described herein. Non-limiting examples of radiation-induced inflammation of the gastrointestinal tract include radiation proctitis, radiation enteritis, and radiation proctosigmoiditis.

The invention also provides methods of treating diabetes with the compounds or cells described herein, including type 1 diabetes, type 2 diabetes, and other types of diabetes. The term "diabetes" or "diabetes mellitus" is used to encompass metabolic disorders in which a subject has high blood sugar (i.e., hyperglycemia). Hyperglycemic conditions have various etiologies, such as the pancreas does not produce enough insulin, or cells do not respond to the insulin that is produced. There are several recognized sub-types of diabetes. Type 1 diabetes is characterized by the complete failure of the body to produce insulin or the failure of the body to produce enough insulin. Type 2 diabetes generally results from insulin resistance, a condition in which cells fail to use insulin properly. Type 2 diabetes sometimes co-presents with an insulin deficiency. Gestational diabetes occurs when pregnant women without a previous diagnosis of diabetes develop hyperglycemia. Less common forms of diabetes include congenital diabetes (due to genetic defects relating to insulin secretion), cystic fibrosis-related diabetes, steroid diabetes induced by high doses of glucocorticoids, and several forms of monogenic diabetes (including maturity onset diabetes of the young). Monogenic diabetes encompasses several hereditary forms of diabetes caused by mutations in a single, autosomal dominant gene (as contrasted to more complex, polygenic etiologies resulting in hyperglycemia).

The invention also provides methods of treating chronic pain with the compounds or cells described herein. Non-limiting examples of chronic pain diseases include fibromyalgia, nerve damage, migraine headaches, back pain, abdominal pain, among others.

The invention also provides methods of treating additional conditions with the compounds or cells described herein. These include chronic inflammatory diseases such as chronic granulomatous disease, graft versus host disease, and tumor necrosis factor receptor associated periodic syndrome; muscle wasting, such as amyotrophic lateral sclerosis, Duchenne muscular dystrophy, scoliosis, and progressive muscular atrophy; and others.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

Molecular Modeling and LANCL2 Binding Examples

Examples showing the binding of BT-11 and related compounds to LANCL2 are provided by U.S. Pat. No. 9,556,146, which is incorporated herein by reference in its entirety. The predicted and actual binding (via surface plasmon resonance (SPR) of BT-11 and other related compounds are shown in Tables 1A and Tables 1B.

TABLE 1A

Predicted and Actual SPR Binding of BT-11 and Related Compounds

| Example No. | Compound name | Structure | Predicted Binding Affinity to LANCL2 | SPR Affinity to LANCL2 (Kd) |
|---|---|---|---|---|
| 1 | BT-11 | 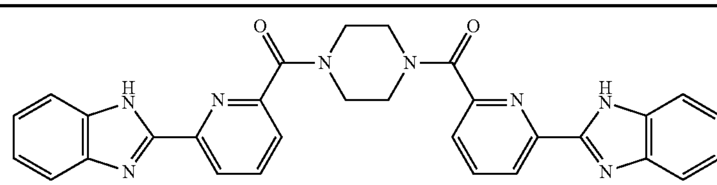 | −11.2 | 7.7 |
| 2 | BT-12 | 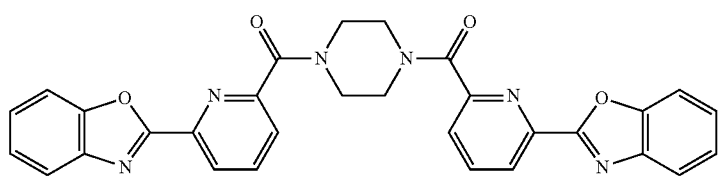 [SMILES: O=C(c1cccc(-c2nc3ccccc3o2)n1)N1CCN(C(=O)c2cccc(-c3nc4ccccc4o3)n2)CC1] | −10.9 | |
| 3 | BT-14 | 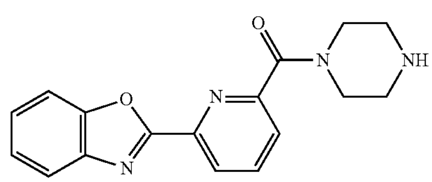 [SMILES: O=C(c1cccc(-c2nc3ccccc3o2)n1)N1CCNCC1] | −9.3 | |
| 4 | BT-15 | 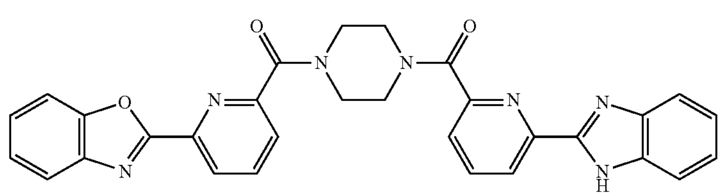 [SMILES: O=C(c1cccc(-c2nc3ccccc3[nH]2)n1)N1CCN(C(=O)c2cccc(-c3nc4ccccc4o3)n2)CC1] | −9.9 | 21.4 |

TABLE 1A-continued

Predicted and Actual SPR Binding of BT-11 and Related Compounds

| Example No. | Compound name | Structure | Predicted Binding Affinity to LANCL2 | SPR Affinity to LANCL2 (Kd) |
|---|---|---|---|---|
| 5 | BT-13 | 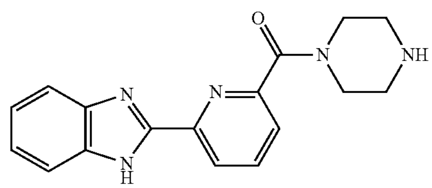 [SMILES: O=C(c1cccc(-c2nc3ccccc3[nH]2)n1)N1CCNCC1] | −7.2 | |
| 6 | BT-4 | 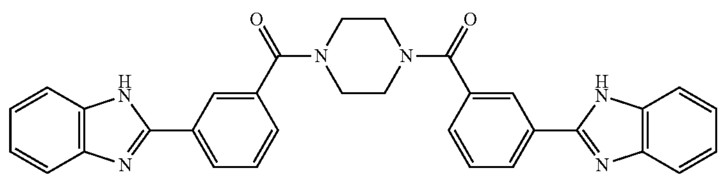 [SMILES: O=C(c1cccc(-c2nc3ccccc3[nH]2)c1)N1CCN(C(=O)c2cccc(-c3nc4ccccc4[nH]3)c2)CC1] | −9.8 | 84.3 |
| 7 | BT-6 | 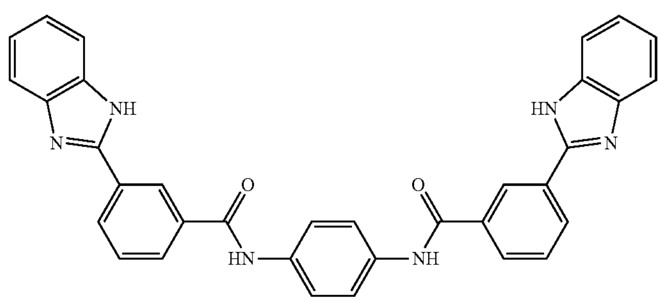 [SMILES: O=C(Nc1ccc(NC(=O)c2cccc(-c3nc4ccccc4[nH]3)c2)cc1)c1cccc(-c2nc3ccccc3[nH]2)c1] | −8.6 | 18.2 |
| 8 | BT-16 | 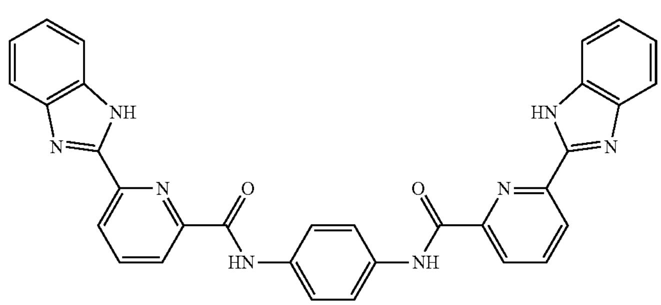 [SMILES: O=C(Nc1ccc(NC(=O)c2cccc(-c3nc4ccccc4[nH]3)n2)cc1)c1cccc(-c2nc3ccccc3[nH]2)n1] | −7.6 | 4.85e−06 |
| 9 | BT-3 | 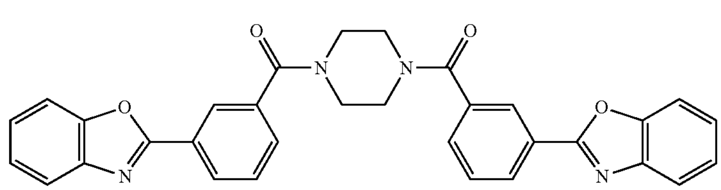 [SMILES: O=C(c1cccc(-c2nc3ccccc3o2)c1)N1CCN(C(=O)c2cccc(-c3nc4ccccc4o3)c2)CC1] | −10.1 | |

TABLE 1B

Predicted and Actual SPR Binding of BT-11 and Related Compounds

| Example No. | Compound name | Structure | Predicted Binding Affinity to LANCL2 | SPR Affinity to LANCL2 (Kd) |
|---|---|---|---|---|
| 10 | BT-5 | 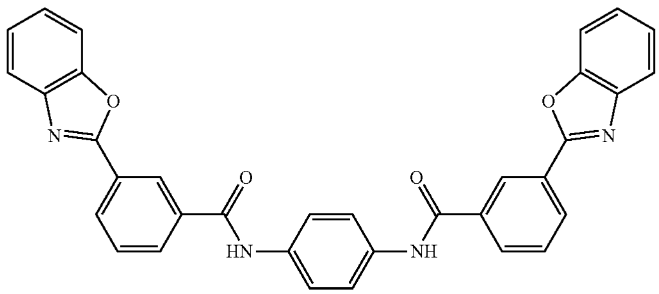 [SMILES: O=C(Nc1ccc(NC(=O)c2cccc(-c3nc4ccccc4o3)c2)cc1)c1cccc(-c2nc3ccccc3o2)c1] | −8.9 | |
| 11 | BT-17 | 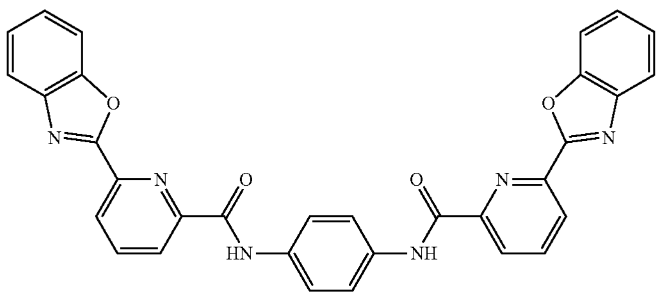 [SMILES: O=C(Nc1ccc(NC(=O)c2cccc(-c3nc4ccccc4o3)n2)cc1)c1cccc(-c2nc3ccccc3o2)n1] | −7.6 | |
| 12 | BT-ABA-25 | 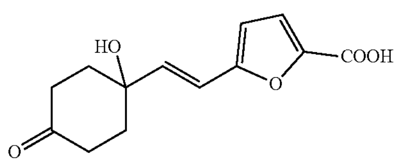 [SMILES: O=C1CCC(O)(/C=C/c2ccc(C(=O)O)o2)CC1] | −7.5 | 1.77e−04 |
| 13 | BT-ABA-5a | 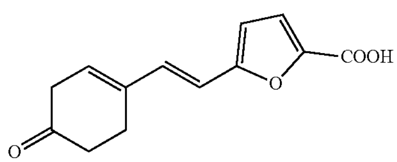 [SMILES: O=C1CC=C(/C=C/c2ccc(C(=O)O)o2)CC1] | −9.5 | 1.17e−05 |
| 14 | BT-ABA-6 | 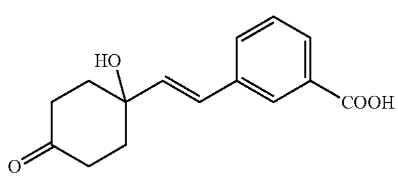 [SMILES: O=C1CCC(O)(/C=C/c2cccc(C(=O)O)c2)CC1] | −7.5 | 163 |
| 15 | BT-ABA-13 | 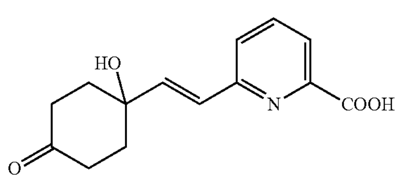 [SMILES: O=C1CCC(O)(/C=C/c2cccc(C(=O)O)n2)CC1] | −7.6 | 4.65e−06 |
| 16 | BT-ABA-16 | 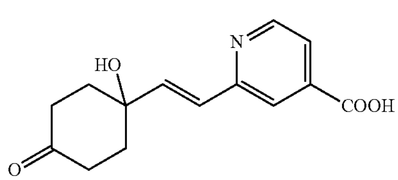 [SMILES: O=C1CCC(O)(/C=C/c2cc(C(=O)O)ccn2)CC1] | −7.6 | 4.85e−06 |

TABLE 1B-continued

Predicted and Actual SPR Binding of BT-11 and Related Compounds

| Example No. | Compound name | Structure | Predicted Binding Affinity to LANCL2 | SPR Affinity to LANCL2 (Kd) |
|---|---|---|---|---|
| REF 18 | 61610 | N1,N4-bis(3-(1H-benzo(d)imidazo-2-yl)phenyl)terephthalamide | −9.1 | 6.2 |
| REF 18 | ABA | | −7.5 | 2.3 |

Additional compounds were virtually screened for binding LANCL2 with AutoDock Vina (Trott et al. *J Comput Chem,* 2010, 31(2):455-61). The binding energy of the top binding pose was determined for each compound. Previously reported protocols and parameters (Lu et al. *J Mol Model,* 2011, 17(3):543-53) were adapted for the present analysis. Table 2 shows some of the tested compounds and their predicted LANCL2 binding energies.

TABLE 2

LANCL2 binding energies of compounds.

| Compound (BT-#) | Binding Energy of Top Pose (kcal/mol) |
|---|---|
| 4 | −10 |
| 23 | −9.3 |

TABLE 2-continued
LANCL2 binding energies of compounds.
| Compound (BT-#) | Binding Energy of Top Pose (kcal/mol) |
|---|---|
| 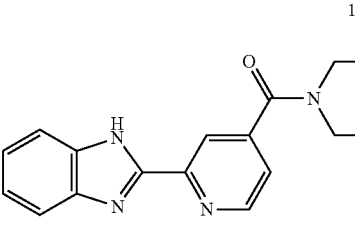 11 | −9.9 |
| 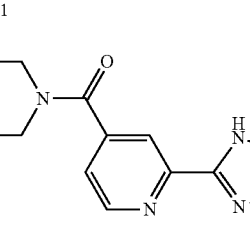 26 | −9 |
| 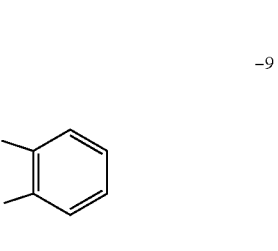 28 | −9.2 |
|  20 | −7.7 |
| 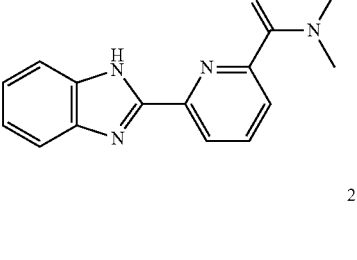 30 | −10.1 |
| 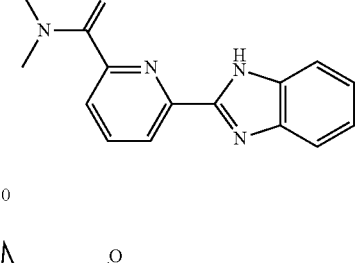 31 | −10.1 |

TABLE 2-continued
LANCL2 binding energies of compounds.
| Compound (BT-#) | Binding Energy of Top Pose (kcal/mol) |
|---|---|
| 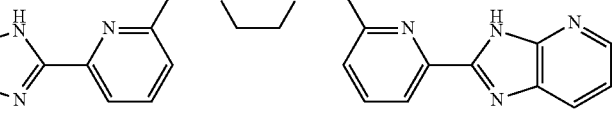<br>33 | −10.1 |
| 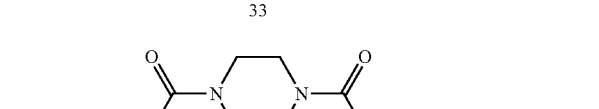<br>34 | −9.8 |
| 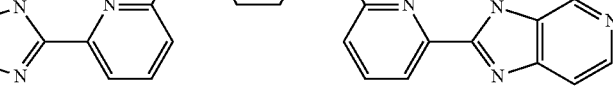<br>36 | −9.1 |
| 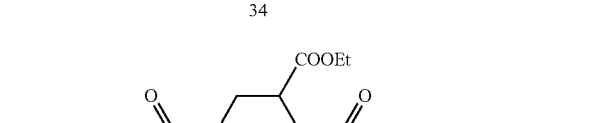<br>37 | −10.4 |
| 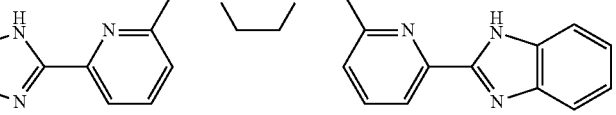<br>38 | −9.7 |
| 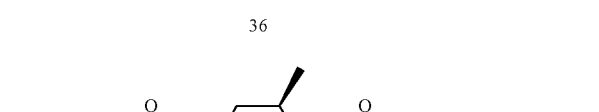<br>39 | −9.9 |

TABLE 2-continued

LANCL2 binding energies of compounds.

| Compound (BT-#) | Binding Energy of Top Pose (kcal/mol) |
|---|---|
| 40 | −10.3 |
| 41 | −10.1 |
| 42 | −10.0 |
| 43 | −10.4 |

Table 3 shows the predicted LANCL2 affinity (binding energy of the top binding pose in kcal/mol) of BT-11 variants. Variations from the BT-11 base structure for each compound in Table 2 are defined according to the variables provided for formula Z-Y-Q-Y'-Z' herein.

TABLE 3

LANCL2 affinity of BT-11 variants.

| Substitution on BT-11 Base Structure | Binding Energy of Top Pose (kcal/mol) |
|---|---|
| Q = propane-1,3-diamine-$N^1,N^3$-diyl | −8.9 |
| Q = $N^1,N^3$-dialkylpropane-1,3-diamine-$N^1,N^3$-diyl | −7.8 |
| Q = 1,4-diaminoanthracene-9,10-dione-1,4-diyl | −11.3 |
| Q = C6 arene-1,4-diamine-$N^1,N^4$-diyl | −10 |
| $A_4$, $A_4'$ = $CR^9$, where $R^9$ = H | −11.2 |
| $A_4$ = $CR^9$, where $R^9$ = H | −10.7 |
| Z' is $R^5$, where $R^5$ = H | −9.5 |
| $R^1$, $R^{1'}$, $R^2$, $R^{2'}$, $R^3$, $R^{3'}$, $R^4$, $R^{4'}$ = $CH_3$ | −10.9 |
| $R^1$ = $CH_3$ | −10.7 |

TABLE 3-continued

LANCL2 affinity of BT-11 variants.

| Substitution on BT-11 Base Structure | Binding Energy of Top Pose (kcal/mol) |
|---|---|
| $R^1$, $R^{1'}$ = $CH_3$ | −10.4 |
| $R^2$ = $CH_3$ | −10.5 |
| $R^2$, $R^{2'}$ = $CH_3$ | −10.5 |
| $R^3$ = $CH_3$ | −10.8 |
| $R^3$, $R^{3'}$ = $CH_3$ | −10.1 |
| $R^4$ = $CH_3$ | −10.1 |
| $R^4$, $R^{4'}$ = $CH_3$ | −9.7 |
| $R^6$ = $CH_3$ | −10.8 |
| $R^7$ = $CH_3$ | −10.9 |
| $R^8$ = $CH_3$ | −10.8 |
| $R^9$ = $CH_3$ | −10.5 |
| $R^{10}$ = $CH_3$ | −10.8 |
| $R^{11}$ = $CH_3$ | −11 |

As shown in Tables 1A, 1B, 2 and 3, BT-11 can accommodate extensive modification and still bind LANCL2 with a high affinity.

Medicinal Chemistry Examples

Examples showing the synthesis of BT-11 and related compounds are provided by U.S. Pat. No. 9,556,146, which is incorporated herein by reference in its entirety.

Experimental Studies Examples

BT-11 Alters Immunometabolic Pathways During Inflammation

Introduction

Inflammatory bowel diseases (IBD), encompassing both Crohn's disease (CD) and ulcerative colitis (UC), afflict 1.6 million North Americans and 4 million worldwide, with nearly 15% growth over the last five years [1,2]. Because of the complex and multifactorial nature of IBD, with symptoms, risk factors, and severity varying along a spectrum, the development of efficacious treatments has been a slow, arduous process [3]. Currently, dominant market therapeutics benefit only small portions of the overall population [4], have high rates of loss of response [5], or induce high rates of side effects, including cancer, infection and death [6,7]. Therefore, there is an unmet clinical need for safer and more efficacious therapeutics for IBD.

Among the array of factors linked to the development of IBD is an imbalance and expansion of inflammatory CD4+ T cells [8]. Their spontaneous high-level production of IFNγ, TNFα, and IL17 among other cytokines, is the major driver of the random flares of inflammation [9]. In contrast, the main role of regulatory CD4+T (Treg) cells is to prevent this expansion, activation and cytokine production. Despite these clear benefits, Treg cells experience an expected compensatory increase in the GI of IBD patients [10] and display normal suppressive function in vitro [11] compared to healthy controls, raising controversy over their tangible impact in disease. Recent evidence suggests that while Tregs characterized by traditional markers do expand in number, these cells might be co-producers of inflammatory cytokines or cells that unstably express FOXP3 in situ [12-14]. This co production creates an intermediate phenotype that more closely associates with an effector/inflammatory CD4+ T cell rather than a typical Treg cell. Additionally, expansion of Tregs has been linked to the responsiveness to current IBD treatments [15]. Potentially, targeting the stability of the fully committed Treg profile can restore efficacy to natural and induced Treg cell function within the GI mucosa.

Recently, the entwined nature of cellular metabolism and immunity has become more prominent within the study of human disease and the development of immune targeted therapeutics [16]. In particular, inflammatory and autoimmune diseases, such as IBD and others, have been identified as prime examples of the potency of immunometabolic regulators [17]. Effector and regulatory CD4+ T cells have pronounced differences in metabolic function with effector cells favoring lactate production and glucose utilization [18], whereas regulatory cell types retain a balanced metabolic profile between fatty acid and glucose oxidation [19]. The interface between immunity and metabolism, known as immunometabolism, gains higher resolution and credibility as new metabolic enzymes and substrates are identified to possess moonlighting functions impacting immunological behavior from hexokinase [20] and GAPDH [21] to enolase [22] and phosphoenolpyruvate [23]. With effects on IL-1β and IFNγ production, FOXP3 expression and calcium signaling, these elements, once thought only to produce energy, have a multitude of potent effects on immune function. By controlling the metabolism of immune cells, immunometabolic therapeutics can effectively prevent differentiation and polarization into inflammatory subsets [24-27].

The previously identified LANCL2-mediated regulation of metabolism in enteroendocrine and muscle cells [28] suggests that an important aspect of LANCL2 and BT-11 therapeutic efficacy may lie in a potential immunometabolic mechanism of action of BT-11 in the GI tract. Namely, the activation of LANCL2, the critical first step behind the efficacy of BT-11, was first shown to exert metabolic effects in non-immune cells, as a receptor for the natural and dietary compound, ABA [28], and a signal transducer for the production of metabolic hormones, prior to the discovery of its role in inflammation [29]. However, the union between the metabolic and immunological actions of the LANCL2 pathway has yet to be proven. As such, LANCL2, and other immunometabolic targets, merit mechanistic evaluation as innovative immunomodulatory methodologies spanning inflammatory and autoimmune disease.

BT-11 has been shown through surface plasmon resonance to target LANCL2 and has been demonstrated through vitro assessments and a DSS model of disease to have a therapeutic action in IBD [30,31]. BT-11's actions after oral administration are highly localized to the GI mucosa with a systemic bioavailability of <10% and plasma half-life of 3.1 hours. Further, preliminary safety studies in rats indicate a clean safety profile up to the limit dose of 1,000 mg/kg p.o. [32]. Early evaluations of efficacy define an improvement in disease activity scores and decrease in inflammatory markers in the colons of mice challenged with DSS. Beyond the activation of LANCL2, the underlying mechanisms of action by which BT-11 reduce disease severity in IBD are currently undefined.

The following examples show that activation of LANCL2 by BT-11 expands and induces stability within regulatory CD4+ T cells via immunometabolic mechanisms to suppress excessive inflammation in the GI mucosa. The following examples also provide the first evidence of immunometabolic effects of BT-11 by activating LANCL2. These data suggest the use of BT-11 in the immunometabolic treatment of a number of diseases or conditions, particularly the inflammation associated therewith.

Materials and Methods

Mice.

Rag2−/− on a C57BL/6 background were obtained from Jackson Laboratories. Mdr1a−/− on a FVB background were obtained from Taconic biosciences. Lancl2−/− and Lancl2fl/fl on C57BL/6 backgrounds were generated through collaboration with a commercial source. Lancl2fl/fl mice were bred to CD4-cre transgenic mice to generate T cell specific Lancl2 knockout animals (Lancl2$^{ΔT}$). Euthanasia was conducted by $CO_2$ narcosis followed by secondary cervical dislocation. Experimental animals were age-, sex- and body weight-matched upon entry into experiments. All studies were performed with the approval of the IACUC.

Induction of Experimental IBD.

Mdr1a−/− model. Mdr1a−/− mice develop spontaneous colitis. At 4 weeks of age, Mdr1a−/− mice began receiving daily treatment with BT-11 (8 mg/kg) via orogastric gavage. Mice were weighed and scored weekly to monitor the development of colitis. At 10 weeks of age, Mdr1a−/− were sacrificed for the collection of tissue for downstream assay. DSS model. Lancl2$^{ΔT}$ and Lancl2-expressing controls were given dextran sulfate sodium in drinking water for seven days. Following seven days, standard drinking water was returned. Mice were weighed and scored daily. Mice were euthanized for tissue collection at 7 and 10 days of experimental timeline. Adoptive transfer model. WT and Lancl2−/− donor spleens were crushed and enriched for CD4+ fraction by magnetic sorting. CD4+CD45RB$^{hi}$CD25− (Teff) and CD4+CD45RB$^{lo}$ CD25+(Treg) cells were sorted by a FACSAria cell sorter. Based on indicated experimental group, Rag2−/− recipient mice received 4×10$^5$ Teff and 1×10$^5$ Treg cells from WT or Lancl2−/− origin by intraperitoneal injection. After transfer, mice received daily treatment of BT-11. Mice were weighed and scored weekly until euthanasia at 8 weeks post-transfer.

Flow Cytometry.

Colons and mesenteric lymph nodes (MLN) were collected into RPMI/FBS buffer containing collagenase (300U/mL) and DNase (50U/mL) for digestion. Following filtration of the resulting single cell suspensions, immune cells were purified by Percoll gradient. Cells were labeled with mixtures of extracellular (CD45, CD3, CD4, CD8, CD19, NK1.1, CD25, F4/80, CD11b, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACS-Diva software.

Gene Expression.

Total RNA from colon and cells was generated using the Qiagen RNeasy mini kit. cDNA was generated using the BioRad iScript cDNA synthesis kit. Standard curves were generated by serial dilution of purified product from a standard PCR reaction with Taq DNA polymerase followed by purification using the Qiagen MinElute PCR purification kit. Expression levels were obtained from quantitative real-time PCR with SybrGreen supermix on a BioRad CFX96 Thermal cycler followed by normalization to expression of β-actin as described previously [33].

Histopathology.

H&E stained colonic sections were prepared from portions of colons collected into 10% buffered formalin and embedded in paraffin. Slides were examined by a board-certified veterinary pathologist via an Olympus microscope and images were collected with Image-Pro software. Samples were scored (0-4) for leukocytic infiltration, epithelial erosion and mucosal thickening.

Metabolic Analysis.

Colons and cells were suspended within assay specific buffer and homogenized for 10 seconds. Homogenate was centrifuged for 10 minutes at 10,000×g. For enzyme activity assays, supernatant was collected and plated. Samples were mixed with enzyme developer and substrate. Colorimetric detection of NADH production was measured using a BioTek μQuant plate reader in combination with Gen5 software. For PEP assay, supernatant was deproteinized using perchloric acid mediated purification. Samples were plated and mixed with a probe, converter, developer mix. PEP concentration was measured by absorbance quantification on plate reader.

In Vitro CD4+ T Cell Culture.

Spleens from WT and Lancl2−/− mice were excised and crushed to generate a single cell suspension. CD4+ T cell fraction was enriched by negative selection via magnetic sorting with the BD IMag system. Naïve CD4+ T cells were obtained by incubation with a biotinylated CD62L antibody followed by conjugation to streptavidin coated magnetic beads. Naïve cells were incubated for 48 hours within anti-CD3 coated tissue culture plates in complete IMDM media containing all-trans retinoic acid and purified TGF-β to stimulate differentiation into Tregs [18]. Cells were plated in media containing indicated concentration of BT-11 from 0 to 48 hours. Metabolic modulators, PS-48 (5 μM), DASA-58 (101 μM), and thapsigargin (10 nM), were added at 0 h. For co-assay, CD4+ fraction and Tregs were generated as described and plated within the same well at a 1:1 ratio of 2×10$^5$ cells each without BT-11 and incubated together for 24 hours. Six hours prior to assay, cells were stimulated with PMA and ionomycin. Cells were collected from plate for downstream analysis by flow cytometry, gene expression and metabolic assay.

Isolation and Culture of Human PBMCs.

Fresh de-identified whole blood was obtained from commercial vendor. Blood was diluted and purified for PBMC fraction by LeukoSep tube. Remaining red blood cells were lysed by hypotonic lysis. Cells were plated in anti-CD3 coated wells in complete RPMI media and incubated with BT-11 for 24 hours. For siRNA experiments, cells were first incubated with an OriGene 3-mer LANCL2 siRNA or scrambled control suspended within ViromerGreen transfection reagent for 6 hours. After six hours, cells were washed and re suspended in fresh media containing BT-11. Cells were stimulated with PMA and ionomycin six hours prior to assay. After 48 hours of BT-11 treatment, cells were collected for flow cytometry, gene expression, and metabolic assay.

Statistical Analysis.

Data are expressed as mean and SEM. Parametric data were analyzed using ANOVA, followed by the Scheffé multiple-comparisons test. ANOVA was performed using the general linear model procedure of SAS (SAS Institute, Cary, NC). A 2×2 factorial arrangement comparing genotype and treatment was used. Statistical significance was determined at P<0.05.

Results

BT-11 Reduces Histopathological, Cellular and Molecular Markers of Inflammation in an Mdr1a−/− Model of IBD.

Figure 1B:
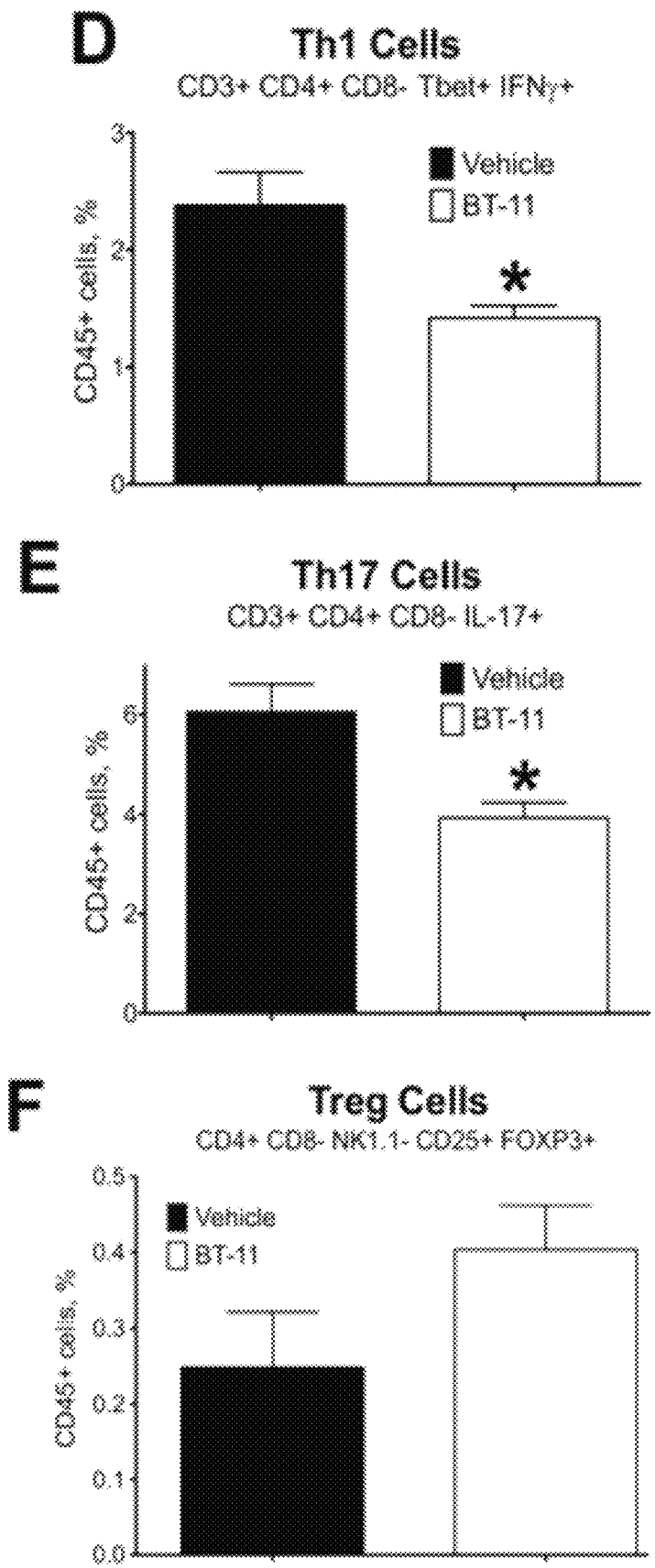
Figure 1C:
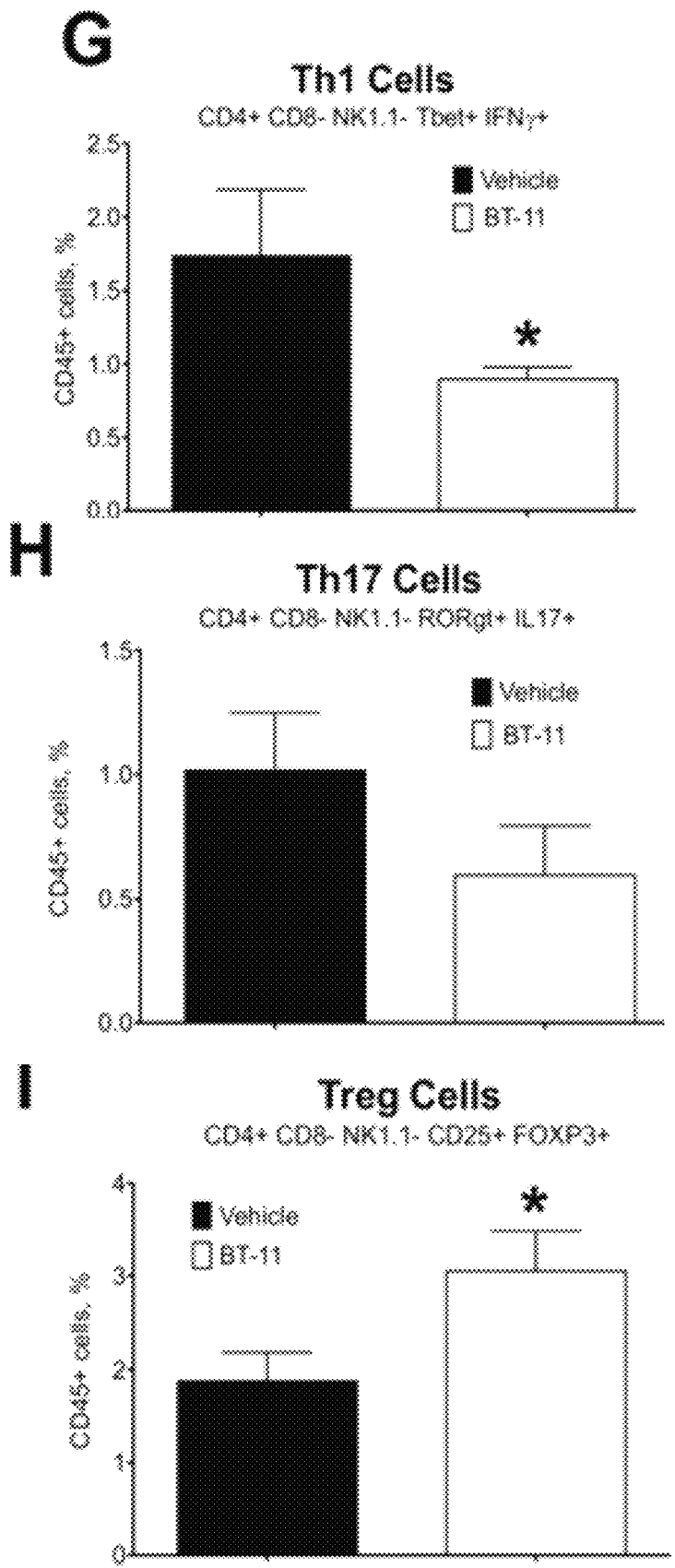
Figure 1D:
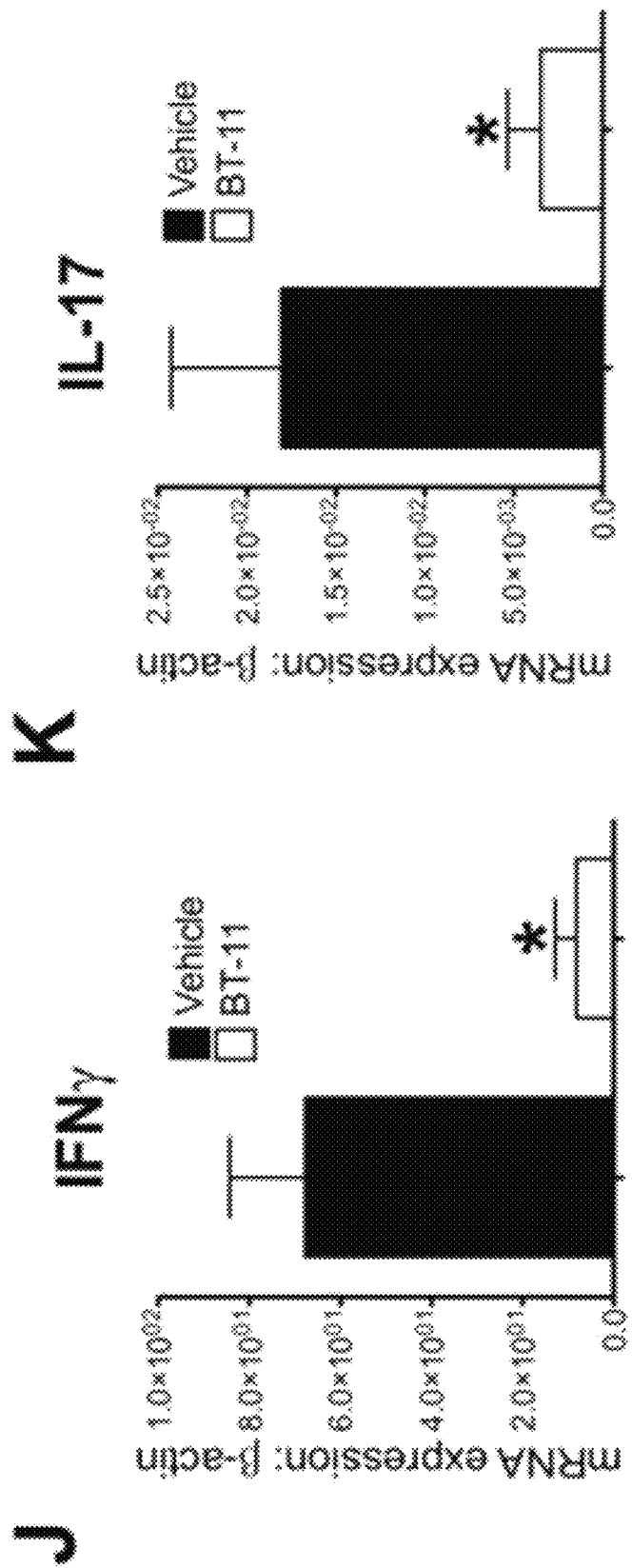
Figure 1E:
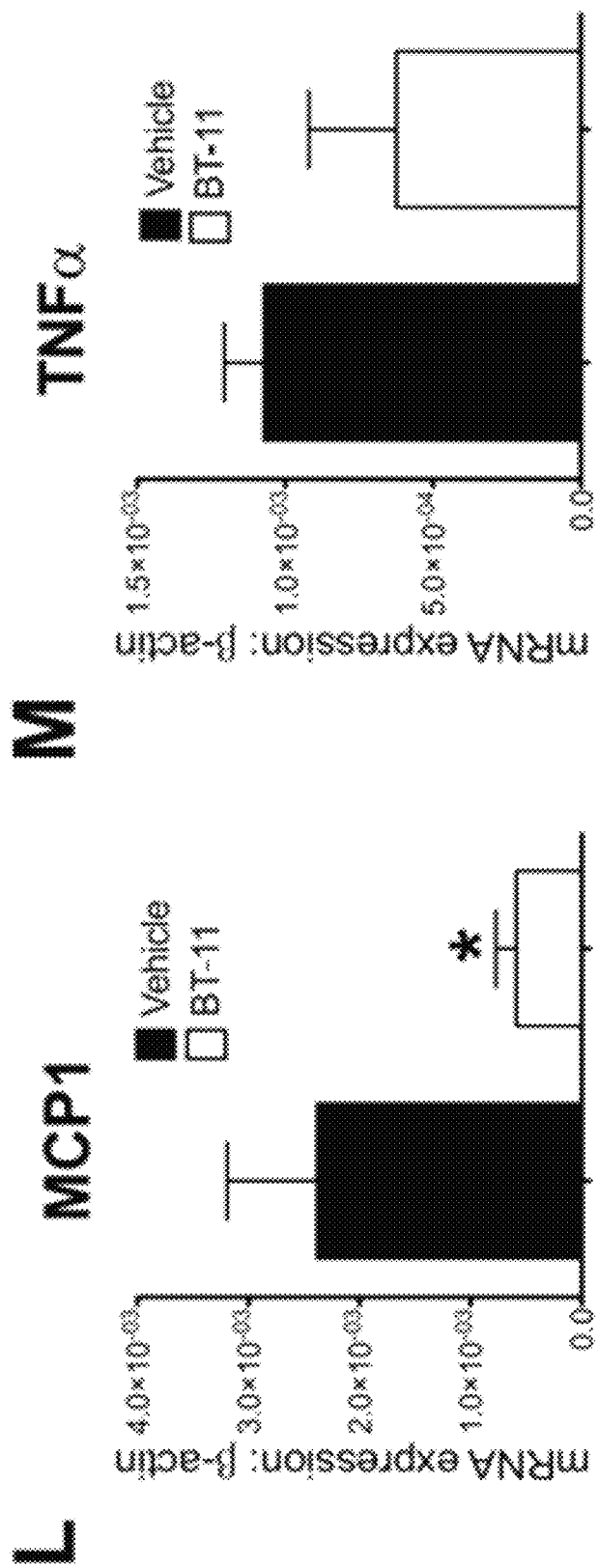
Figure 1F:
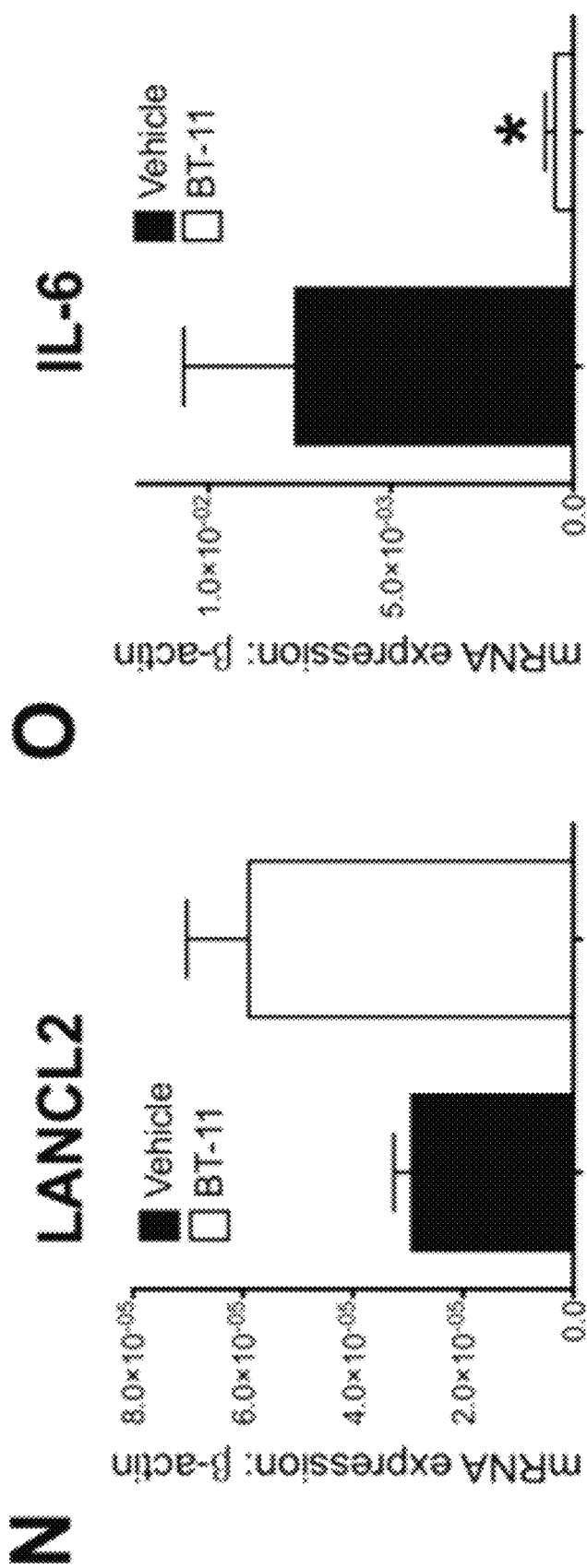

Mdr1a−/− mice were gavaged orally daily with 8 mg/kg BT-11 or vehicle over a six-week period beginning at four weeks of age. Oral treatment with BT-11 prevented the development of disease throughout the six-week period (FIG. 1A, panel A) and reduced colonic leukocytic infiltration, epithelial erosion and mucosal thickening at 10 weeks of age (FIG. 1A, panels B-C). By flow cytometry, significant (P<0.05) reductions in Th1 (CD4+ Tbet+ IFNγ+) and Th17 (CD4+RORγT+IL17+) cells occurred within the colonic lamina propria (LP) (FIG. 1B, panels D-E) and mesenteric lymph nodes (MLN) (FIG. 1C, panels G-H) with BT-11 treatment. In contrast, BT-11 increased percentages of IL-10-producing cellular subsets including CX3CR1+ macrophages (CX3CR1+F4/80$^{hi}$CD11b+CD64+) in the colonic LP and induced Treg cells (CD4+FOXP3+IL10+) in the colonic LP and MLN (FIG. 1B, panel F; FIG. 1C, panel I). Down-regulation of inflammatory cytokines, IFNγ (FIG. 1D, panel J), IL17A (FIG. 1D, panel K), IL6 (FIG. 1F, panel 0), TNFα (FIG. 1E, panel M), and MCP1 (FIG. 1E, panel L), was validated by colonic gene expression and cytometric bead array. Further, oral treatment with BT-11 upregulated whole colon Lancl2 (FIG. 1F, panel N). In addition to functioning prophylactically, BT-11 displays efficacy when given therapeutically, beginning after the presentation of symptoms at 7 weeks of age.

Expression of LANCL2 in CD4+ T Cells is Required for Therapeutic Efficacy of BT-11.

Figure 2A:
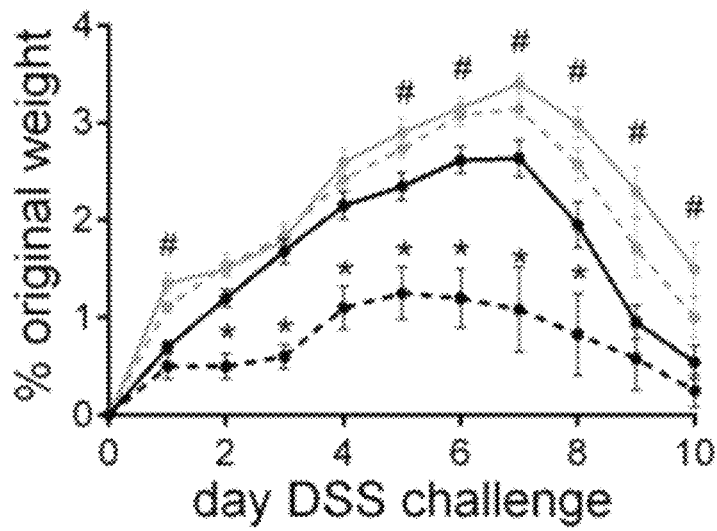
FIGS. 2A-2C. Loss of Lancl2 in CD4+ T cells abrogates BT-11 effects in DSS model. Disease activity (FIG. 2A, panel A) and weight change (FIG. 2A, panel B) over a seven-day challenge with DSS followed by three days of standard water. Representative photomicrographs of H&E stained colonic sections (FIG. 2B, panel C) at day seven of DSS challenge in wild-type mice treated with vehicle and BT-11 and in Lancl2ΔT mice treated with vehicle and BT-11. Immunophenotyping of Th1 (CD3+CD4+CD8-NK1.1- Tbet+ IFNγ+), Th17 (CD3+CD4+CD8-NK1.1- RORγT+IL17+), and Treg (CD3+CD4+CD25+ FOXP3+IL10+) cells, respectively in the colonic lamina propria (FIG. 2C, panels D-F) at day 7 of DSS challenge. qRT-PCR of whole colon of Ifnγ (FIG. 2C, panel G), Il17a (FIG. 2C, panel H), Tnfa (FIG. 2C, panel 1), and Il6 (FIG. 2C, panel J) normalized to β-actin. Statistical significance by treatment group (n=10) marked by * (P<0.05) and ** (P<0.01) and genotype group (n=10) marked by #(P<0.05).
Figure 2A:
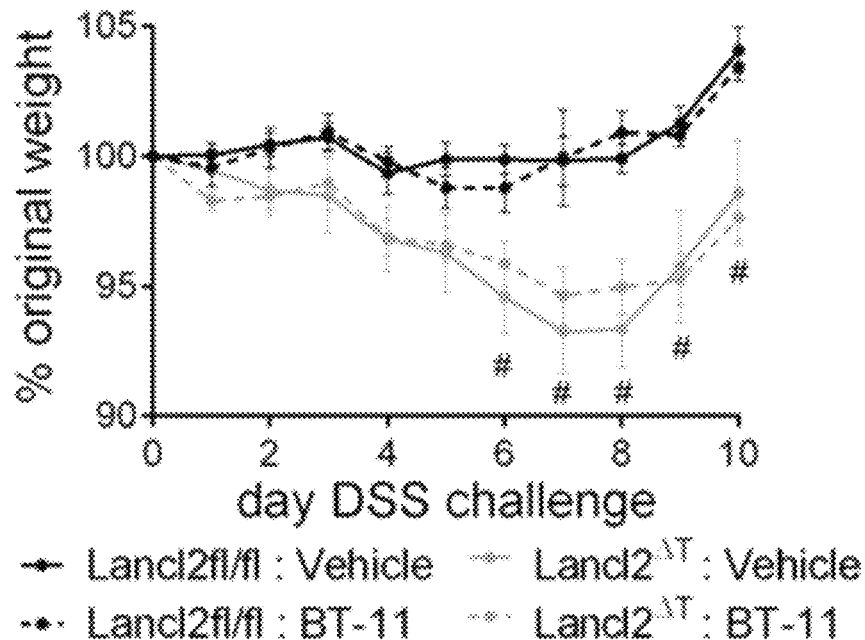
Figure 2B:
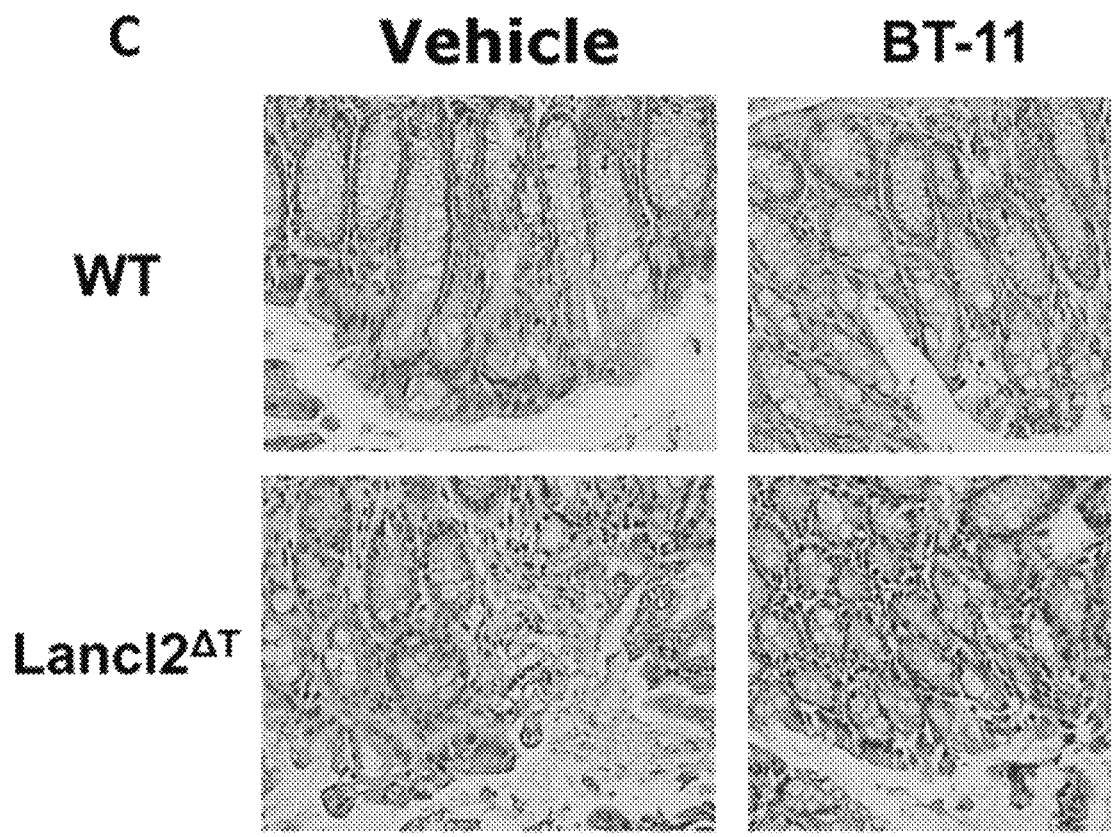
Figure 2C:
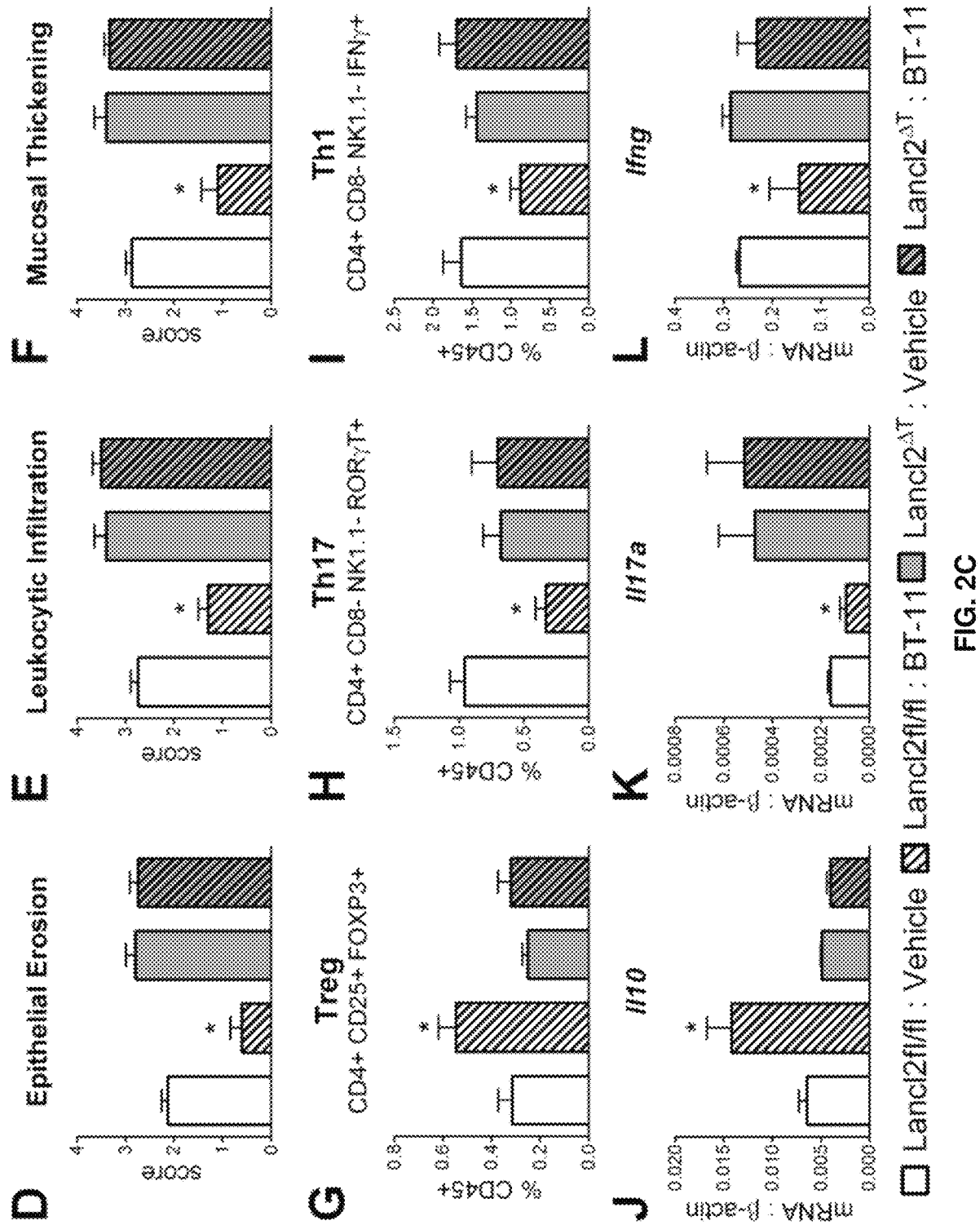

Mice with a CD4-specific deletion of LANCL2 (Lancl2fl/flCD4cre+; Lancl2$^{ΔT}$) were generated using cre-lox technology. Lancl2$^{ΔT}$ and Lancl2-expressing controls were exposed to a seven-day period of DSS and treated with oral BT-11 or vehicle control. The loss of LANCL2 in CD4+ T cells abrogated the efficacy of BT-11 (FIGS. 2A-2C). Lancl2$^{\Delta T}$ displayed increased disease activity, weight loss and increased severity of colonic histopathological lesions (FIG. 2A, panels A-B; FIG. 2B, panel C). At the cellular level, Lancl2$^{\Delta T}$ treated with BT-11 failed to induce characteristic reductions in Th1 and Th17 cells in the colonic LP as well as expand IL-10-producing CX3CR1+ macrophages (FIG. 2C, panels D-F). BT-11-treated and untreated Lancl2$^{\Delta T}$ mice expressed greater levels of inflammatory cytokines within the colon (FIG. 2C, panels G-J).

Oral Treatment with BT-11 Suppresses Inflammation in a Treg-Dependent Mechanism.

Figure 3A:
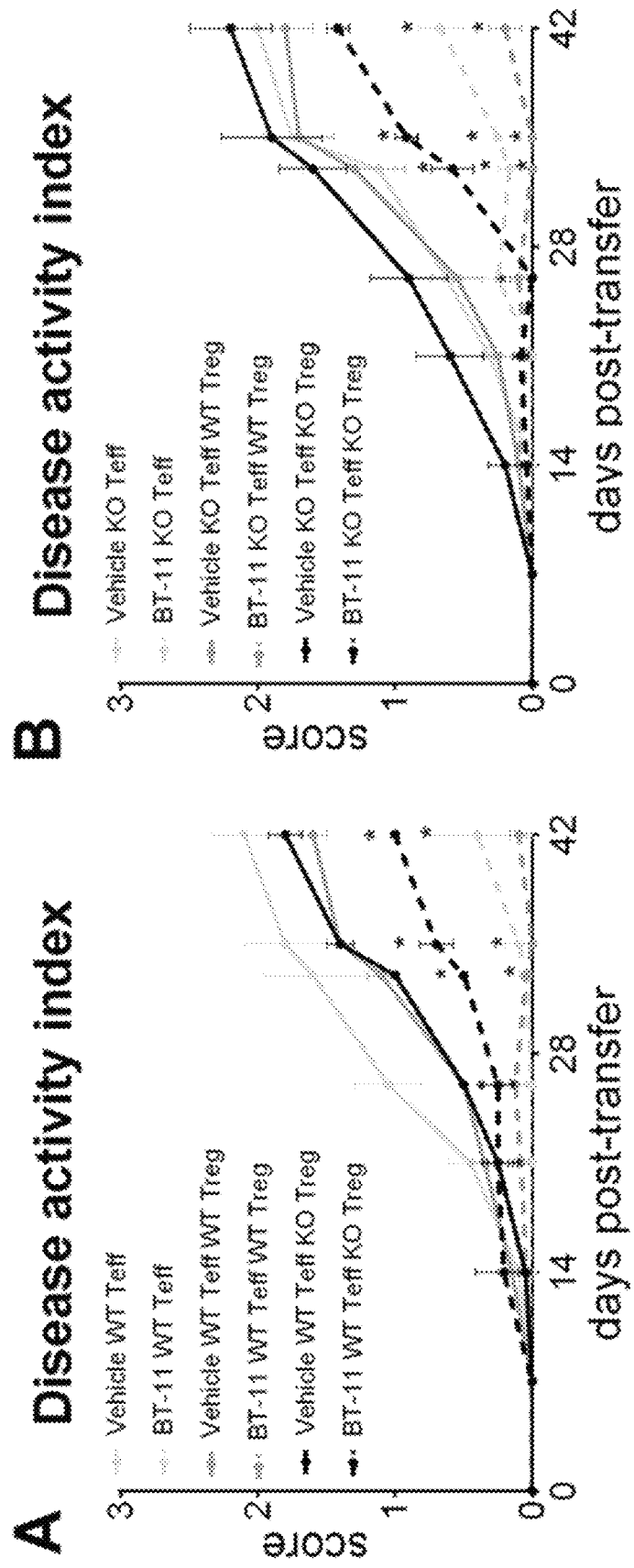
FIGS. 3A-3C. BT-11 exerts primary effects through regulatory CD4+ T cells. Disease activity index from Rag2-/- mice transferred WT (FIG. 3A, panel A) and Lancl2-/- (FIG. 3A, panel B) effector CD4+ T cells in combination with none, WT, or Lancl2-/- regulatory CD4+ T cells from date of transfer to 6 weeks post-transfer. Summarized scores of leukocytic infiltration within colonic section at six weeks post-transfer by histopathological examination (FIG. 3B, panel C). Immunophenotyping of Th1 cells (CD3+CD4+CD8-NK1.1- Tbet+ IFNγ+) and neutrophils (Gr1hiCD11b+) respectively in the colonic lamina propria (FIG. 3B, panels D-E.
Figure 3B:
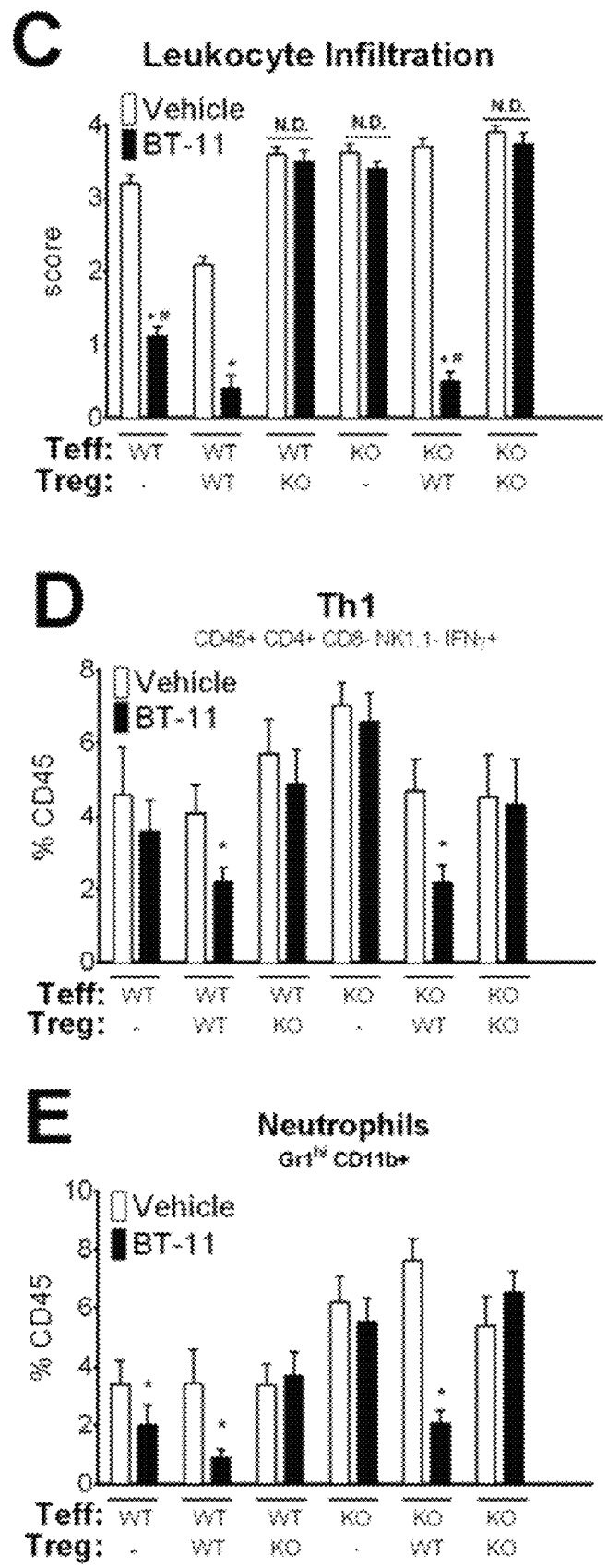
Figure 3C:
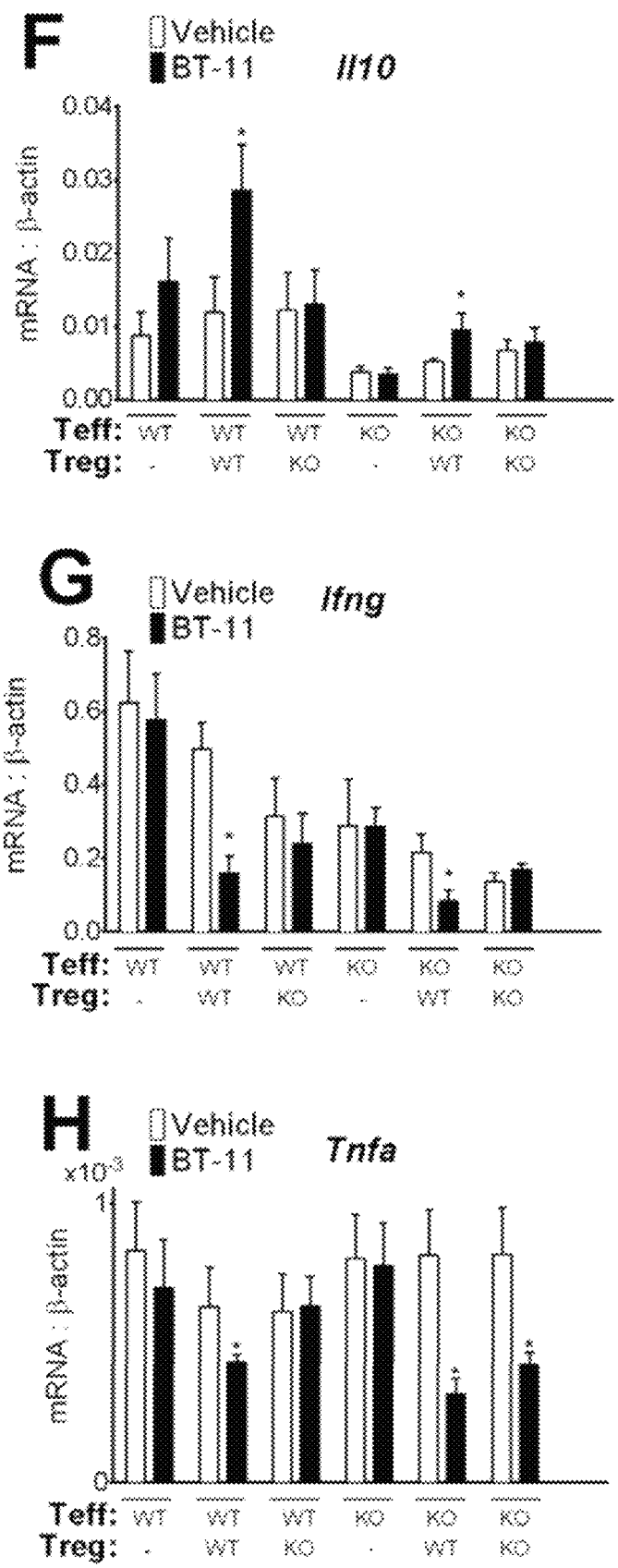

To further characterize the cellular mechanism of action of BT-11 and the T cell-dependency of its therapeutic efficacy, we employed a co-transfer of effector (Teff) and regulatory (Treg) CD4+ T cells from either wild-type (WT) or Lancl2−/− (KO) donors into Rag2−/− mice (FIGS. 3A-3C). Among experimental groups transferred WT Teff, only the group co-transferred WT Treg experienced consistent decreases in inflammation from BT-11 treatment across all measures including disease activity (FIG. 3A, panels A-B), histopathological evaluation (FIG. 3B, panel C), Th1 (FIG. 3B, panel D) and neutrophil (FIG. 3B, panel E) populations in the colonic LP and expression of inflammatory cytokines (FIG. 3C, panels F-H). Notably, the WT Teff/KO Treg group exhibited no benefit of BT-11 treatment in cellular or histopathological characterizations of inflammation. Similarly, oral BT-11 treatment presented efficacy in recipients of WT Treg cells even with the co-transfer of KO Teff. These mice had disease activity, leukocytic infiltration, Th1, and neutrophil measures on par with the WT Teff/WT Treg group. These findings combined with the loss of efficacy in Lancl2$^{\Delta T}$ mice challenged with DSS further validate that the BT-11 mechanism of action is through LANCL2 activation within Treg cells.

Treatment of Tregs with BT-11 Increases Suppressive Capability and Phenotype Stability.

Figure 4:
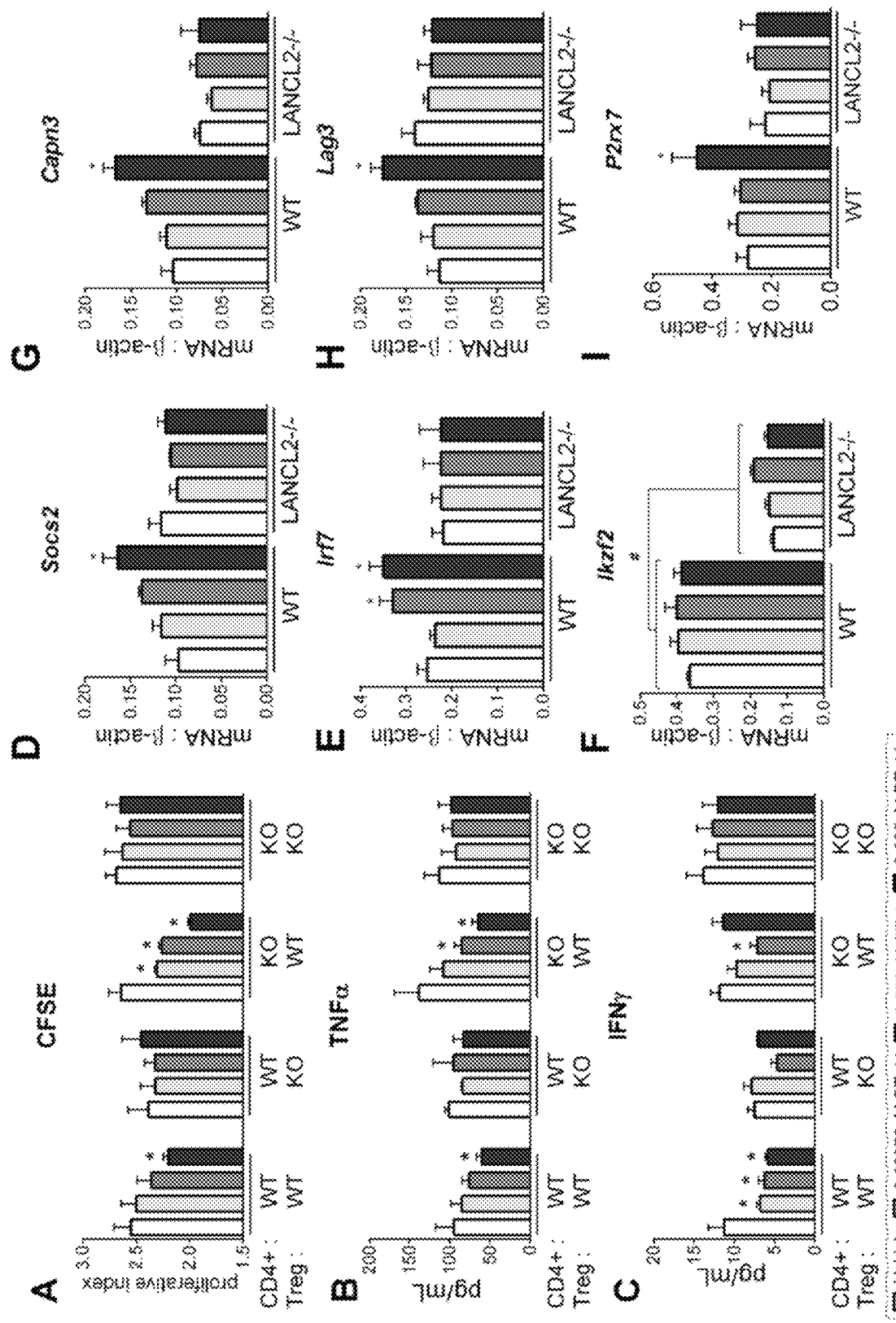
FIG. 4. BT-11 induces increased stability and suppressive function in in vitro differentiated Tregs. Measurement of 24 hour cellular proliferation by CFSE staining (panel A) and TNFα (panel B) and IFNγ (panel C) production by cytometric bead array of CD4+ T cells co-cultured with in vitro differentiated Tregs treated with BT-11 (0, 0.00975, 0.039, 0.6251 µM). Gene expression of Socs2 (panel D), Irf7 (panel E), Ikzf2 (panel F), Capn3 (panel G), Lag3 (panel H), P2rx7 (panel 1) within Tregs after 48-hours of treatment with BT-11. Statistical significance by treatment group (n=9) marked by * (P<0.05) and ** (P<0.01).

To directly validate the findings from the adoptive transfer model, a co-assay of CD4+ and Treg cells was conducted. Treg cells from WT and KO donors were isolated for culture within Treg differentiating media (ATRA, TGFβ) and treatment with BT-11 for a two-day period. After two days cells were collected and plated with freshly collected CFSE-labeled CD4+ T cells. WT Treg treated with BT-11 lowered the proliferative index of both WT and KO cells in addition to the expression of TNFα and IFNγ as measured by cytometric bead array (FIG. 4, panels A-C). In contrast, the pre-treatment of KO Treg with BT-11 did not induce changes in either measure. WT Treg pre-treated with BT-11 also displayed a greater retention of Treg (FOXP3+IL10+) phenotype after the 24h co-assay period. To examine the phenomenon, we assayed the expression of a panel of genes that define stability of the Treg phenotype [34], including Socs2, Capn3, Irf7, Lag3, Ikzf2, and P2rx7 (FIG. 4, panels D-I). Socs2, Capn3, Irf7, and Lag3 displayed a dose-dependent increase in WT Tregs after 48 hours of BT-11 treatment resulting in a significant upregulation of expression at a dosage of 0.6251 μM BT-11. P2rx7 showed no effect at lower doses but was significantly upregulated (P<0.05) at a dose of 0.6251 μM. Meanwhile, Ikzf2 was the only gene to display significant genotype differences. Combined with the observation of Treg cell phenotype retention, these expression results suggest that activation of LANCL2 by BT-11 induces stable expression of Treg-associated genes.

BT-11 Induces Treg Cell Stability Through Immunometabolic Mechanisms of Glucose Flux Control.

Figure 5A:
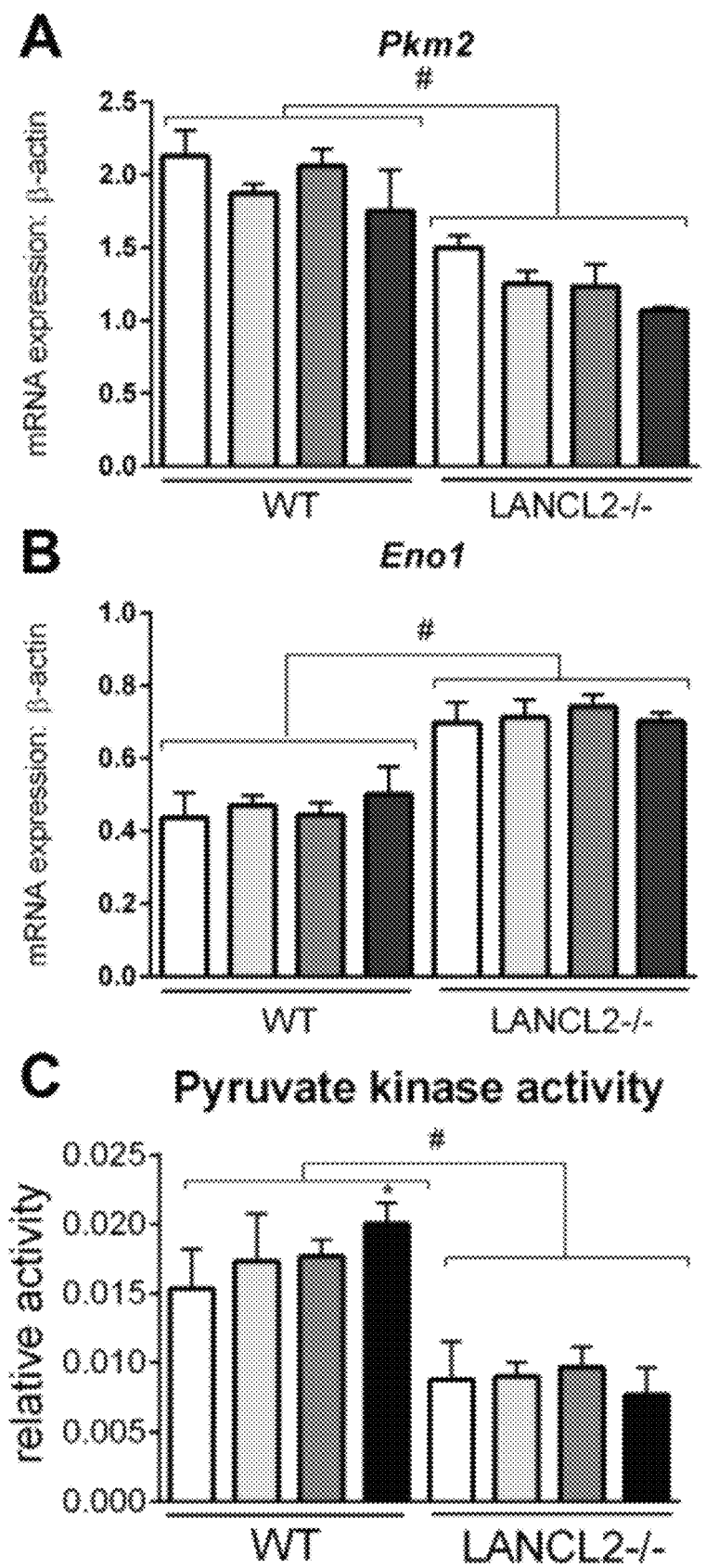
FIGS. 5A-5B. BT-11 influences late-stage glycolysis to affect Treg differentiation. Gene expression of Pkm2 (FIG. 5A, panel A) and Enol (FIG. 5A, panel B) in WT and Lancl2-/- Tregs treated with BT-11 (0, 0.00975, 0.039, 0.6251 µM). Enzyme activity of pyruvate kinase (FIG. 5A, panel C) and pyruvate dehydrogenase (FIG. 5B, panel F) in WT Tregs treated with BT-11 (0, 0.00975, 0.039, 0.156, 0.6251 µM; left to right). Intracellular PEP concentration (FIG. 5B, panel D) in WT Tregs treated with BT-11 (0, 0.00975, 0.039, 0.156, 0.6251 µM; left to right). Intracellular PEP concentration (FIG. 5B, panel E) and pyruvate dehydrogenase activity (FIG. 5B, panel G) with PS-48 treatment (0, 0.00975, 0.156 µM BT-11; left to right). Differentiation of WT and Lancl2-/-CD4+ T cells into Tregs (FIG. 5B, panel H) in the presence of PS-48, thapsigargin or DASA-58 and BT-11 (0, 0.00975, 0.039, 0.156, 0.6251 µM; left to right). Statistical significance by treatment group (n=9) marked by (P<0.05) and ** (P<0.01).
Figure 5B:
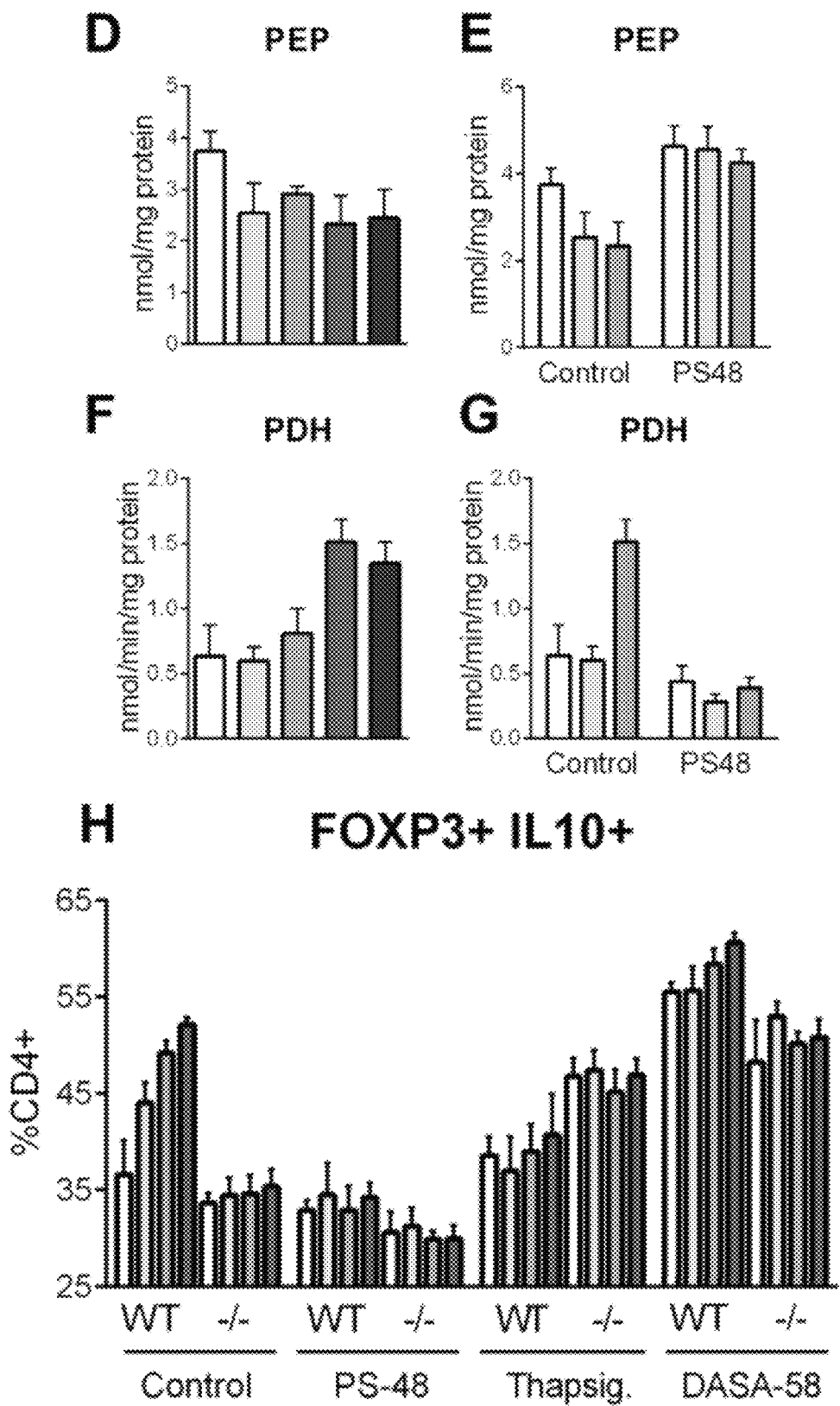

Due to the previous implication of LANCL2 in glucose metabolism [35,36] and the importance of metabolic profile on the differentiation of CD4+ T cells, the effect of BT-11 on glycolysis was examined. Expression of two glycolytic enzymes, Pkm2 and Eno1, were significantly altered by the loss of LANCL2 in Treg cells in vitro (FIG. 5A, panels A-B). Functional enzyme activity provided a profound change with BT-11 treatment. When assayed for enzyme activity, WT Tregs treated with 0.6251 μM displayed an increase in pyruvate kinase activity (FIG. 5A, panel C). The substrate, phosphoenolpyruvate (PEP), concentration of pyruvate kinase was significantly lower in BT-11-treated Tregs compared to vehicle-treated controls (FIG. 5B, panel E). In addition, entrance into the tricarboxylic acid (TCA) cycle, as evidenced by the activity of pyruvate dehydrogenase (PDH), was stimulated by BT-11 treatment, particularly at doses of 0.1561 μM and 0.6251 μM (FIG. 5B, panel F). The BT-11 induced reduction in PEP and PDH activity was abrogated by treatment with PS-48, a small molecule inhibitor of PDH (FIG. 5B, panels G-H). This suggests that BT-11-mediated effects on the glycolytic pathway are dependent on the efficient progression of substrate towards the TCA cycle. Treatment with PS-48 abrogates the increased differentiation of Tregs generated by BT-11 (FIG. 5B, panel D). Additionally, inhibition of SERCA signaling by thapsigargin diminishes the BT-11 induced increase in Treg cell differentiation while stimulation of pyruvate kinase activity with DASA-58 promotes high level differentiation in both treated and untreated cells, demonstrating the importance of end-stage glycolysis processes on CD4+ T cell differentiation.

Inhibition of Metabolic Effects of BT-11 Abrogates Efficacy in Mdr1a−/− Mice with IBD.

Figure 6A:
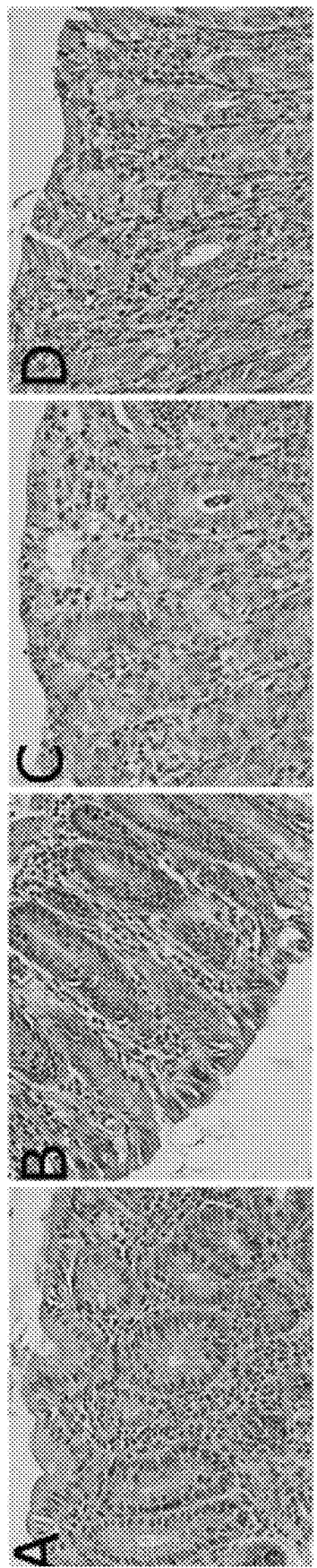
FIGS. 6A-6C. In vivo validation of immunometabolic effect of BT-11. Representative photomicrographs of H&E stained colonic sections at ten weeks of age in vehicle (FIG. 6A, panels A,C) and BT-11 treated (FIG. 6A, panels B,D) mice without and without PS-48 administration, respectively. Histological scores of colon at ten weeks of age (FIG. 6B, panels E-G). Immunophenotyping of total CD4+, Treg (CD3+CD4+CD25+ FOXP3+IL10+), Th17 (CD3+CD4+ CD8-NK1.1- RORγT+IL17+) cells, respectively in the colonic lamina propria (FIG. 6B, panels H-J) at ten weeks of age. PEP concentration (FIG. 6C, panel K) and pyruvate dehydrogenase activity (FIG. 6C, panel L) within whole colon at ten weeks of age. qRT-PCR of whole colon of Ifng (FIG. 6C, panel M), Tnfa (FIG. 6C, panel N), Foxp3-E2 (FIG. 6C, panel O), Foxp3 (FIG. 6C, panel P), Socs2 (FIG. 6C, panel Q), and Capn3 (FIG. 6C, panel R) normalized to β-actin. Conditions for panels E-R are (left to right) vehicle, BT-11 (8 mg/kg), vehicle with PS-48, and BT-11 (8 mg/kg) with PS-48. Statistical significance by treatment group (n=10) marked by * (P<0.05) and ** (P<0.01).
Figure 6B:
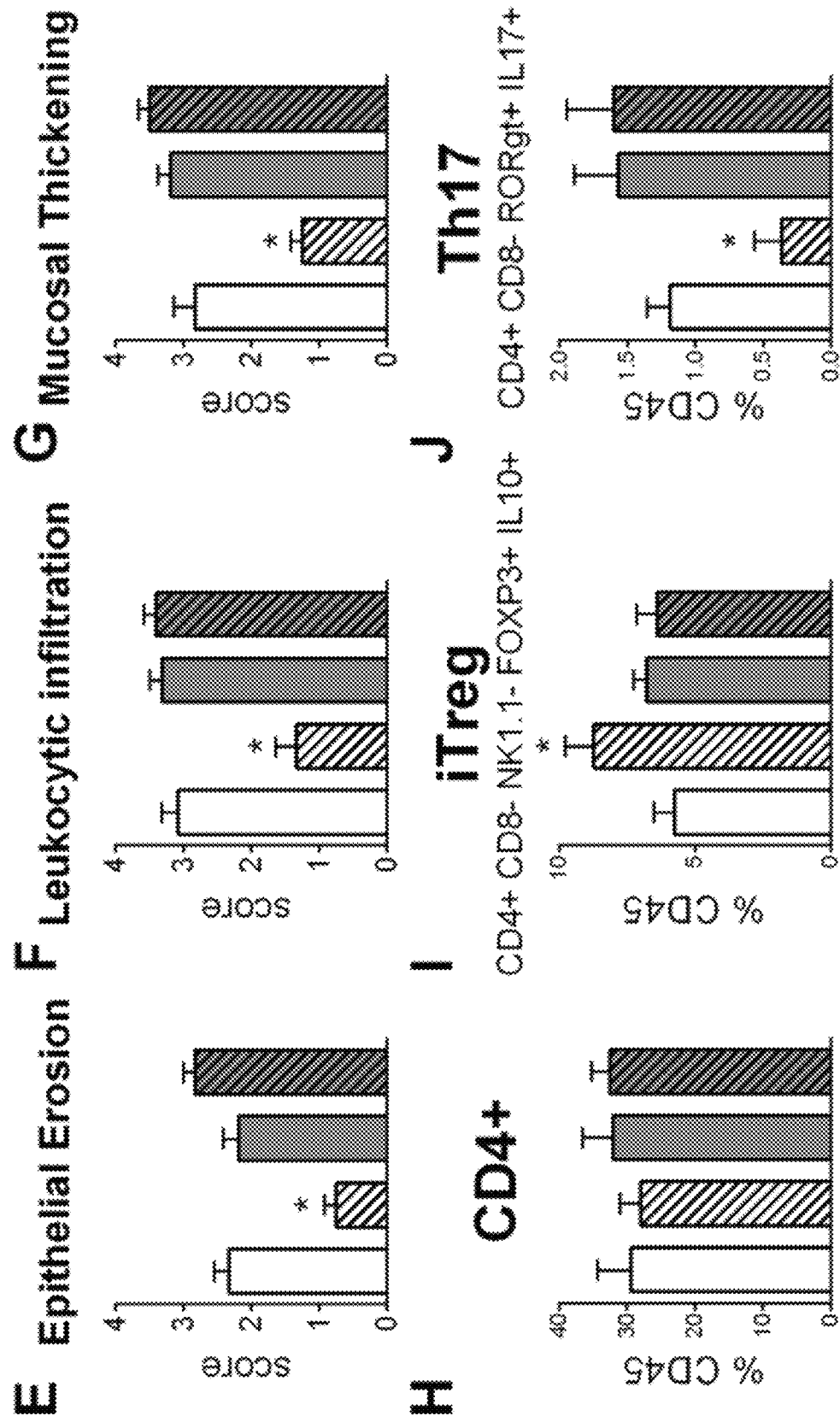
Figure 6C:
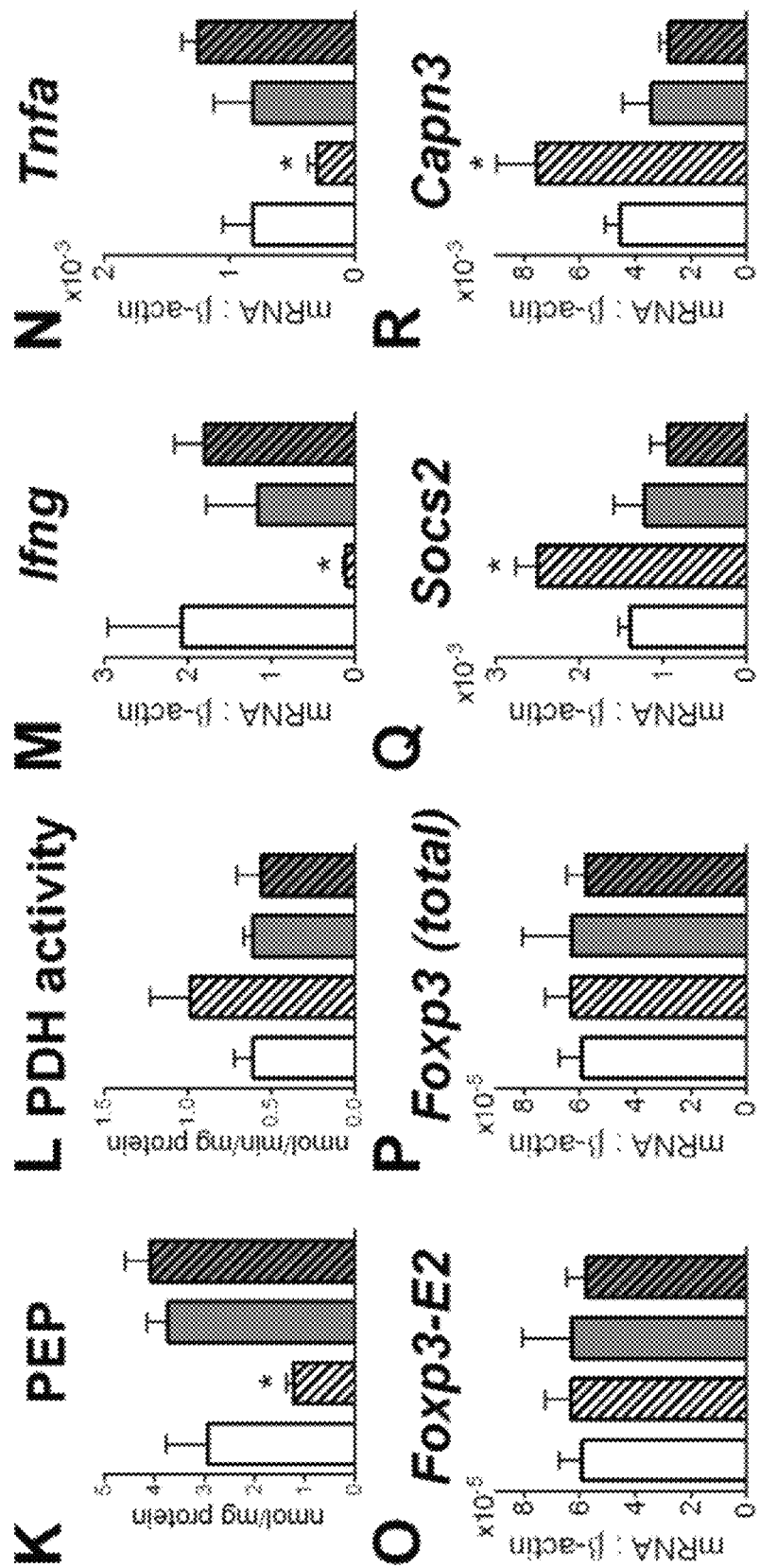

To validate the in vitro immunometabolic findings, Mdr1a−/− mice were given weekly intraperitoneal injections of PS-48 or vehicle control. Mice treated orally with BT-11 and given vehicle injections displayed expected trends in disease activity, histopathology (FIG. 6A, panels A-D), and CD4+ T cell populations (FIG. 6B, panels E-G) as previously observed. Metabolic changes in vitro were validated within the colon at 10 weeks of age with decreased PEP concentration and increased PDH activity with BT-11 treatment (FIG. 6B, panels H-I). Additionally, expression of Treg cell-stability associated genes were upregulated with BT-11 treatment (FIG. 6B, panel J; FIG. 6C, panels K-O). Across the clinical, cellular and metabolic measures, PS-48 effectively blocked the BT-11-induced changes. With the PS-48 injection, the non-BT-11 and BT-11 treated mice had no observable differences in histology, CD4+ T cell populations, and metabolic measures. Similar patterns were observed within the DSS model.

BT-11 Induces Anti-Inflammatory Effects in PBMCs Isolated from Crohn's Disease Donors.

Figure 7A:
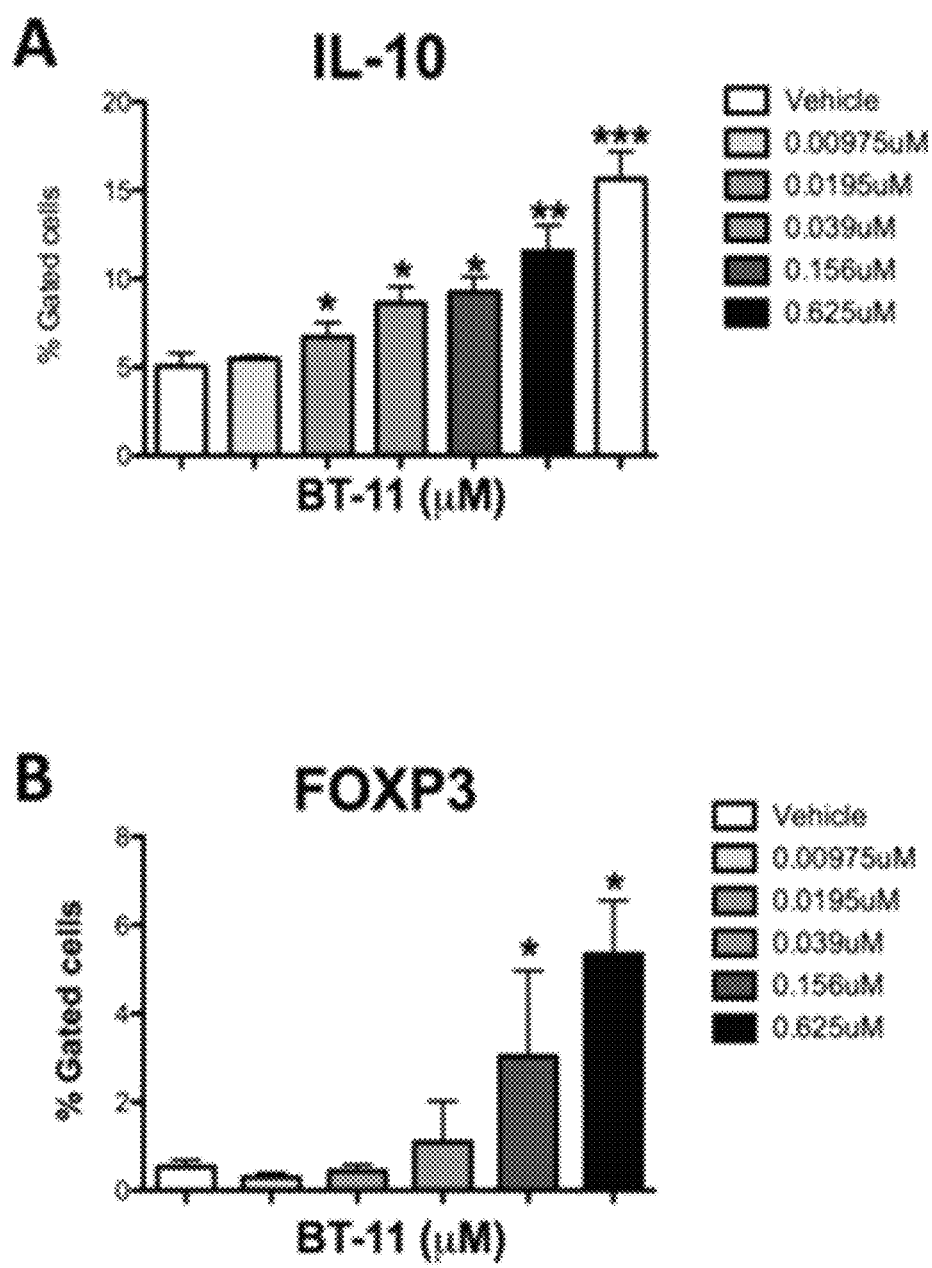
FIGS. 7A-7E. Human PBMC validation of immunometabolic effects of BT-11. Percentage of IL10+(FIG. 7A, panel A), FOXP3+(FIG. 7A, panel B), TNFα+ (FIG. 7B, panel C), and IFNγ+(FIG. 7B, panel D) cells within PBMCs from Crohn's disease donors after 24 hour culture with BT-11 (0, 0.00975, 0.0195, 0.039, 0.156, 0.6251 µM). Percentage of IL10+(FIG. 7C, panel E) and IFNγ+(FIG. 7C, panel F) cells within silencing of Lancl2 after 24 hour culture with BT-11 (0, 0.00975, 0.0195, 0.039, 0.156, 0.6251 µM). Gene expression of Lag3 (FIG. 7D, panel G), Socs2 (FIG. 7D, panel H), Irf7 (FIG. 7D, panel I), P2rx7 (FIG. 7D, panel J), Capn3 (FIG. 7D, panel K), Ikzf2 (FIG. 7D, panel L) within naïve CD4+ T cells isolated from human PBMCs differentiated into Tregs in presence of BT-11. Pyruvate kinase activity (FIG. 7E, panel M) of in vitro differentiated human Tregs. Percentage of FOXP3+(FIG. 7E, panel N) and IFNγ+(FIG. 7E, panel 0) cells after 24 hour culture with BT-11 (0, 0.00975, 0.0195, 0.039, 0.156, 0.6251 µM) and presence of thapsigargin or external PEP. Statistical significance by treatment group (n=9) marked by * (P<0.05) and ** (P<0.01).
Figure 7B:
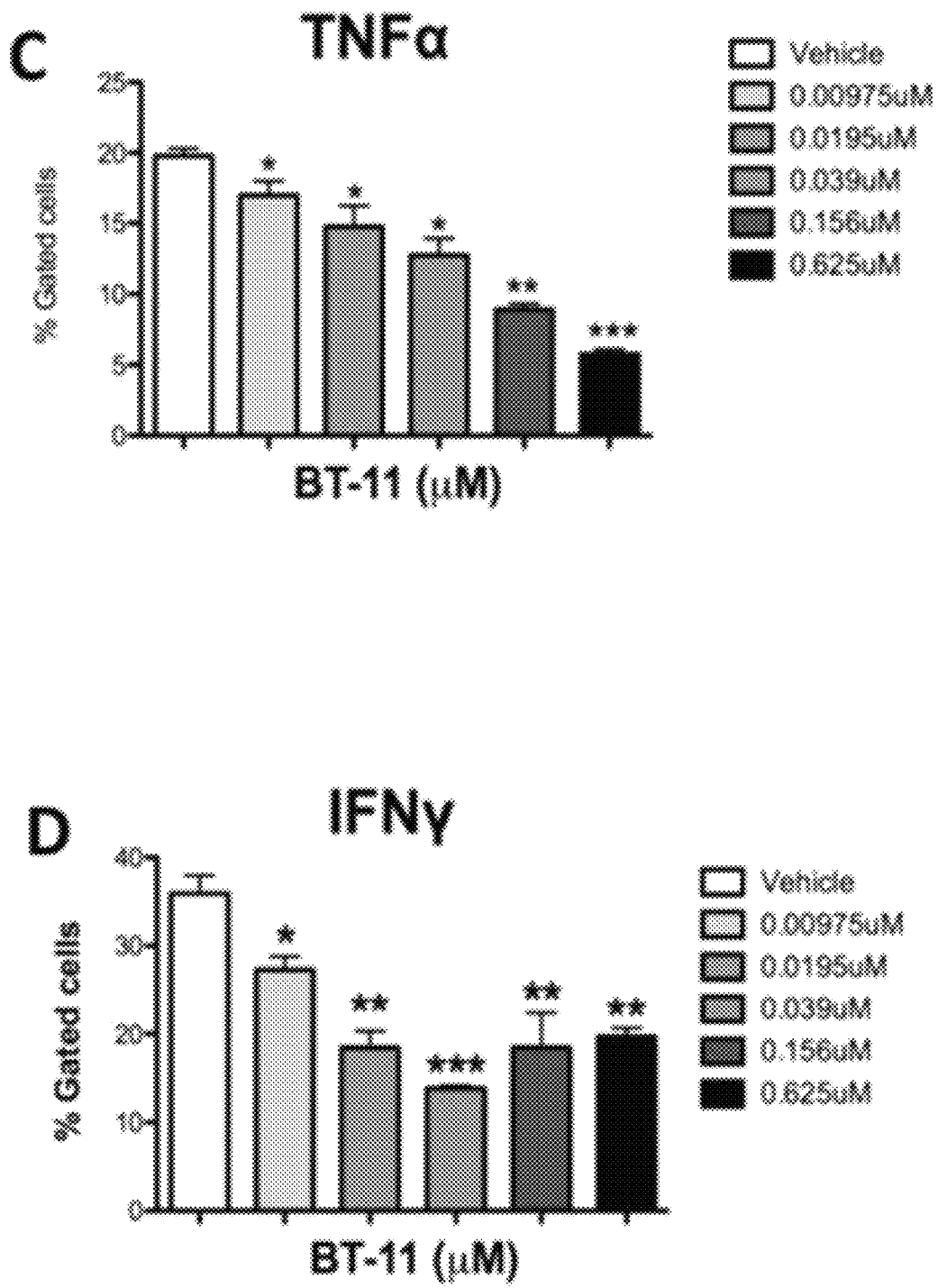
Figure 7C:
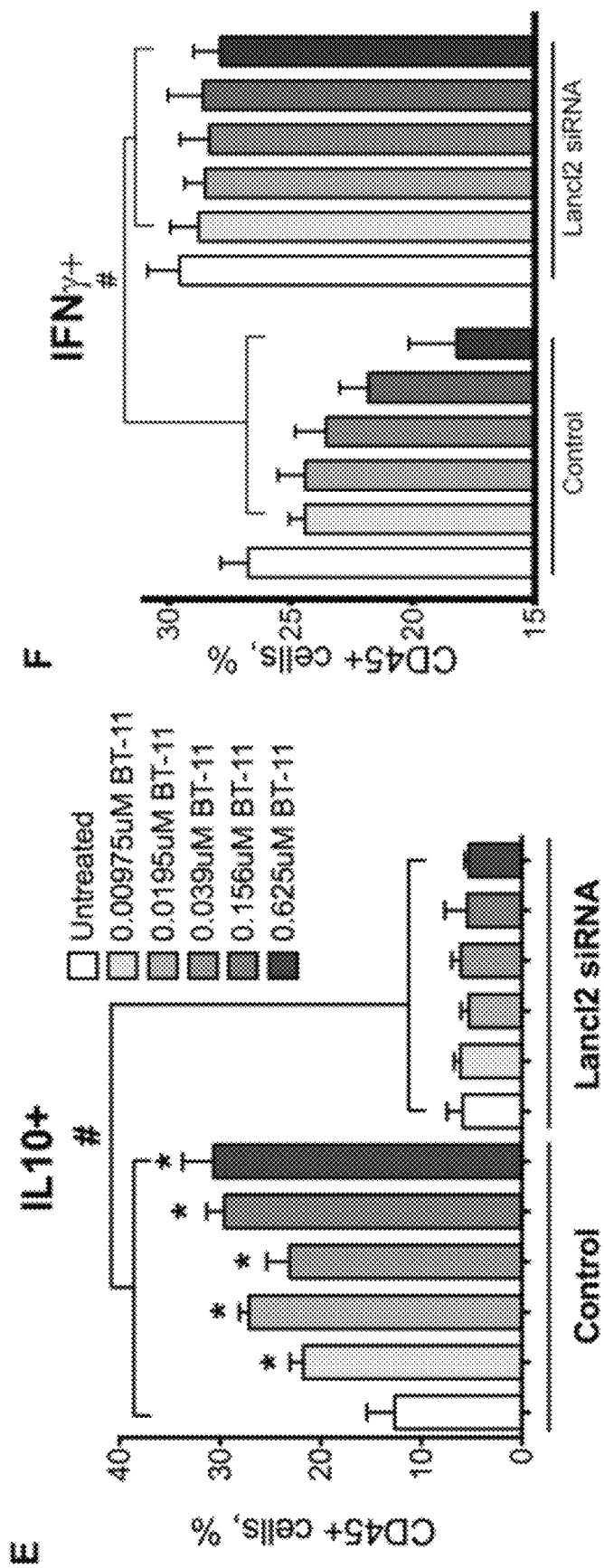
Figure 7D:
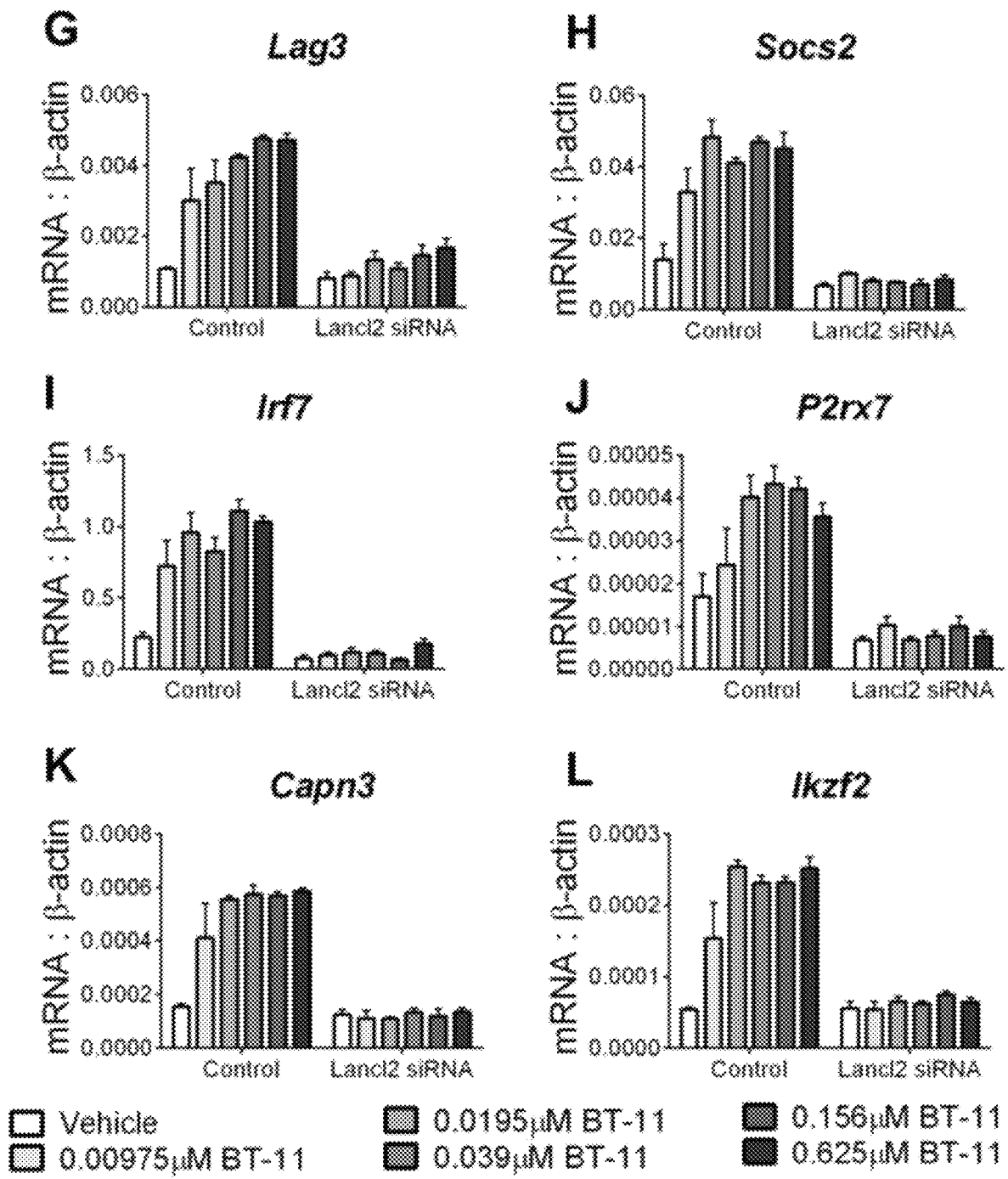
Figure 7E:
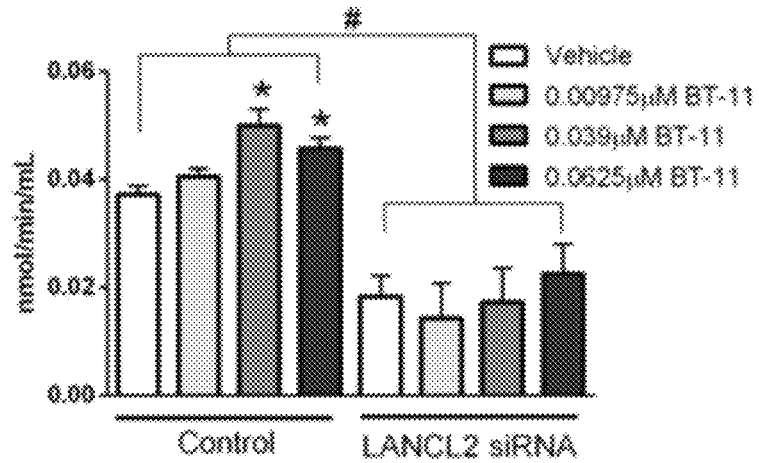
Figure 7E:
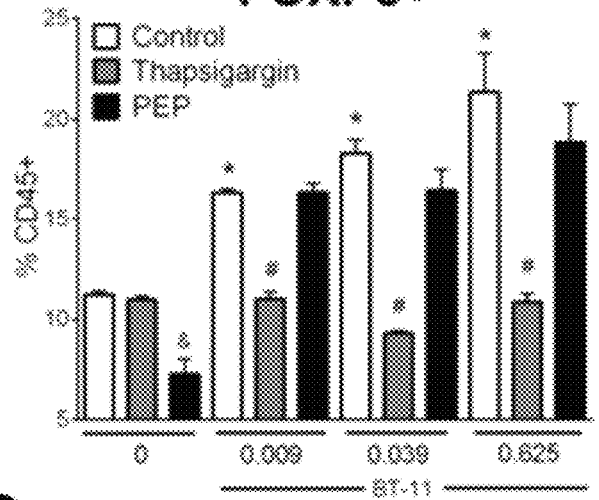
Figure 7E:
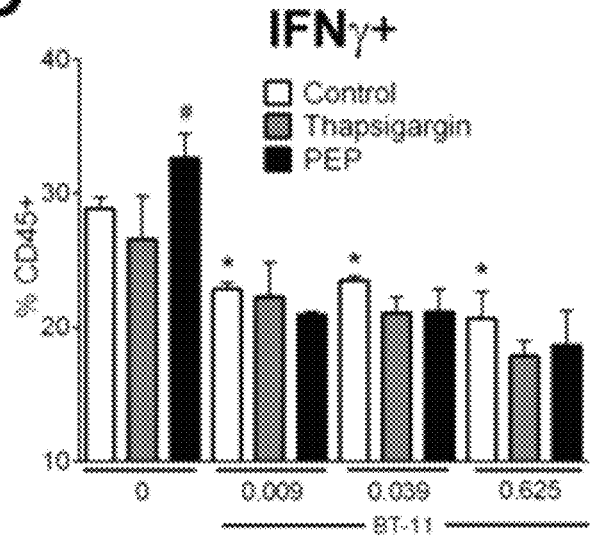

Whole blood was obtained from Crohn's disease patients, clinically categorized as mild to moderate disease. When treated with BT-11, isolated PBMCs had a higher percentage of IL-10+ and FOXP3+ cells and lower percentages of TNFα+ and IFNγ+ cells (FIG. 7A, panels A-B; FIG. 7B, panels C-D). To demonstrate the LANCL2 specificity of BT-11 in human cells, PBMCs were transfected with Lancl2 siRNA or scrambled control. After siRNA transfection, BT-11 effects on IL10+ and IFNγ+ cells were lost (FIG. 7C, panels E-F). From the PBMC fraction, naïve CD4+ T cells were obtained and differentiated into Tregs in the presence of BT-11. As observed within mouse cells, BT-11 induced an upregulation of stability-associated Treg markers in a dose dependent fraction (FIG. 7D, panels G-L). Additionally, metabolic patterns in pyruvate kinase and pyruvate dehydrogenase activity were observed within human Tregs (FIG. 7E, panel M). Thapsigargin prevented the increased induction of FOXP3+ cells in PBMCs treated with BT-11 (FIG. 7E, panel N). Meanwhile, BT-11 prevented cells from an increased commitment to effector phenotypes in the presence of augmented PEP concentration (FIG. 7E, panel O). These results show the translatability of BT-11 efficacy to humans.

Discussion

BT-11 is an orally active, locally-acting first-in-class therapeutic for IBD and other inflammatory conditions. Through this study, we demonstrate therapeutic efficacy in three separate mouse models of IBD and define a novel immunometabolic mechanism of action of BT-11 through LANCL2. BT-11 is a small molecule therapeutic with physicochemical properties designed and optimized for localized action within the GI, minimizing the risk for systemic side effects. A benign safety profile in rats up to the limit dose of 1,000 mg BT-11/kg [32] further indicates the low risk for potential side effects. BT-11 targets the LANCL2 pathway, which has not been noted to possess any genetic mutations that would render its activation futile, thereby taking advantage of a novel mechanism of immunoregulation that is strongly expressed within the GI mucosa in epithelial and immune cells. In this manuscript, we identify that BT-11 functions by influencing a root problem in IBD, the imbalance of effector and regulatory CD4+ T cells. Further, we demonstrate that BT-11 is able to elevate and rescue low-level expression of LANCL2 in the GI tract, restoring any functional abnormalities induced by inflammation in IBD.

The lack of a definitive animal model is a characteristic issue in the development of novel therapeutics in multifactorial diseases, such as IBD. To this end, we validated the efficacy of BT-11 in well-established models encompassing chemical, cellular and genetic methods of induction. BT-11 inhibits exuberant inflammation even with the loss of epithelial cell barrier function and translocation of bacteria in the DSS model, suggesting an ability to maintain mucosal homeostasis in the presence of transient epithelial injury. Meanwhile, in the adoptive transfer model, BT-11 displays a capacity for blocking T-cell driven inflammation in an unrecognized environment. With the loss of recognition to non-harmful antigens a commonly proposed element to IBD pathogenesis, this ability is critical to a successful treatment.

The Mdr1a−/− model specifically is a promising model of human translatability. Unlike other genetic models of disease which generate immunocompromised mice, Mdr1a−/− mice are immunocompetent [37], with the deletion instead impacting the cellular ability to efflux molecules and prevent cellular stress. The accumulation of waste and by-products leads to a dysregulation of the epithelial cell lifecycle and increased secretion of inflammatory cytokines and chemokines. Thus, it provides a chronic and spontaneous onset of disease with primary initiating events occurring within the epithelium. Additionally, the MDR1 gene is an emerging risk allele for IBD and affects the responsiveness to glucocorticoid-based treatments [38,39]. A particular polymorphism within the MDR1 gene, 1236T, has also been associated with an increased risk for resection surgery in CD patients [40]. The ability of BT-11 to provide therapeutic efficacy in the absence of this gene is an important indication of robustness in the presence of genetic abnormalities and suggest efficacy in human translation.

The advances in the interdisciplinary field of immunometabolism are increasingly linked to understanding development of autoimmune disease, digestive disorders and cancer, and offer new unexploited opportunities for therapeutic development. The involvement of the mechanism of action of BT-11 in late stage glycolysis has particular, three-fold importance in the differentiation and stability of Treg cells and induction of remission. Firstly, increased transcription of Eno1 decreases expression of the FOXP3-E2, the isoform of FOXP3 associated with greater suppressive capacity [22]. While free enolase itself may be linked to the altered FOXP3 expression, MBP1, a transcriptional repressor of FOXP3 promoters, is an alternative isoform transcribed from the Eno1 gene [41]. Decreased overall Eno1 transcription and occupation of the enzymatic isoform within glycolysis thereby reduce MBP1 expression and prevent inhibition of FOXP3 expression. Secondly, the balance between lactate production and entrance into the TCA cycle is a critical divide between Teff (contributing to autoimmune disease) and Treg (treating or preventing autoimmune disease) CD4+ T cell subsets, with multiple factors controlling this divide linked to the ability to generate and maintain a Treg population and tolerance in the tissue affected by autoimmune or inflammatory disease. Thirdly, the ability to efficiently process PEP to pyruvate is a requirement for unimpeded SERCA signaling [19,23]. Proper signaling through the SERCA pathway is a checkpoint for the activity of the transcriptional activators of FOXP3, influencing the ability of STAT3 to bind to the CNS2 region, a silencer site, through histone acetylation [42]. These histone modifications are essential for the continued expression of FOXP3 in dividing Treg cells and their loss results in a failure to suppress intestinal inflammation [43,44]. With an altered methylation pattern, Tregs are more susceptible to the co-production of inflammatory cytokines and the intermediate phenotype associated with IBD [45]. The buildup of intracellular PEP can promote multiple inflammatory pathways from the production of lactate to the generation of endoplasmic reticulum stress [46,47], contributing the generation of inflammatory immune cells and survival of epithelial cells. While the impact of SERCA signaling in CD4+ T cells is currently unexplored in IBD, inhibited SERCA function has previously been linked to decreased contractility of the colon and small bowel leading to altered mechanosensory behavior [48].

The increased expression of an entire panel of Treg cell stability-associated genes suggests an effect of BT-11 directly on FOXP3 activity or upstream control of the transcription factor. While the genes together indicate greater suppressive capacity and stability, these downstream targets have important individual impact on disease. Irf7 can increase FOXP3 expression [49] and its absence worsens the severity of colitis [50]. Lag3 is a critical surface molecule for suppressive ability and its expression greatly enhances the efficacy of Treg-based treatments in IBD [51]. Socs2 can downregulate IFNγ expression [52] and the activation of antigen presenting cells [53]. Overall, BT-11 provides an increase in regulatory and anti-inflammatory behavior that promotes the establishment of more stable and anti-inflammatory Treg cell populations.

We provide evidence that BT-11 treatment benefits the behavior of Treg cells in addition to their differentiation through increased suppression of CD4+ proliferation in co-assays. While results within this manuscript focus largely on the actions of iTregs, the evaluation of BT-11 on populations of naturally occurring Tregs provide additional insights for the therapeutic. Notably, Helios, encoded by the Ikzf2 gene and a candidate marker for the discrimination of nTregs and iTregs [54,55], is impacted by the expression of LANCL2 suggesting a potential role for LANCL2 activation in the production of nTreg cells. The onset of IBD and flare-ups in disease severity have been linked to small changes in dietary intake and the commensal gut microbiome with spontaneous development of reactivity to traditionally non-harmful antigens. With current knowledge, oral treatment with BT-11 is expected to induce and restore local tolerance in these situations.

In addition to therapeutic efficacy in validated mouse cells and models of IBD, and in support of its potential for human translation, BT-11 promotes potent effects in human PBMCs. BT-11 reduces production of two prominent inflammatory cytokines, TNFα and IFNγ, in cells obtained from Crohn's disease patients with moderate to severe disease. The ability to induce a native decrease in TNFα expression suggests the potential to occupy a similar therapeutic space as anti-TNFα biologics within moderate to severe Crohn's disease patients. Aside from drastic shifts in cytokine production and cellular differentiation, we demonstrate that identified mechanisms of action translate from murine to human cells in terms of LANCL2 specificity and immunometabolic pathways. The shared mechanism of action establishes feasibility for the translation of therapeutic efficacy from preclinical models of disease and pathology toward clinical trials. Through this study and previous efforts [31,32], BT-11 has emerged as a promising therapeutic for addressing the unmet clinical need for safer, more efficacious oral therapeutics to treat Crohn's disease, ulcerative colitis, and other conditions. Utilizing novel immunometabolic mechanisms through LANCL2, BT-11 occupies a unique space for therapy.

The data indicate efficacy of BT-11 or other LANCL2-binding compounds described herein, or cells activated with of BT-11 or other LANCL2-binding compounds described herein, for treating infectious diseases such as *C. difficile* infection, other bacterial diseases, and other infectious diseases; hyperproliferative disorders such as familial adenomatous polyposis, colorectal cancer, other cancers of the gastrointestinal tract, and other cancers; inborn errors of metabolism such as Andersen disease, other glycogen storage diseases, and other inborn errors of metabolism; chronic immunometabolic diseases such as atherosclerosis, other cardiovascular diseases, hypertension, and other immunometabolic diseases; autoimmune diseases such as lupus, multiple sclerosis, cancer immunotherapy-induced rheumatic diseases, other cancer-immunotherapy-induced autoimmune diseases, and other autoimmune diseases; organ transplant rejection; inflammatory disorders such as acute colonic diverticulitis and radiation-induced inflammation of the gastrointestinal tract such as radiation proctitis, radiation enteritis, and radiation proctosigmoiditis, and other inflammatory disorders; and chronic pain such as fibromyalgia and other types of chronic pain.

REFERENCES

1. Colombel J F, Mahadevan U. Inflammatory Bowel Disease 2017: Innovations and Changing Paradigms. Gastroenterology 2017; 152:309-312.
2. Kaplan G G. The global burden of IBD: from 2015 to 2025. Nat Rev Gastroenterol Hepatol 2015; 12:720-7.
3. Danese S, Fiocchi C, Panes J. Drug development in IBD: from novel target identification to early clinical trials. Gut 2016; 65:1233-9.
4. Yajnik V, Khan N, Dubinsky M, et al. Efficacy and Safety of Vedolizumab in Ulcerative Colitis and Crohn's Disease Patients Stratified by Age. Adv Ther 2017; 34:542-559.
5. Vande Casteele N, Ferrante M, Van Assche G, et al. Trough concentrations of infliximab guide dosing for patients with inflammatory bowel disease. Gastroenterology 2015; 148:1320-9 e3.
6. Keane J, Gershon S, Wise R P, et al. Tuberculosis associated with infliximab, a tumor necrosis factor alpha-neutralizing agent. N Engl J Med 2001; 345:1098-104.
7. Tillack C, Ehmann L M, Friedrich M, et al. Anti-TNF antibody-induced psoriasiform skin lesions in patients with inflammatory bowel disease are characterised by interferon-gamma-expressing Th1 cells and IL-17A11L-22-expressing Th17 cells and respond to anti-IL-12/IL-23 antibody treatment. Gut 2014; 63:567-77.
8. Zenewicz L A, Antov A, Flavell R A. CD4 T-cell differentiation and inflammatory bowel disease. Trends Mol Med 2009; 15:199-207.
9. Strober W, Fuss U. Proinflammatory cytokines in the pathogenesis of inflammatory bowel diseases. Gastroenterology 2011; 140:1756-1767.
10. Maul J, Loddenkemper C, Mundt P, et al. Peripheral and intestinal regulatory CD4+CD25(high) T cells in inflammatory bowel disease. Gastroenterology 2005; 128:1868 78.
11. Holmen N, Lundgren A, Lundin S, et al. Functional CD4+CD25high regulatory T cells are enriched in the colonic mucosa of patients with active ulcerative colitis and increase with disease activity. Inflamm Bowel Dis 2006; 12:447-56.
12. Eastaff-Leung N, Mabarrack N, Barbour A, et al. Foxp3+ regulatory T cells, Th17 effector cells, and cytokine environment in inflammatory bowel disease. J Clin Immunol 2010; 30:80-9.
13. Shevach E M, Davidson T S, Huter E N, et al. Role of TGF-Beta in the induction of Foxp3 expression and T regulatory cell function. J Clin Immunol 2008; 28:640-6.
14. Uhlig H H, Coombes J, Mottet C, et al. Characterization of Foxp3+CD4+CD25+ and IL-10-secreting CD4+CD25+ T cells during cure of colitis. J Immunol 2006; 177:5852-60.
15. Li Z, Arijs I, De Hertogh G, et al. Reciprocal changes of Foxp3 expression in blood and intestinal mucosa in IBD patients responding to infliximab. Inflamm Bowel Dis 2010; 16:1299-310.
16. Leber A, Hontecillas R, Tubau-Juni N, et al. Translating nutritional immunology into drug development for inflammatory bowel disease. Curr Opin Gastroenterol 2016; 32:443-449.
17. Mathis D, Shoelson S E. Immunometabolism: an emerging frontier. Nat Rev Immunol 2011; 11:81.
18. Leber A, Hontecillas R, Tubau-Juni N, et al. NLRX1 Regulates Effector and Metabolic Functions of CD4+ T Cells. J Immunol 2017; 198:2260-2268.
19. Newton R, Priyadharshini B, Turka L A. Immunometabolism of regulatory T cells. Nat Immunol 2016; 17:618-25.
20. Wolf A J, Reyes C N, Liang W, et al. Hexokinase Is an Innate Immune Receptor for the Detection of Bacterial Peptidoglycan. Cell 2016; 166:624-36.
21. Chang C H, Curtis J D, Maggi L B, Jr., et al. Posttranscriptional control of T cell effector function by aerobic glycolysis. Cell 2013; 153:1239-51.
22. De Rosa V, Galgani M, Porcellini A, et al. Glycolysis controls the induction of human regulatory T cells by modulating the expression of FOXP3 exon 2 splicing variants. Nat Immunol 2015; 16:1174-84.
23. Ho P C, Bihuniak J D, Macintyre A N, et al. Phosphoenolpyruvate Is a Metabolic Checkpoint of Anti-tumor T Cell Responses. Cell 2015; 162:1217-28.
24. Cantarini L, Pucino V, Vitale A, et al. Immunometabolic biomarkers of inflammation in Behcet's disease: relationship with epidemiological profile, disease activity and therapeutic regimens. Clin Exp Immunol 2016; 184:197-207.
25. Carbo A, Gandour R D, Hontecillas R, et al. An N,N-Bis(benzimidazolylpicolinoyl)piperazine (BT-11): A Novel Lanthionine Synthetase C-Like 2-Based Therapeutic for Inflammatory Bowel Disease. Journal of Medicinal Chemistry 2016.
26. Fullerton M D, Steinberg G R, Schertzer J D. Immunometabolism of AMPK in insulin resistance and atherosclerosis. Mol Cell Endocrinol 2013; 366:224-34.
27. Souza C O, Teixeira A A, Lima E A, et al. Palmitoleic acid (n-7) attenuates the immunometabolic disturbances caused by a high-fat diet independently of PPARalpha. Mediators Inflamm 2014; 2014:582197.
28. Sturla L, Fresia C, Guida L, et al. LANCL2 is necessary for abscisic acid binding and signaling in human granulocytes and in rat insulinoma cells. J Biol Chem 2009; 284:28045-57.
29. Lu P, Hontecillas R, Home W T, et al. Computational modeling-based discovery of novel classes of anti-inflammatory drugs that target lanthionine synthetase C-like protein 2. PLoS One 2012; 7:e34643.
30. Bassaganya-Riera J, Carbo A, Gandour R D, et al. Novel LANCL2-based Therapeutics, 2016.
31. Carbo A, Gandour R D, Hontecillas R, et al. An N,N-Bis(benzimidazolylpicolinoyl)piperazine (BT-11): A Novel Lanthionine Synthetase C-Like 2-Based Therapeutic for Inflammatory Bowel Disease. J Med Chem 2016; 59:10113-10126.
32. Bissel P, Boes K, Hinckley J, et al. Exploratory Studies With BT-11: A Proposed Orally Active Therapeutic for Crohn's Disease. Int J Toxicol 2016; 35:521-9.
33. Bassaganya-Riera J, Reynolds K, Martino-Catt S, et al. Activation of PPAR gamma and delta by conjugated linoleic acid mediates protection from experimental inflammatory bowel disease. Gastroenterology 2004; 127: 777-91.
34. Delgoffe G M, Woo S R, Turnis M E, et al. Stability and function of regulatory T cells is maintained by a neuropilin-1-semaphorin-4a axis. Nature 2013; 501:252-6.
35. Bassaganya-Riera J, Guri A J, Lu P, et al. Abscisic acid regulates inflammation via ligand-binding domain-independent activation of peroxisome proliferator-activated receptor gamma. J Biol Chem 2011; 286:2504-16.
36. Zocchi E, Hontecillas R, Leber A, et al. Abscisic Acid: A Novel Nutraceutical for Glycemic Control. Front Nutr 2017; 4:24.
37. Haarberg K M, Wymore Brand M J, Overstreet A M, et al. Orally administered extract from Prunella vulgaris attenuates spontaneous colitis in mdr1a(-/-) mice. World J Gastrointest Pharmacol Ther 2015; 6:223-37.
38. Schwab M, Schaeffeler E, Marx C, et al. Association between the C3435T MDR1 gene polymorphism and susceptibility for ulcerative colitis. Gastroenterology 2003; 124:26-33.
39. Yang Q F, Chen B L, Zhang Q S, et al. Contribution of MDR1 gene polymorphisms on IBD predisposition and response to glucocorticoids in IBD in a Chinese population. J Dig Dis 2015; 16:22-30.
40. Bouzidi A, Mesbah-Amroun H, Boukercha A, et al. Association between MDR1 gene polymorphisms and the risk of Crohn's disease in a cohort of Algerian pediatric patients. Pediatr Res 2016; 80:837-843.
41. Lung J, Liu K J, Chang J Y, et al. MBP-1 is efficiently encoded by an alternative transcript of the ENO1 gene but post-translationally regulated by proteasome-dependent protein turnover. FEBS J 2010; 277:4308-21.
42. Mirlekar B, Ghorai S, Khetmalas M, et al. Nuclear matrix protein SMAR1 control regulatory T-cell fate during inflammatory bowel disease (IBD). Mucosal Immunol 2015; 8:1184-200.
43. Li C, Jiang S, Liu S Q, et al. MeCP2 enforces Foxp3 expression to promote regulatory T cells' resilience to inflammation. Proc Natl Acad Sci USA 2014; 111:E2807-16.
44. Ohkura N, Hamaguchi M, Morikawa H, et al. T cell receptor stimulation-induced epigenetic changes and Foxp3 expression are independent and complementary events required for Treg cell development. Immunity 2012; 37:785-99.
45. Li L, Boussiotis V A. The role of IL-17-producing Foxp3+CD4+ T cells in inflammatory bowel disease and colon cancer. Clin Immunol 2013; 148:246-53.
46. Mendez-Lucas A, Hyrossova P, Novellasdemunt L, et al. Mitochondrial phosphoenolpyruvate carboxykinase (PEPCK-M) is a pro-survival, endoplasmic reticulum (E R) stress response gene involved in tumor cell adaptation to nutrient availability. J Biol Chem 2014; 289:22090-102.
47. Vincent E E, Sergushichev A, Griss T, et al. Mitochondrial Phosphoenolpyruvate Carboxykinase Regulates Metabolic Adaptation and Enables Glucose-Independent Tumor Growth. Mol Cell 2015; 60:195-207.
48. Al-Jarallah A, Oriowo M A, Khan I. Mechanism of reduced colonic contractility in experimental colitis: role of sarcoplasmic reticulum pump isoform-2. Mol Cell Biochem 2007; 298:169-78.
49. Wang Z, Zheng Y, Hou C, et al. DNA methylation impairs TLR9 induced Foxp3 expression by attenuating IRF-7 binding activity in fulminant type 1 diabetes. J Autoimmun 2013; 41:50-9.
50. Chiriac M T, Buchen B, Wandersee A, et al. Activation of Epithelial Signal Transducer and Activator of Transcription 1 by Interleukin 28 Controls Mucosal Healing in Mice With Colitis and Is Increased in Mucosa of Patients With Inflammatory Bowel Disease. Gastroenterology 2017; 153:123-138 e8.
51. Do J S, Visperas A, Sanogo Y O, et al. An IL-27/Lag3 axis enhances Foxp3+ regulatory T cell-suppressive function and therapeutic efficacy. Mucosal Immunol 2016; 9:137-45.
52. Cheng S M, Li J C, Lin S S, et al. HIV-1 transactivator protein induction of suppressor of cytokine signaling-2 contributes to dysregulation of IFN{gamma} signaling. Blood 2009; 113:5192-201.
53. Posselt G, Schwarz H, Duschl A, et al. Suppressor of cytokine signaling 2 is a feedback inhibitor of TLR-induced activation in human monocyte-derived dendritic cells. J Immunol 2011; 187:2875-84.
54. Nakagawa H, Sido J M, Reyes E E, et al. Instability of Helios-deficient Tregs is associated with conversion to a T-effector phenotype and enhanced antitumor immunity. Proc Natl Acad Sci USA 2016; 113:6248-53.
55. Takatori H, Kawashima H, Matsuki A, et al. Helios Enhances Treg Cell Function in Cooperation With FoxP3. Arthritis Rheumatol 2015; 67:1491-502.

Treatment of C. Difficile Infection Using Immunometabolic Mechanisms Through Oral Administration of BT-11

Introduction

Increasing *Clostridium difficile* infection (CDI) rates highlight antibiotic selection factors, failing infection-control measures, and deficiencies in current therapies. Antimicrobial therapy with vancomycin and metronidazole produces an expected response rate of 85-90%, accompanied by a 20-25% risk of recurrence for both agents [1-3]. Metronidazole is the preferred first line therapy because of low cost and reduced selectivity pressure for vancomycin resistance. However, both treatments totally destroy normal colonic microflora that provides colonization resistance against *C. difficile* [4, 5]. Recent studies have questioned the efficacy of metronidazole for treating CDI, both in terms of suboptimal primary response and higher-than-expected recurrence rates [6, 7]. Thus, optimizing compounds that are antibiotic-free and promote antibiotic stewardship and microbiome preservation is novel, timely, and urgently needed. The following examples leverage immunometabolic actions to treat *C. difficile* infection.

Methods

C. difficile Animal Model.

This study followed a previously reported model of *Clostridium difficile* infection [11,13,14]. Prior to bacterial challenge, mice were treated with a mixture of antibiotics in drinking water: colistin 850 U/mL (4.2 mg/kg), gentamycin 0.035 mg/mL (3.5 mg/kg), metronidazole 0.215 mg/mL (21.5 mg/kg), and vancomycin 0.045 mg/mL (4.5 mg/kg), followed by an intraperitoneal injection of clindamycin, 32 mg/kg, one day prior to infection. The infectious challenge was with *C. difficile* strain VPI 10463 (ATCC 43255) $10^7$ cfu/mouse in *Brucella* broth via gavage.

Flow Cytometry.

Colons and mesenteric lymph nodes (MLN) were collected into RPMI/FBS buffer containing collagenase (300 U/mL) and DNase (50 U/mL) for digestion. Following filtration of the resulting single cell suspensions, immune cells were purified by Percoll gradient. Cells were labeled with mixtures of extracellular (CD45, CD3, CD4, CD8, CD19, NK1.1, CD25, F4/80, CD11b, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACSDiva software.

Gene Expression.

Total RNA from colon and cells was generated using the Qiagen RNeasy mini kit. cDNA was generated using the BioRad iScript cDNA synthesis kit. Standard curves were generated by serial dilution of purified product from a standard PCR reaction with Taq DNA polymerase followed by purification using the Qiagen MinElute PCR purification kit. Expression levels were obtained from quantitative realtime PCR with SybrGreen supermix on a BioRad CFX96 Thermal cycler followed by normalization to expression of β-actin as described previously [12].

Histopathology.

H&E stained colonic sections were prepared from portions of colons collected into 10% buffered formalin and embedded in paraffin. Slides were examined by a board-certified veterinary pathologist via an Olympus microscope and images were collected with Image-Pro software. Samples were scored (0-4) for leukocytic infiltration, epithelial erosion and mucosal thickening.

Bacterial Re-Isolation.

Colonic contents were collected from excised colons. Samples were homogenized in *Brucella* broth and incubated at 68° C. for one hour. Samples were centrifuged at 10,000 rpm for 30 seconds and the supernatant was collected. The supernatant was serially diluted (1:10, 1:100, 1:1000) and plated on Oxoid *Clostridium difficile* agar plates containing *Clostridium difficile* selective supplement. Plates were incubated in anaerobic conditions using a BD EZ anaerobic container system kit for 2 days at 37° C. Colonies were counted and compared to sample weight for normalization.

Results

LANCL2 Influences the Gastrointestinal Microbiome.

Figure 8:
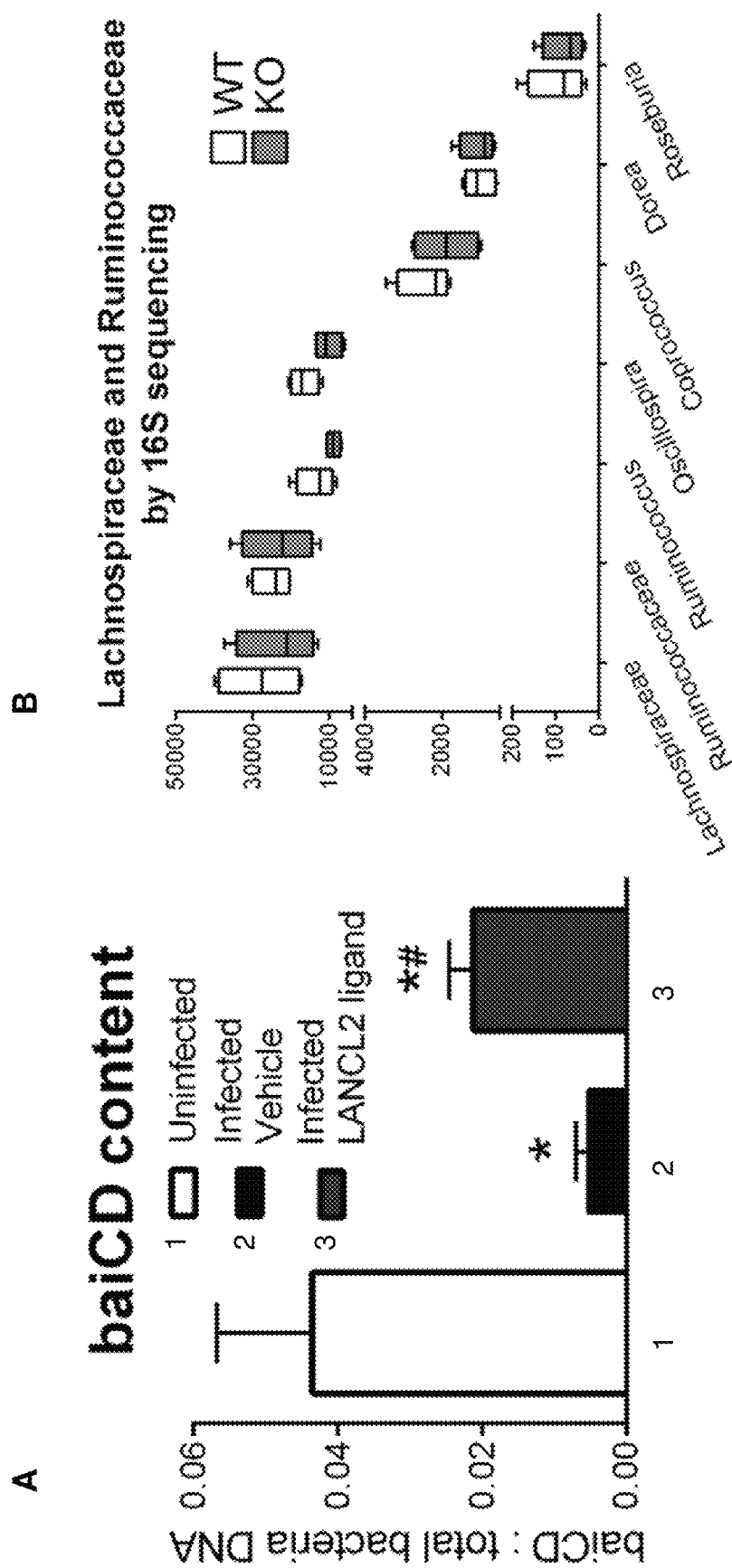
FIG. 8. Microbiome changes in *C. difficile*-infected mice resulting from BT-11 treatment as an LANCL2 ligand and in non-infected, LANCL2 knockout mice.

Activation of LANCL2 in *C. difficile*-infected mice significantly increases baiCD content on dpi 4 compared to vehicle (FIG. 8, panel A). Dominant butyrogenic families, Lachnospiraceae and Ruminococcaceae, are decreased with the loss of LANCL2 in uninfected mice (FIG. 8, panel B). Furthermore, the expression of antimicrobial peptides DefB1 and S 100A8 were found to be upregulated with CDI [11]. Therefore, commensal microbiome dynamics are hindered by the inflammation present in response to *C. difficile*, indicating immunoregulatory-based therapeutics have a positive effect on the microbiota-mediated inhibition of *C. diffacile* expansion and colonization [9].

BT-11 does not Possess Anti-Microbial Properties Towards *C. diffacile*.

Figure 9:
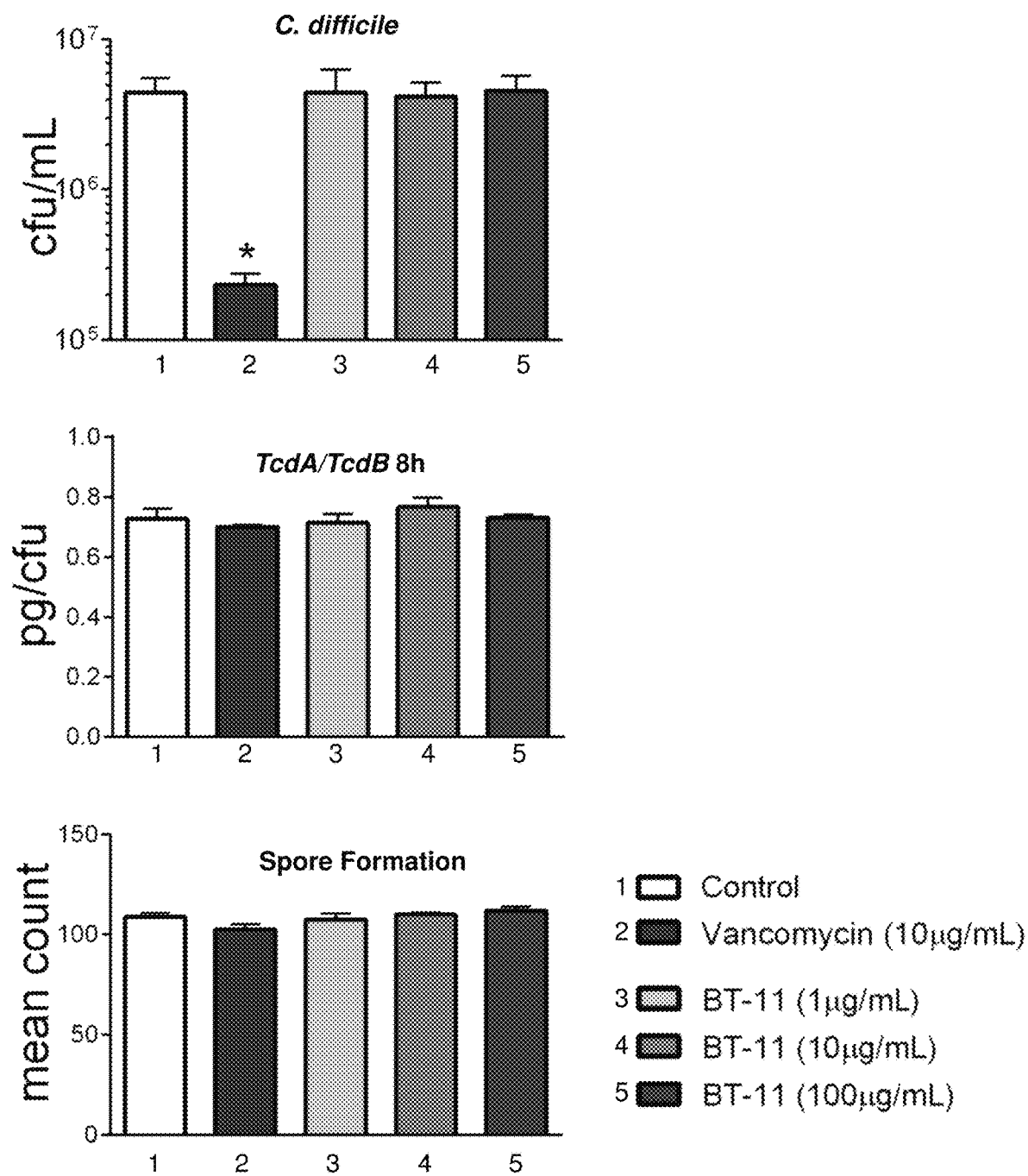
FIG. 9. *C. difficile* colony forming units, Toxin A (TcdA) and Toxin B (TcdB) production, and spore formation in control, vancomycin-treated, and BT-11-treated chopped meat media.

*C. difficile* was incubated in anaerobic conditions within chopped meat media and containing BT-11, vehicle or vancomycin as a positive control. BT-11 was tested at 1 ug/mL, 10 ug/mL and 100 ug/mL. Results are shown in FIG. 9. No concentration of BT-11 tested induced a decrease in colony forming units 24 hours after inoculation. Meanwhile, 10 ug/mL of vancomycin reduced colony forming units by 95%, from 4 million to under 200,000. Exposure to BT-11 did not change production of Toxin A or Toxin B or the ability of *C. difficile* to form spores.

BT-11 Reduces Disease Severity and Protects Against Mortality.

Figure 10A:
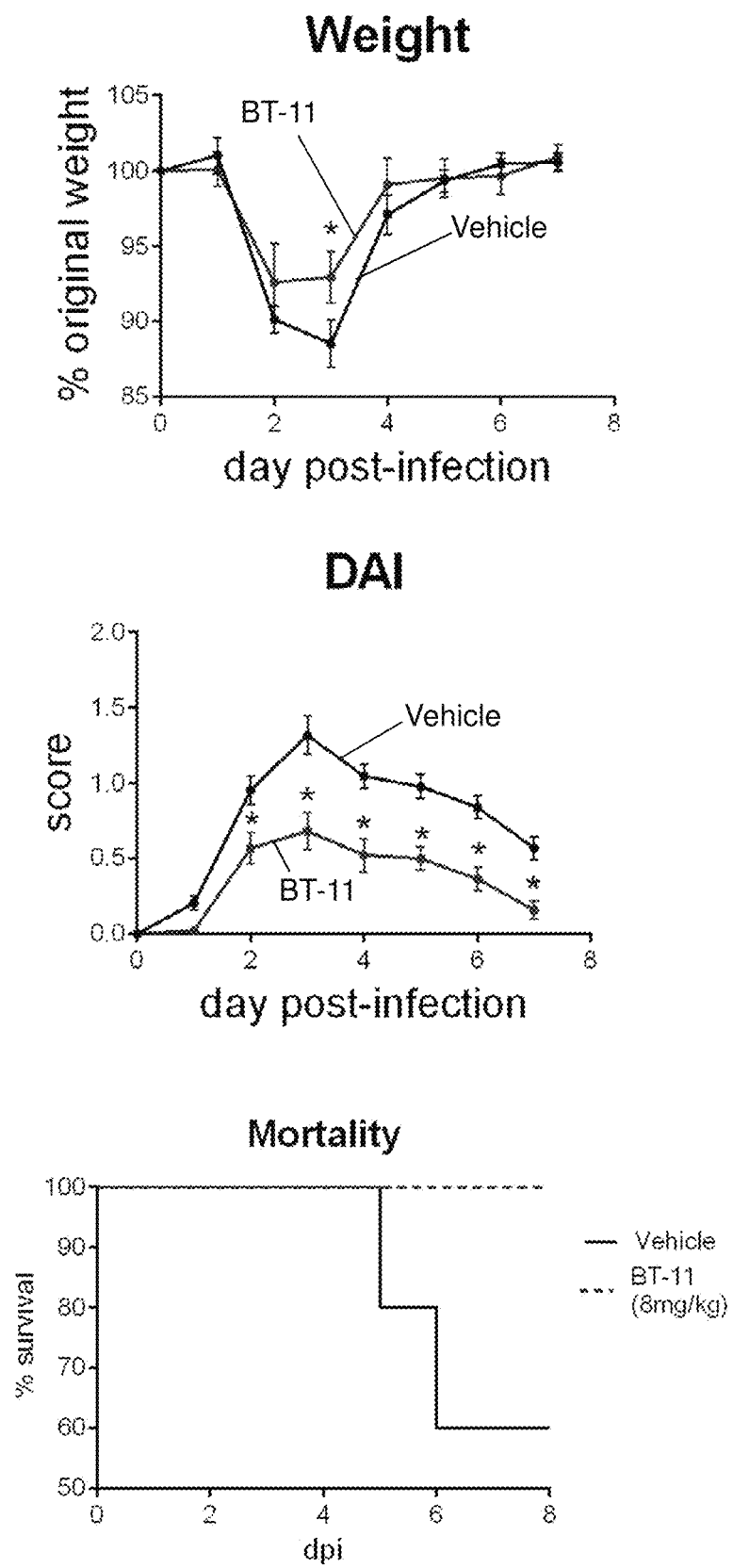
Figure 10B:
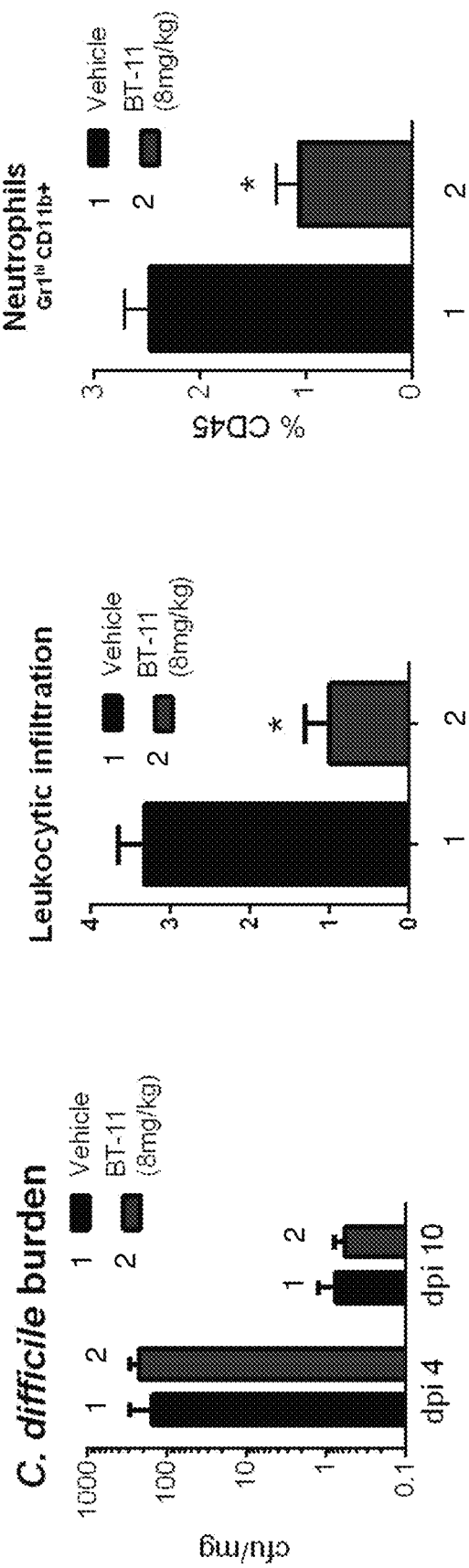
Figure 10C:
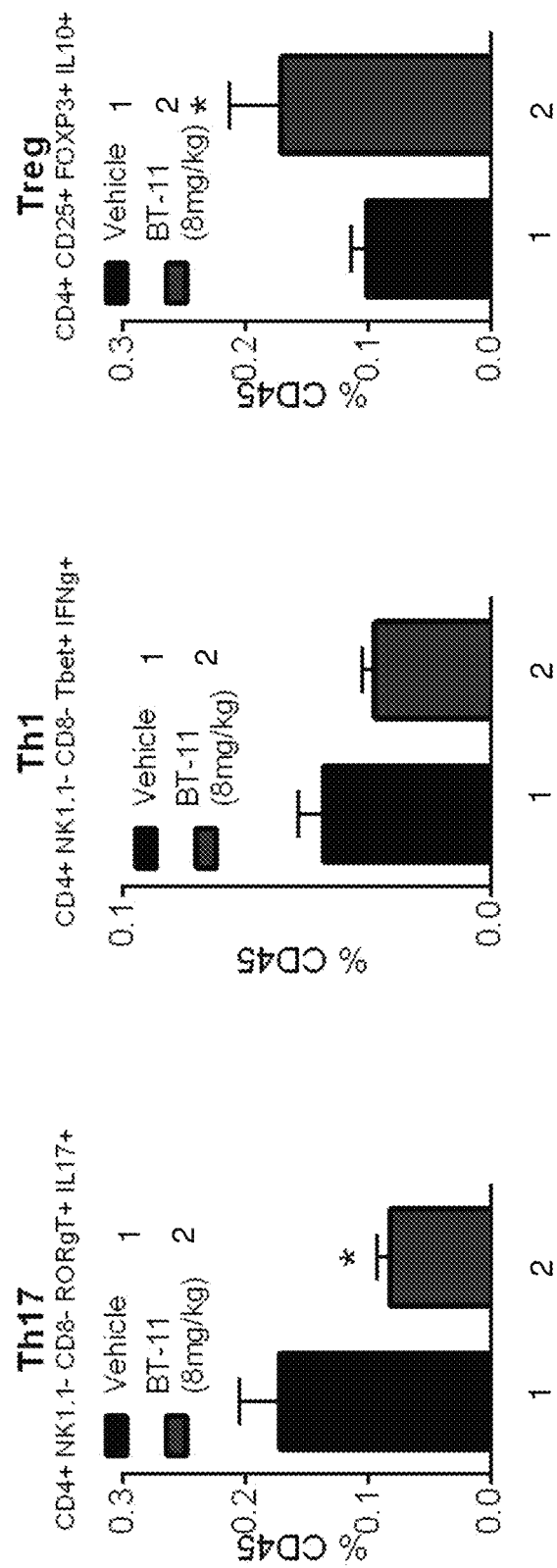

*C. difficile*-infected mice were administered 8 mg/kg/d BT-11 after infection. Results are shown in FIGS. 10A-10C. From day 2 onward, BT-11 treated mice displayed lower levels of symptoms resulting in lower disease activity scores. BT-11 offered complete protection against mortality, observed at a 60% survival rate in vehicle treated controls. However, BT-11 did not induce a decrease in the burden of *C. difficile* within the colon. BT-11 reduced colonic pathology including a decrease in infiltration of leukocytes within the colon. Within the lamina propria, BT-11 reduced neutrophils, Th1 and Th17 cells while providing an increase in regulatory T cells.

Discussion

LANCL2 has emerged as a therapeutic target for immune-mediated [8] and infectious [9] diseases. LANCL2 is expressed in epithelial and immune cells in the gastrointestinal (GI) tract. LANCL2 activation and BT-11 treatment modulates responses in the interface of immunity and metabolism and these immunometabolic mechanisms exert therapeutic actions. These data demonstrates the feasibility of activating immunometabolic mechanisms with BT-11 to ameliorate CDI. Given that disease pathogenesis in CDI is caused in part by its toxins but also due to dysregulated pro-inflammatory immune responses, we have evaluated the efficacy of targeting LANCL2 with BT-11 as an anti-inflammatory *C. difficile* therapy. The data indicate that oral treatment with BT-11 provides complete protection against mortality, decreased disease activity, and reduced inflammation in mice with CDI.

Paramount among immunological contributions to disease pathogenesis in CDI is an imbalance between inflammatory, tissue-damaging Th17 cells and regulatory Treg cells. Importantly, we have shown herein that BT-11 influences the immunometabolic pathways within CD4+ T cells to promote the differentiation and stability of regulatory cell types. These immunometabolic pathways of increasing the stability of FOXP3 expression are of critical importance to provide therapeutic actions during CDI. Because of highly potent bacterially derived toxins, the GI mucosa becomes an increasingly inflammatory environment. This shift in environment causes cells involved in homeostasis and tolerance to the microbiome to lose these capabilities, which exacerbates abnormalities in the commensal microbiome. Through the BT-11 and immunometabolic mechanisms, BT-11 treatment promotes regulatory cells that retain suppressive function in the presence of inflammatory conditions and prevent disease. With an accelerated replenishment of the commensal flora post-antibiotics, the microbiome itself is capable of out-competing and suppressing *C. difficile* growth.

We predict that administering the prepared cells of the invention to an animal will mimic the effects of directly administering BT-11 shown in this example.

REFERENCES

1. Johnson, S. and D. N. Gerding, *Clostridium difficile*-associated diarrhea. Clin Infect Dis, 1998. 26(5): p. 1027-34; quiz 1035-6.
2. Butterworth, S. A., et al., Recent trends in diagnosis and treatment of *Clostridium difficile* in a tertiary care facility. Am J Surg, 1998. 175(5): p. 403-7.
3. Bartlett, J. G., Management of *Clostridium difficile* infection and other antibiotic-associated diarrhoeas. Eur J Gastroenterol Hepatol, 1996. 8(11): p. 1054-61.
4. Pothoulakis, C. and J. T. LaMont, *Clostridium difficile* colitis and diarrhea. Gastroenterol Clin North Am, 1993. 22(3): p. 623-37.
5. Fekety, R. and A. B. Shah, Diagnosis and treatment of *Clostridium difficile* colitis. JAMA, 1993. 269(1): p. 71-5.
6. Pepin, J., et al., Increasing risk of relapse after treatment of *Clostridium difficile* colitis in Quebec, Canada. Clin Infect Dis, 2005. 40(11): p. 1591-7.
7. Musher, D. M., et al., Relatively poor outcome after treatment of *Clostridium difficile* colitis with metronidazole. Clin Infect Dis, 2005. 40(11): p. 1586-90.
8. Lu, P., et al., Lanthionine synthetase component C-like protein 2: a new drug target for inflammatory diseases and diabetes. Curr Drug Targets, 2014. 15(6): p. 565-72.
9. Leber, A., et al., Modeling new immunoregulatory therapeutics as antimicrobial alternatives for treating *Clostridium difficile* infection. Artif Intell Med, 2017. 78: p. 1-13.
10. Buffie, C. G., et al., Precision microbiome reconstitution restores bile acid mediated resistance to *Clostridium difficile*. Nature, 2014. 517(7533): p. 205-208.
11. Leber, A., et al., Systems Modeling of Interactions between Mucosal Immunity and the Gut Microbiome during *Clostridium difficile* Infection. PLoS One, 2015. 10(7): p. e0134849.
12 Bassaganya-Riera J, Reynolds K, Martino-Catt S, et al. Activation of PPAR gamma and delta by conjugated linoleic acid mediates protection from experimental inflammatory bowel disease. Gastroenterology 2004; 127: 777-91.
13. Chen X, Katchar K, Goldsmith J D, Nanthakumar N, Cheknis A, Gerding D N, et al. (2008) A Mouse Model of *Clostridium difficile*-Associated Disease. Gastroenterology 135: 1984-1992.
14. Viladomiu M, Hontecillas R, Pedragosa M, Carbo A, Hoops S, Michalak P, et al. (2012) Modeling the role of peroxisome proliferator-activated receptor gamma and microRNA-146 in mucosal immune responses to *Clostridium difficile*. PLoS One 7: e47525.

Therapeutic Actions if BT-11 in Treating Colorectal Cancer

Colorectal cancer is the third most prevalent cancer worldwide, affecting over 9.4 million individuals in 2015. Metabolism in the progression of cancer contributes both to the behavior of tumor cells themselves and interactions between tumor cells and the immune system. A well-known characteristic of tumor cells is the Warburg effect, the preference for anaerobic glycolysis even in the presence of oxygen. This metabolism of glucose to lactate has a multifaceted benefit for cancer cells: providing fast sources of energy for cellular growth and proliferation, acidifying the microenvironment and consuming metabolic substrate necessary for cytotoxic immune cells. Recently, it has been elucidated that targeting this process is an effective means of controlling tumor progression, growth and metastasis. Cancer cells are capable of inducing anergy and apoptosis in immune cells, preventing the switch toward oxidative phosphorylation that aids in the elimination of cancer cells after recognition. This switch in metabolic profile enables the development of memory T cells that can enhance anti-tumor responses from CD8+ cells. Therefore, targeting immunometabolism represents a treatment for limiting tumor cell growth while enabling immune-mediated elimination of cancer cells.

BT-11 offers a safe, non-cytotoxic option for the treatment of colorectal and other cancers. Unlike other treatments which directly aim to kill cancer cells, BT-11 is capable of inducing potent immunometabolic effects that limit cellular proliferation while stimulating memory responses from the immune system. The administration of BT-11 to cells decreases the activity of lactate dehydrogenase and production of lactate while increasing oxidative phosphorylation pathways. The BT-11-mediated inhibition of lactate metabolism is further linked to a decrease in cellular proliferation, which limits the expansion of progression of tumor cells. In addition, these metabolic influences prevent modulation of the tumor microenvironment decreasing the likelihood of fully established immunoevasive strategies. Further, direct influence of BT-11 on immune cell metabolism increases oxidative phosphorylation and allows for the transition of cells to memory status. BT-11 has been demonstrated to induce memory CD4+ T cell development. With a combined tumor and immune cell potency, BT-11 is a viable chemotherapy alternative in the treatment of colorectal and other cancers. We predict that administering the prepared cells of the invention to an animal will mimic the effects of BT-11 described in this example.

Prevention of Plaque Formation and Arterial Inflammation in Atherosclerosis

Atherosclerosis is a cardiovascular disease characterized by the narrowing of arteries by fibrous plaques within the arterial wall. Atherosclerosis is a leading cause of death in the United States resulting from obesity, high blood pressure and poor diet and contributing to the incidence of heart attack, stroke and kidney failure. Atherosclerosis is a foremost immunometabolic disease caused by the activation of white blood cells due to inflammatory mediators secreted by endothelial cells and high concentration of low density lipoproteins. Over time, this activation leads to the deposition of platelets, cholesterol, and crystallized calcium in the arterial wall. Continuous exposure to modified lipoproteins in conditions of hyperlipidemia leads to the polarization of inflammatory macrophages due to the chronic build-up of intracellular stress. The altered stimulation of key transcription factors, such as SREBP, LXR, and PPARs, lead to activation of NF-κB, NLR and other inflammatory pathways. Another key regulator of immunometabolism in cardiovascular disease is AMPK. The increased expression of inflammatory mediators by secondary immune cells decrease AMPK activity in immune cells and lower the rate of lipid oxidation. The decreased AMPK activity leads to a direct disruption of beneficial immune responses such as the activation of CREB transcription factor activity and anti-inflammatory IL-10 production. The disruption of signaling also directly contributes to the formation of plaques by decreasing the utilization of fatty acids for energy and dysregulating cellular calcium flux.

LANCL2 is an upstream signaling element connected to AMPK and CREB activity as well as the production of IL-10 and regulation of calcium signaling. Its naturally occurring ligand, abscisic acid, has been linked to the modulation of PPAR activity and anti-inflammatory responses during high fat feeding. BT-11 capably reduces the expression of pro-inflammatory, atherosclerosis-associated cytokines, IFNγ and TNFα, when administered to human peripheral blood mononuclear cells and also increases IL-10 production. Intertwined with these effects, BT-11 increases oxidative capacity in immune cells, suggesting the ability to maintain metabolic homeostasis in environments of caloric excess. By influencing both the immune and metabolic pathways affected by atherosclerosis, BT-11 treats pathology and disease in atherosclerosis and prevents the continued recruitment and deposition of cells, cellular fragments and metabolites in arterial walls. We predict that administering the prepared cells of the invention to an animal will mimic the effects of BT-11 described in this example.

Modulation of Glycogen Metabolism in Andersen Disease

Andersen disease is an inborn error of metabolism linked to defects in glycogen storage. It is caused by deficiencies and mutations in the GBE1 gene, which encodes an enzyme responsible for glycogen branching. Unbranched glycogen has a lower solubility, which leads to precipitation and build-up within the heart and liver. Additional evidence indicates that immune cells begin to respond to this abnormal glycogen. Antibodies reactive to polyglucosan have been isolated from heart and liver tissue of Andersen disease and Lafora disease patients. The uptake and reactivity of polyglucosans by immune cells may exacerbate the damage to heart and liver tissue, accelerating the deterioration of patient health. This is further supported by the elevation of chitotriosidase within Andersen disease patients. Chitotriosidase is an enzyme and inflammatory marker produced by macrophages during defense responses and chronic liver disease.

BT-11 and other related LANCL2 ligands are aligned with an efficient and controlled oxidation of glucose, while LANCL2 activation has been linked to the homeostasis of glucose. Activation of LANCL2 by BT-11 or other ligands alleviates build-up of glycogen in Andersen disease patients. Also contributing to the benefit of BT-11 or other related ligands is the modulation of defense response. The production of antibodies and chitotriosidase suggest that the immune system recognizes unbranched glycogen as foreign, leading to increased inflammation. BT-11 and other related ligands are capable of inducing tolerance toward typical antigens. With maintenance of immune tolerance, unbranched glycogen is able to be secreted and removed from the body. We predict that administering the prepared cells of the invention to an animal will mimic the effects of BT-11 described in this example.

Restoration of Metabolic and Inflammatory Abnormalities in Fibromyalgia

Fibromyalgia is a disorder that causes widespread pain throughout the body. The disease afflicts over 3 million people within the United States and has no cure. Current treatments include serotonin uptake inhibitors, painkillers, and nonsteroidal anti-inflammatory drugs that aim to reduce the chronic pain, fatigue and mood changes caused by the disease. Recently, fibromyalgia patients have been identified to have elevated levels of inflammatory markers such as the neutrophil-attracting chemokine, IL-8, and the broad inflammatory marker C-reactive protein. In particular, glia cells of fibromyalgia patients produce altered chemokine and cytokine profiles, indicating an involvement of the immune system within the symptoms and pathogenesis of the disease. Additionally, the metabolism of immune cells within fibromyalgia patients is shifted compared to healthy controls. The fibromyalgia mononuclear cells had reductions in mitochondrial membrane potential and coenzyme Q10 combined with increased superoxide formation and lipid peroxidation. These changes are emblematic of highly inflammatory immune cells and overall oxidative stress. Further, the severity of pain and other symptoms has been inversely correlated in fibromyalgia patients with monocyte subpopulations associated with regulatory responses.

BT-11 and other related compounds that target LANCL2 or other immunometabolic pathways decrease the oxidative stress caused by certain metabolic pathways within immune cells. This reduction in oxidative stress and production of superoxide can reduce the overactivation of nerve cells and stimulation of glial cells to produce inflammatory chemokines. Also, the activation of LANCL2 can influence the polarization of monocytes and other mononuclear cells toward regulatory subsets. These cell subsets are associated with anti-inflammatory responses, tissue homeostasis and wound healing. The combined effects on the metabolic profiles of immune cells and the polarization of regulatory monocytes subsets make BT-11 a novel and ideal candidate for the treatment of fibromyalgia and other chronic pain disorders. We predict that administering the prepared cells of the invention to an animal will mimic the effects of BT-11 described in this example.

Ex Vivo Treatment of CD4+ T Cells for Treatment of Inflammatory Disease

BT-11 through immunometabolic signaling changes the phenotypic profile of cells in vitro and immune responses in vivo. In particular, BT-11 shapes CD4+ T cells to increase expression of FOXP3, increase suppressive capacity, and increase stability of these regulatory cells in inflammatory conditions. Adoptive transfer of cells treated ex vivo with BT-11 is therefore beneficial in treating inflammatory diseases and disorders with inadequate CD4+ T cell responses, such as inflammatory bowel disease, graft versus host disease, and others described herein.

Methods

Naïve CD4+ T cells were isolated from the spleens of mice by magnetic sorting. The isolated cells were incubated in anti-CD3/anti-CD28 coated 96 well plates in Treg differentiation media. The Treg differentiation media was Iscove's Modified Dulbecco's Medium (IMDM) media (ThermoFisher Scientific) supplemented with fetal bovine serum, HEPES, penicillin/streptomycin, L-glutamine, and differentiation agents. The Treg differentiation agents were 10 nM all-trans-retinoic acid and 5 ng/mL TGF-β. Additional experiments were conducted comparing differentiation in the Treg differentiation media with and without the addition of 10 ng/mL IL-2 or IL-12. Cells were incubated with vehicle, 10 nM, or 100 nM BT-11 in differentiation media for 48 hours prior to assay. Prior to assay, cells were stimulated with PMA and ionomycin for 6 hours.

In transfer experiments, donor spleens were crushed and enriched for CD4+ fraction by magnetic sorting. CD4+ CD45RB$^{hi}$CD25− (Teff) and CD4+CD45RB$^{lo}$CD25+ (Treg$_g$) cells were sorted by a FACSAria cell sorter. Isolated Tregs were cultured for 12 h in the presence of vehicle or BT-11 (100 nM). Isolated Teff were cultured for 12 h in vehicle. Based on indicated experimental group, Rag2−/− recipient mice received 4×10$^5$ Teff and 1×10$^5$ Treg cells from vehicle or BT-11 treated groups by intraperitoneal injection. Mice were weighed and scored weekly until euthanasia at 5 weeks post-transfer.

Colonic lamina propria lymphocytes and cultured cells were plated in 96 well plates (6×10$^5$ cells/well) and processed for immunophenotyping by flow cytometry as previously described. Briefly, cells were incubated with fluorochrome conjugated antibodies to extracellular markers: CD45, CD4, CD3, CD25, CD8. Samples needing a secondary staining were incubated with secondary antibodies, or streptavidin-conjugated fluorochrome. The samples were then fixed and permeabilized. Cells were incubated with antibodies to intracellular markers: Tbet, IFNγ, IL10, FOXP3, IL17, RORγT. Data was acquired with a BD FACS Celesta flow cytometer and analyzed using FACS Diva software (BD Pharmingen).

Results

Figure 11A:
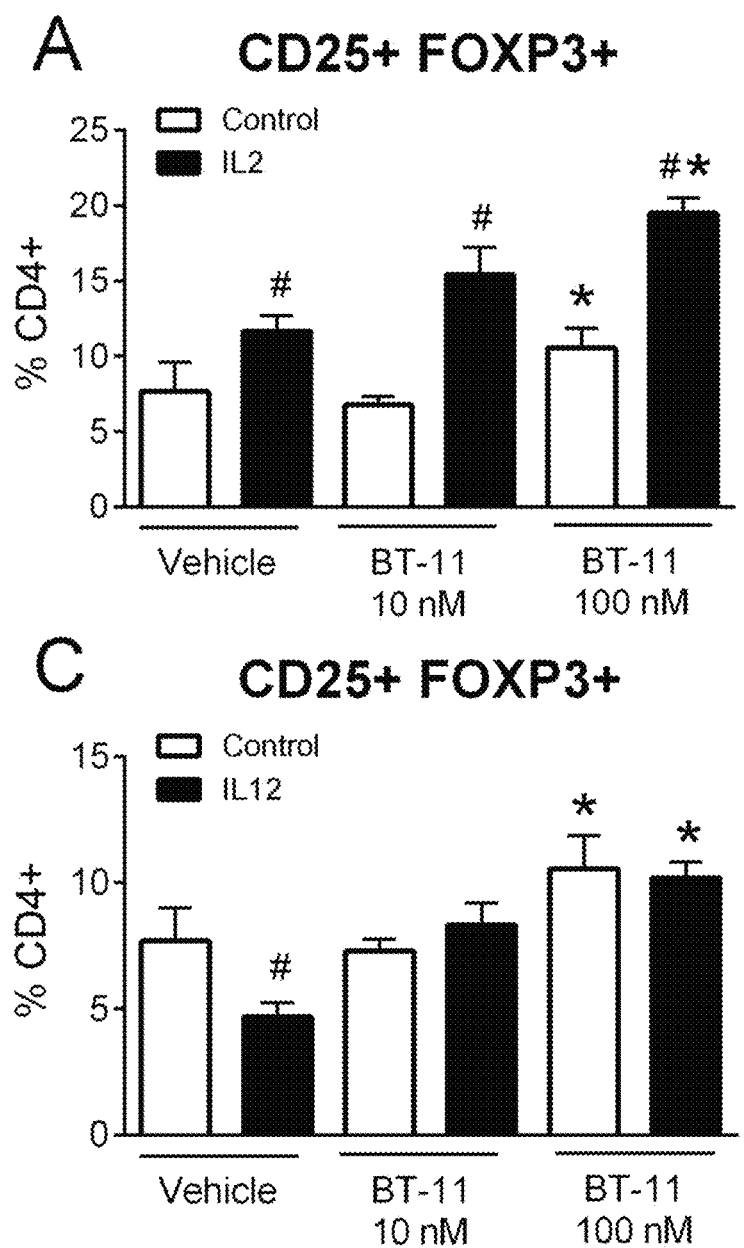
FIGS. 11A-11B. IL-2 and BT-11 enhance differentiation of CD25+ FOXP3+ T cells. Naïve CD4+ T cells were isolated from the spleens of wild-type mice and were differentiated into regulatory CD4+ T cells in the presence of vehicle or BT-11 (10, 100 nM) treatment. Differentiation into CD25+ FOXP3+(FIG. 11A, panel A) and CD25+ Tbet+ (FIG. 11B, panel B) cells in standard differentiation media or differentiation media containing IL-2 (10 ng/mL) by flow cytometry. Differentiation into CD25+ FOXP3+(FIG. 11A, panel C) and CD25+ Tbet+(FIG. 11B, panel D) cells in standard differentiation media or differentiation media containing IL-12 (10 ng/mL) by flow cytometry. Data is displayed as mean with SEM (n=8). Statistical significance (P<0.05) by treatment is indicated by asterisk (*) and by IL-2/IL-12 presence by (#).
Figure 11B:
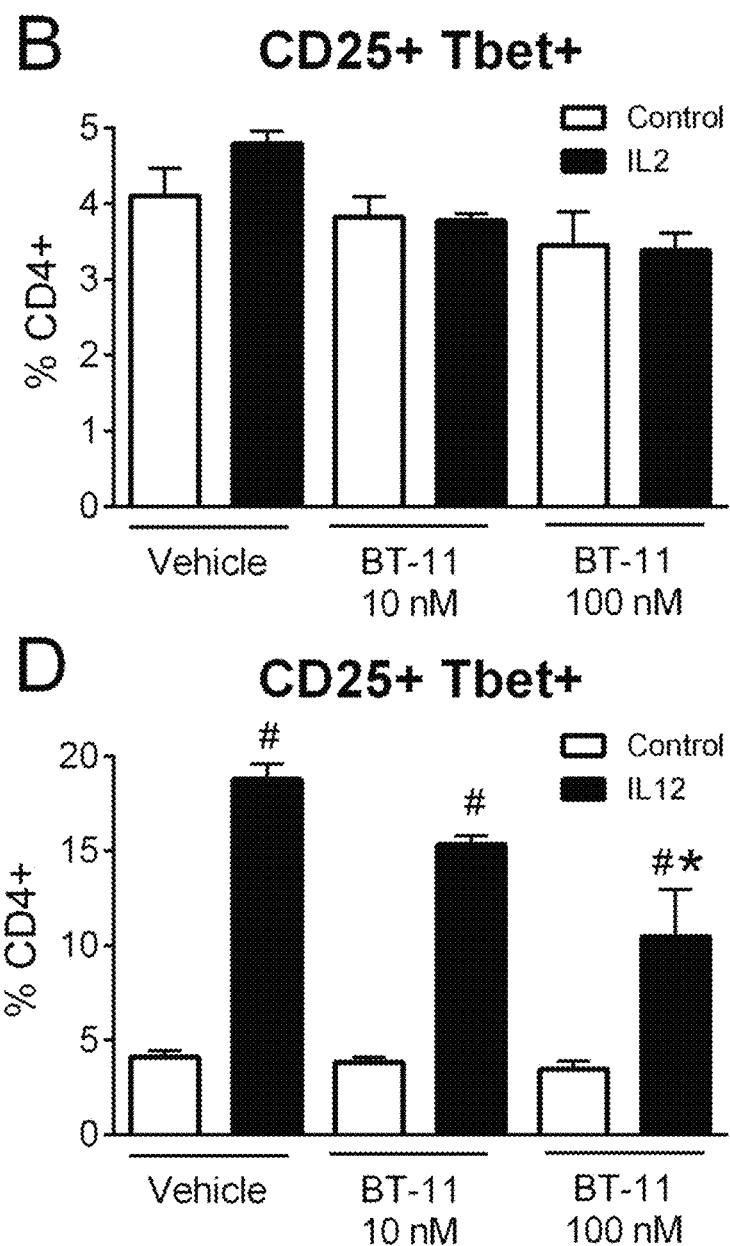

With the importance of CD25+ FOXP3+ regulatory CD4+ T cells to the efficacy of BT-11, we aimed to determine the direct effect of BT-11 on their differentiation and ability to retain phenotype in inflammatory conditions. Naïve CD4+ T cells were differentiated into Tregs in vitro in the presence or absence of IL-2 according to the methods described above. BT-11 treatment (100 nM) significantly increased the establishment of a CD25+ FOXP3+ subtype in the absence of IL-2, a difference that was further accentuated by the addition of IL-2 (FIG. 11A, panel A). At concentrations as low as 10 nM, BT-11 induced significantly more CD25+ FOXP3+ cells in the presence of IL-2. Only low levels of a mixed CD25+ Tbet+ subtype were observed under these differentiation conditions, and this was not statistically altered by BT-11 (FIG. 11B, panel B). Of note, a slight numerical increase occurred in vehicle treated controls with the addition of IL-2, which was absent in the presence of BT-11. Meanwhile, BT-11 retained significantly higher levels of CD25+ FOXP3+ cells in IL-12-treated samples (FIG. 11A, panel C). This is contrasted with the suppression of CD25+ FOXP3+ cells in IL-12-treated samples in the absence of BT-11 (FIG. 11A, panel C). The addition of IL-12 also induced an increase in CD25+ Tbet+ cells in all groups, though BT-11 provided a dose-dependent protection against this mixed subset (FIG. 11B, panel D).

Figure 12A:
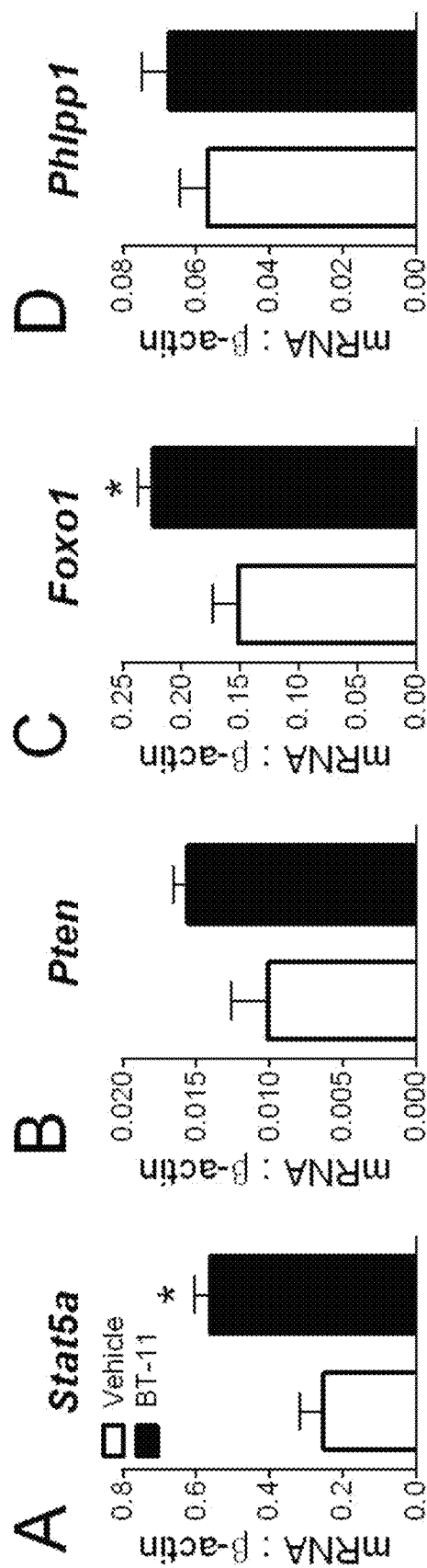
FIGS. 12A-12D. BT-11 increases STAT5 phosphorylation to establish stable CD25+ cellular differentiation. Expression of Stat5a (FIG. 12A, panel A), Pten (FIG. 12A, panel B), Foxo1 (FIG. 12A, panel C) and Phlpp1 (FIG. 12A, panel D) by qRT-PCR in CD4+ T cells isolated from the colons of vehicle and BT-11 treated Mdr1a-/- mice at 10 weeks of age during active disease. Normalized expression of p-STAT5a (FIG. 12B, panel E) and p-FOXO1 (FIG. 12B, panel F) by Western blot in in vitro differentiated Tregs with vehicle or BT-11 (10, 100 nM) with or with IL-2 (10 ng/mL) or IL-12 (10 ng/mL). Differentiation into CD25+ FOXP3+(FIG. 12C, panel G) and CD25+ Tbet+(FIG. 12C, panel H) cells in differentiation media containing IL-2 (10 ng/mL) and inhibitors SF1670 or STAT5i by flow cytometry. Differentiation into CD25+ FOXP3+(FIG. 12D, panel I) and CD25+ Tbet+ (FIG. 12D, panel J) cells in differentiation media containing IL-12 (10 ng/mL) and inhibitors SF1670 or STAT5i by flow cytometry. Data is displayed as mean with SEM (n=8). Statistical significance (P<0.05) by treatment is indicated by asterisk (*) and by inhibitor presence by (#).
Figure 12B:
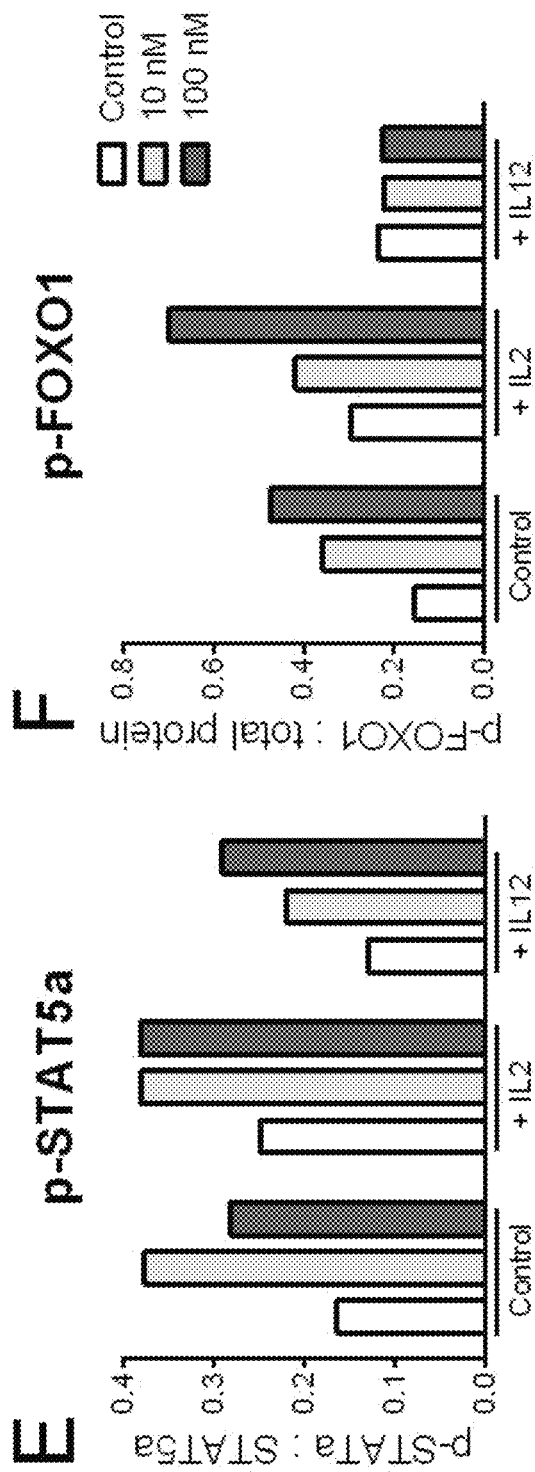
Figure 12C:
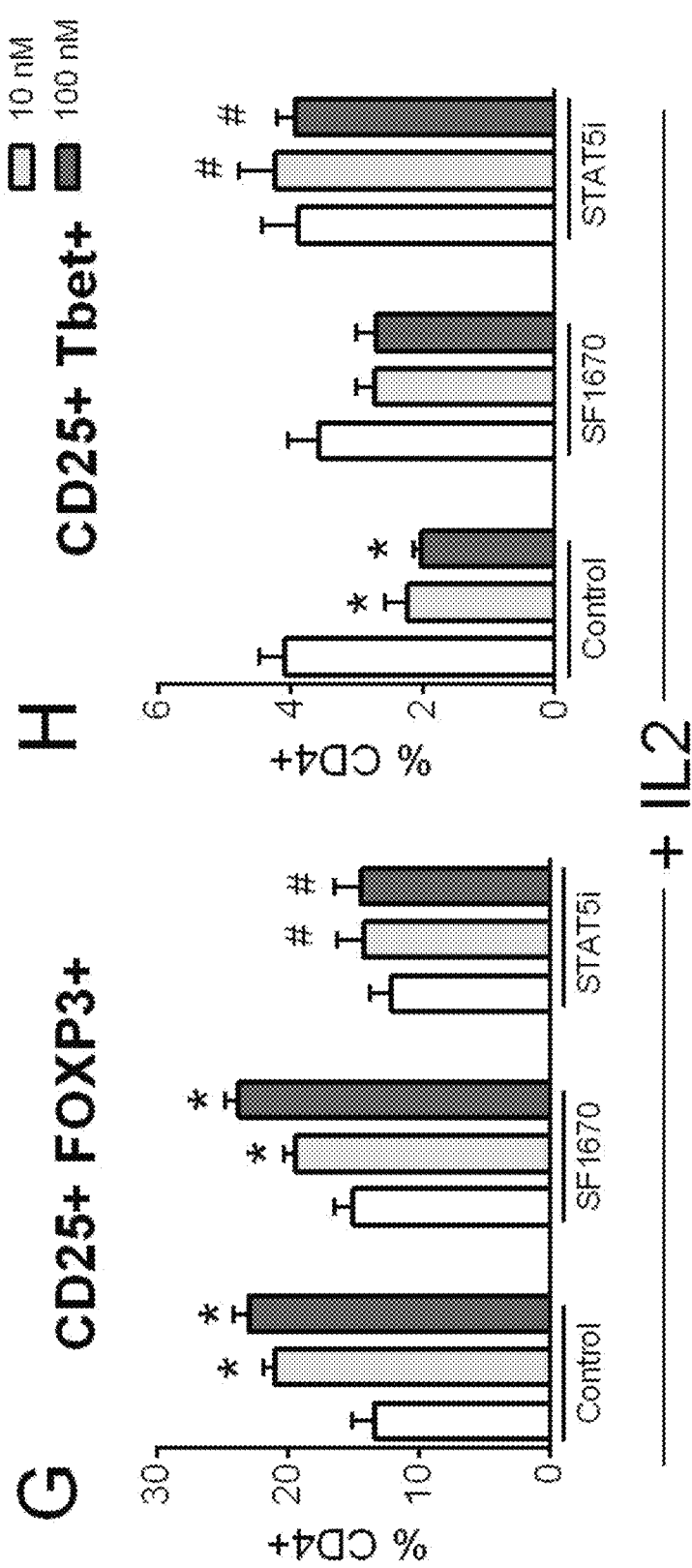
Figure 12D:
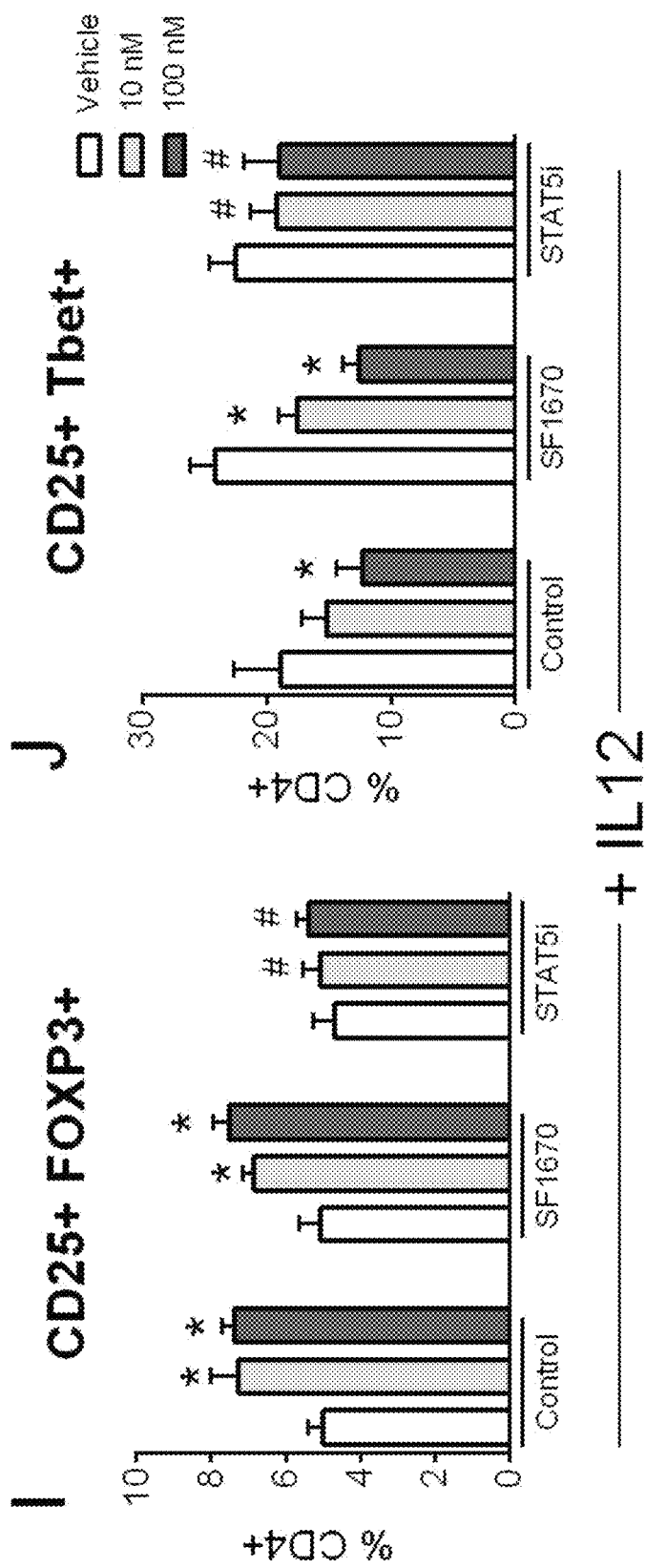

To identify signaling pathways modulated by BT-11 in vivo, we isolated colonic CD4+ T cells from vehicle- and BT-11-treated Mdr1a−/− mice at presentation of colitis at 10 weeks of age. In CD4+ T cells, oral BT-11 treatment resulted in significantly higher expression of Stat5a (FIG. 12A, panel A) and Foxo1 (FIG. 12A, panel C), two members of the IL-2 signaling pathway. Meanwhile, expression of Pten (FIG. 12A, panel B) and Phlpp1 (FIG. 12A, panel D) were slightly, but non-significantly, increased. In vitro, STAT5a is phosphorylated in a greater ratio in BT-11-treated samples in the base Treg differentiation media and also in the Treg differentiation media supplemented with either IL-2 or IL-12 (FIG. 12B, panel E). FOXO1 is similarly affected in both the base Treg differentiation media and the Treg differentiation media containing IL-2, but not in the Treg differentiation media containing IL-12 (FIG. 12B, panel F). Cells were also differentiated in the presence of inhibitors for PTEN (SF1670) or STAT5 (STAT5i). In the Treg differentiation media containing both IL-2 (FIG. 12C, panels G, H) or IL-12 (FIG. 12D, panels I, J), the addition of STAT5i prevented the effects of BT-11 on CD25+ FOXP3+ and CD25+ Tbet+ cells. In contrast, SF1670 only prevented effects of BT-11 on CD25+ Tbet+ cells in IL-2 containing media (FIG. 12C, panel H).

Rag2−/− mice lack mature T and B lymphocytes. Therefore, these mice fail to develop mechanisms of self-tolerance, microbial homeostasis, and overall immunoregulation. Transfer of naïve CD4+ T cells into Rag2−/− mice induces intestinal inflammation resulting from the absence of these mechanisms through in vivo expansion of the transferred cells and differentiation into inflammatory phenotypes in a manner similar to those experienced in active inflammatory autoimmune diseases including but not limited to inflammatory bowel disease. We hypothesized that the transfer of regulatory cells treated ex vivo with BT-11 would confer mechanisms of homeostasis and immunoregulation to recipient animals, which we found to be the case.

Figure 13:
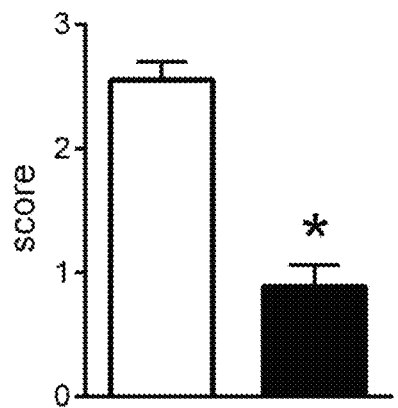
FIG. 13. Ex vivo treatment of regulatory CD4+ T cells stimulates increased regulatory effects in vivo. Mice were adoptively transferred effector T cells (Teff) and regulatory CD4+ T cells (Tregs) that were treated ex vivo with BT-11 or vehicle for 12 h. Mice that received the BT-11-treated Tregs had lower cumulative disease activity (intestinal inflammation) and shifts in colonic CD4+ T cell populations five weeks post-transfer.
Figure 13:
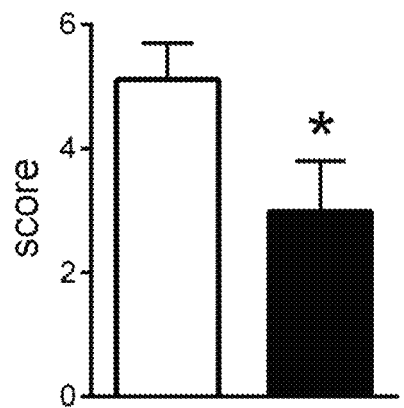
Figure 13:
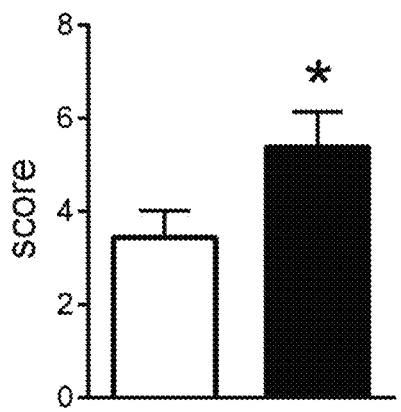
Figure 13:
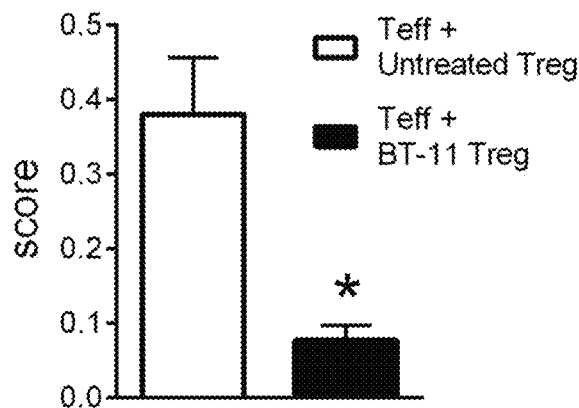

The adoptive transfer of Tregs treated ex vivo with BT-11 (100 nM) decreased overall disease severity and provided maintenance of immune benefits up to the tested limit duration of 5 weeks post-transfer (FIG. 13). In addition to overall improvement of disease, ex vivo treatment of Tregs with BT-11 resulted in changed phenotypes of colonic lamina propria cells. In BT-11-treated Treg groups, IFNγ-producing and IL-17+ RORγT+CD4+ T cells were reduced. Meanwhile, CD25+ Tregs were increased, indicating an increased stability and increased ability to serve as a founder population of regulatory cells. Further, interaction with the IL-2/STAT5 signaling axis promotes important changes in the cytokine and chemokine microenvironment that amplify the effects of transferred cells.

These results show that the effects of BT-11 on immune cells when administered in vivo can be replicated when treating immune cells ex vivo. We predict that administering the prepared cells of the invention to an animal will be effective in treating any of the conditions described herein beyond inflammatory diseases such as IBD.

EXEMPLARY EMBODIMENTS OF ASPECTS OF THE INVENTION

1. A method of treating a condition in an animal with a compound or a prepared cell generated by contacting a precursor cell with the compound, the method comprising administering an effective amount of the compound or the prepared cell to the animal, wherein the condition comprises at least one of an infectious disease, a hyperproliferative disorder, an inborn error of metabolism, a chronic immunometabolic disease, an autoimmune disease, organ transplant rejection, an inflammatory disorder, and chronic pain, and wherein the compound comprises:

a compound of formula Z-Y-Q-Y'-Z', or a pharmaceutically acceptable salt or ester thereof, wherein:

Z is:

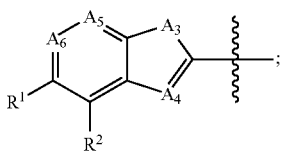

Y is:

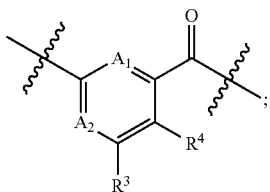

Q is piperazine-1,4-diyl; 2,5-diazabicyclo[2.2.1]heptane-2,5-diyl; 2,5-diazabicyclo[2.2.2]octane-2,5-diyl; 1,4-diazepane-1,4-diyl; benzene-1,4-diamine-$N^1,N^4$-diyl; ethane-1,2-diamine-$N^1,N^2$-diyl; $N^1,N^2$-dialkylethane-1,2-diamine-$N^1,N^2$-diyl; propane-1,3-diamine-$N^1,N^3$-diyl; $N^1,N^3$-dialkylpropane-1,3-diamine-$N^1,N^3$-diyl; 1,4-diaminoanthracene-9,10-dione-1,4-diyl; $C_6$ arene-1,4-diamine-$N^1,N^4$-diyl wherein the arene is substituted with one to four substituents in the 2, 3, 5, or 6 positions and wherein the substituents are independently selected from the group consisting of —C(O)O($C_1$ to $C_6$)alkyl, OH, O($C_1$ to $C_6$)alkyl, ($C_1$ to $C_6$)alkyl, $CF_3$, F, Cl, and Br; or substituted piperazine-1,4-diyl wherein the piperazine is substituted with one to eight substituents in the 2, 3, 5, or 6 positions and wherein the substituents are independently selected from the group consisting of ($C_1$ to $C_6$)alkyl, aryl, aryl($C_1$ to $C_6$)alkyl, C(O)OH, and C(O)O($C_1$ to $C_6$)alkyl;

Y' is:

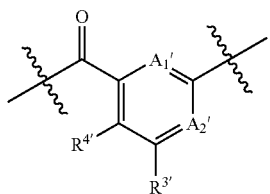

or a single bond; and

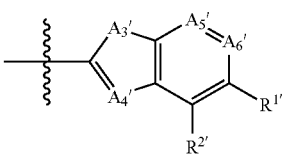

or $R^5$;

wherein:

Y' is a single bond only when Z' is $R^5$;

$A_1$ and $A_1$', if present, are each independently N, N($C_1$ to $C_6$)alkyl, O, S, or $CR^6$;

$A_2$ and $A_2$', if present, are each independently N or $CR^7$;

$A_3$ and $A_3$', if present, are each independently $NR^8$, O, or S;

$A_4$ and $A_4$', if present, are each independently N or $CR^9$;

$A_5$ and $A_5$', if present, are each independently N or $CR^{10}$;

$A_6$ and $A_6$', if present, are each independently N or $CR^{11}$;

$R^1, R^{1'}, R^2, R^{2'}, R^3, R^{3'}, R^4, R^{4'}, R^5, R^6, R^7, R^8, R^9, R^{10}$, and $R^{11}$, if present, are in each instance independently selected from the group consisting of hydrogen; alkyl; halo; trifluoromethyl; dialkylamino wherein each alkyl is independently selected; —$NH_2$; alkylamino; arylalkyl; heteroarylalkyl; heterocycloalkyl; substituted heterocycloalkyl substituted with 1 to 2 substituents independently selected from the group consisting of C(O)OH, —C(O)O($C_1$ to $C_6$)alkyl, ($C_1$ to $C_6$)alkyl, —$CF_3$, F, Cl, and Br; and substituted heteroarylalkyl;

wherein the substituted heteroarylalkyl is substituted with 1 to 3 substituents independently selected from the group consisting of —$NH_2$; —NH($C_1$ to $C_6$)alkyl; —N(($C_1$ to $C_6$)alkyl)$_2$ wherein each alkyl is independently selected; alkyl; halo; aryl; substituted aryl substituted with 1 to 3 substituents independently selected from the group consisting of —$SO_2R^{12}$, —$OR^{13}$, -halo, —CN, —$CF_3$, aminoalkyl-, —$S(O)R^{14}$, and alkyl; heterocycloalkyl; heteroaryl; substituted aryl substituted with 1 to 3 substituents independently selected from the group consisting of alkyl, —$CF_3$, F, Cl, and Br; alkylamino-; heterocycloalkyl-alkyl-amino-; alkylaminoalkylamino-; —NHC(O)$OR^{15}$; —NHC(O)$NR^{16}R^{17}$; —C(O)$NR^{16}R^{17}$; and substituted heteroaryl substituted with 1 to 3 substituents selected from the group consisting of alkyl, halo, CN, $NH_2$, —NH($C_1$-$C_6$ alkyl), —N($C_1$-$C_6$ alkyl)$_2$ wherein each alkyl is independently selected, —$CF_3$, and substituted aryl substituted with 1 to 3 substituents independently selected from the group consisting of —$S(O)_2R^{15}$ and —CN;

wherein $R^{12}, R^{13}, R^{14}, R^{15}, R^{16}$, and $R^{17}$ are each independently selected from the group consisting of $C_1$-$C_6$alkyl, dialkylamino comprising independently selected $C_1$-$C_6$ alkyl, —$NH_2$, alkylamino, heterocycloalkyl, and substituted heterocycloalkyl substituted with one to two substituents independently selected from the group consisting of —C(O)O($C_1$-$C_6$ alkyl) and —$C_1$-$C_6$ alkyl; or a compound comprising formula A-B-C, or a pharmaceutically acceptable salt or ester thereof, wherein:

A is:

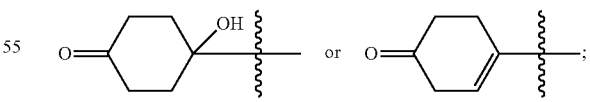

B is:

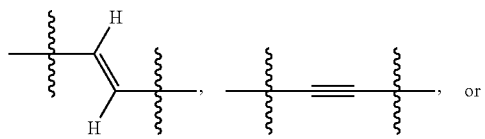

-continued

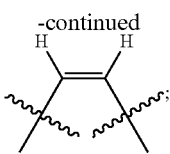

and
C is:

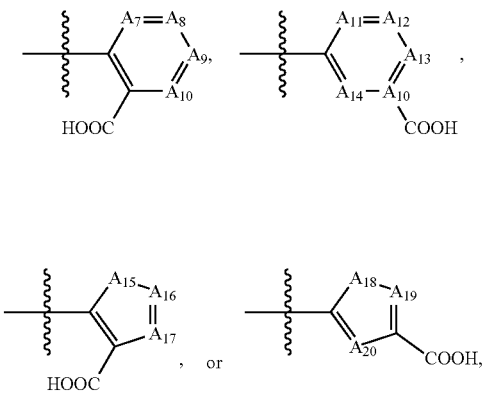

wherein:
A$_7$, A$_8$, A$_9$, A$_{10}$, A$_{11}$, A$_{12}$, A$_{13}$, and A$_{14}$ are each independently selected from CH, CR$^{18}$, and N;

A$_{15}$, A$_{16}$, A$_{17}$, A$_{18}$, A$_{19}$, and A$_{20}$ are each independently selected from CH, CR$^{19}$, N, NR$^{20}$, O, and S, with the proviso that only one of A$_{15}$, A$_{16}$, and A$_{17}$ can be N, NR$^{20}$, O, or S and only one of A$_{18}$, A$_{19}$, and A$_{20}$ can be N, NR$^{20}$, O, or S;

R$^{18}$ and R$^{19}$ are each independently selected from C$_1$-C$_6$ alkyl; C$_1$-C$_6$ dialkylamino, wherein each C$_1$-C$_6$ alkyl is independently selected; —NH$_2$; alkylamino; heterocycloalkyl; and substituted heterocycloalkyl, wherein the substituted heterocycloalkyl is substituted with one to two substituents independently selected from the group consisting of: —C(O)O(C$_1$-C$_6$ alkyl) and C$_1$-C$_6$ alkyl;

wherein in compounds with more than one CR$^{18}$ each R$^{18}$ is independently selected,
and in compounds with more than one CR$^{19}$ each R$^{19}$ is independently selected; and R$^{20}$ is C$_1$-C$_6$ alkyl.

2. The method of embodiment 1, wherein the infectious disease comprises a bacterial disease.
3. The method of embodiment 2, wherein the bacterial disease comprises *C. difficile* infection.
4. The method of embodiment 1, wherein the hyperproliferative disorder comprises cancer.
5. The method of embodiment 4, wherein the cancer comprises a cancer of the gastrointestinal tract.
6. The method of embodiment 5, wherein the cancer of the gastrointestinal tract comprises colorectal cancer.
7. The method of embodiment 1, wherein the hyperproliferative disorder comprises familial adenomatous polyposis.
8. The method of embodiment 1, wherein the inborn error of metabolism comprises a glycogen storage disease.
9. The method of embodiment 8, wherein the glycogen storage disease comprises Andersen disease.
10. The method of embodiment 1, wherein the chronic immunometabolic disease comprises cardiovascular disease.
11. The method of embodiment 10, wherein the cardiovascular disease comprises atherosclerosis.
12. The method of embodiment 1, wherein the chronic immunometabolic disease comprises hypertension.
13. The method of embodiment 1, wherein the autoimmune comprises at least one of systemic lupus erythematosus and multiple sclerosis.
14. The method of embodiment 1, wherein the autoimmune disease comprises a cancer-immunotherapy-induced autoimmune disease.
15. The method of embodiment 14, wherein the cancer-immunotherapy-induced autoimmune disease comprises a cancer immunotherapy-induced rheumatic disease.
16. The method of embodiment 1, wherein the inflammatory disorder comprises acute colonic diverticulitis.
17. The method of embodiment 1, wherein the inflammatory disorder comprises radiation-induced inflammation of the gastrointestinal tract.
18. The method of embodiment 17, wherein the radiation-induced inflammation of the gastrointestinal tract comprises at least one of radiation proctitis, radiation enteritis, and radiation proctosigmoiditis.
19. The method of embodiment 1, wherein the chronic pain comprises fibromyalgia.
20. The method of embodiment 1, wherein the condition comprises inflammatory bowel disease.
21. The method of embodiment 1, wherein the condition comprises Crohn's disease.
22. The method of embodiment 1, wherein the condition comprises ulcerative colitis.

What is claimed is:
1. A method comprising generating prepared cells from precursor cells, the generating comprising:
obtaining peripheral blood mononuclear cells comprising the precursor cells; and
contacting the precursor cells, in vitro, with a compound in an amount and for a time effective to induce a compound-dependent difference in the prepared cells with respect to the precursor cells, wherein:
the precursor cells comprise one or more of naïve CD4+ T cells and regulatory CD4+ T cells;
the prepared cells comprise regulatory CD4+ T cells;
the compound is a compound of formula:

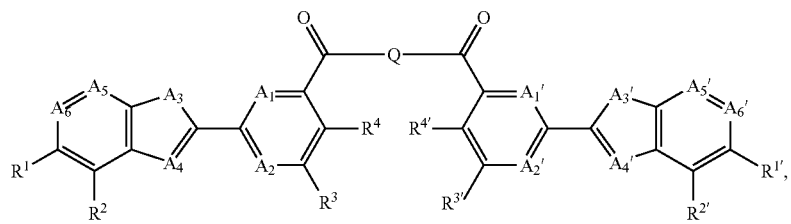

or a pharmaceutically acceptable salt thereof, wherein:
Q is piperazine-1,4-diyl or substituted piperazine-1,4-diyl wherein the piperazine in the substituted piperazine-1,4-diyl is substituted with one to eight substituents independently selected from the group consisting of ($C_1$ to $C_6$)alkyl, aryl, aryl($C_1$ to $C_6$)alkyl, C(O)OH, and C(O)O($C_1$ to $C_6$)alkyl;
$A_1$ and $A_{1'}$ are each independently N or $CR^6$;
$A_2$ and $A_2'$ are each independently N or $CR^7$;
$A_3$ is $NR^8$;
$A_3'$ is $NR^8$, O, or S;
$A_4$ and $A_4'$ are each independently N or $CR^9$;
$A_5$ and $A_5'$ are each independently N or $CR^{10}$;
$A_6$ and $A_6'$ are each independently N or $CR^{11}$; and
$R^1, R^{1'}, R^2, R^{2'}, R^3, R^{3'}, R^4, R^{4'}, R^6, R^7, R^8, R^9, R^{10}$ and $R^{11}$, if present, are in each instance independently selected from the group consisting of hydrogen, alkyl, halo, trifluoromethyl, dialkylamino wherein each alkyl is the same or different, —$NH_2$, alkylamino, and arylalkyl; and the compound-dependent difference comprises at least one of an increase in expression of IL-10 or an ortholog thereof, an increase in expression of FOXP3 or an ortholog thereof, a decrease in expression of TNFα or an ortholog thereof, a decrease in expression of IFNγ or an ortholog thereof, a decrease in expression of Tbet or an ortholog thereof, an increase in expression of Lag3 or an ortholog thereof, an increase in expression of Socs2 or an ortholog thereof, an increase in expression of Irf7 or an ortholog thereof, an increase in expression of P2rx7 or an ortholog thereof, an increase in expression of Capn3 or an ortholog thereof, an increase in expression of Ikzf2 or an ortholog thereof, an increase in expression of Stat5a or an ortholog thereof, an increase in expression of Pten or an ortholog thereof, an increase in expression of Foxo1 or an ortholog thereof, an increase in expression of Phlpp1 or an ortholog thereof, an increase in phosphorylation of STAT5a or an ortholog thereof, an increase in phosphorylation of FOXO1 or an ortholog thereof, and an increase in pyruvate kinase activity.

2. The method of claim 1, wherein the contacting comprises contacting the precursor cells with the compound and an agent comprising one or more of all-trans-retinoic acid, TGF-β, phorbol myristate acetate, ionomycin, rapamycin, and IL-2.

3. The method of claim 1, wherein the contacting comprises contacting the precursor cells with the compound, all-trans-retinoic acid, TGF-β, and IL-2.

4. The method of claim 3, wherein the contacting the precursor cells with the compound comprises contacting the peripheral blood mononuclear cells with the compound.

5. The method of claim 4, further comprising, after the contacting the peripheral blood mononuclear cells with the compound, isolating the prepared cells from the peripheral blood mononuclear cells.

6. The method of claim 1, further comprising, after the obtaining the peripheral blood mononuclear cells and prior to the contacting the precursor cells with the compound, isolating the precursor cells from the peripheral blood mononuclear cells.

7. The method of claim 1, further comprising administering the prepared cells to an animal.

8. The method of claim 7, wherein the prepared cells are administered in an amount sufficient to treat a condition.

9. The method of claim 8, wherein the condition comprises an inflammatory disorder, an infectious disease, a hyperproliferative disorder, an inborn error of metabolism, a chronic immunometabolic disease, an autoimmune disease, organ transplant rejection, and chronic pain.

10. The method of claim 8, wherein the condition comprises inflammatory bowel disease.

11. The method of claim 7, wherein the administering comprises parenterally administering the prepared cells to the animal.

12. The method of claim 11, wherein the parenterally administering comprises injecting or infusing the prepared cells into the bloodstream of the animal.

13. The method of claim 7, wherein the administering comprises enterally administering the prepared cells to the animal.

14. The method of claim 7, wherein the peripheral blood mononuclear cells are autologous cells obtained from the animal.

15. The method of claim 7, wherein the obtaining the peripheral blood mononuclear cells comprises obtaining the peripheral blood mononuclear cells from the animal.

* * * * *